United States Patent [19]
Tung et al.

[11] Patent Number: 6,127,372
[45] Date of Patent: Oct. 3, 2000

[54] SULFONAMIDE INHIBITORS OF ASPARTYL PROTEASE

[75] Inventors: Roger Dennis Tung, Arlington; Francesco Gerald Salituro, Marlborough; David D. Deininger, Arlington; Mark Andrew Murcko, Holliston; Perry Michael Novak, Milford; Govinda Rao Bhisetti, Lexington, all of Mass.

[73] Assignee: Vertex Pharmaceuticals, Incorporated, Cambridge, Mass.

[21] Appl. No.: 08/424,372

[22] PCT Filed: Feb. 24, 1995

[86] PCT No.: PCT/US95/02420

§ 371 Date: Apr. 1, 1996

§ 102(e) Date: Apr. 1, 1996

[87] PCT Pub. No.: WO95/24385

PCT Pub. Date: Sep. 14, 1995

Related U.S. Application Data

[63] Continuation-in-part of application No. 08/207,580, Mar. 7, 1994, abandoned.

[51] Int. Cl.[7] ..................... A61K 31/351; A61K 31/381; A61K 31/4192; A61K 31/426
[52] U.S. Cl. ................... 514/253.11; 514/238.2; 514/277; 514/357; 514/365; 514/386; 514/404; 514/424; 514/452; 514/470; 514/473; 544/162; 544/237; 544/349; 544/360; 544/383; 544/388; 546/141; 546/146; 546/225; 546/226; 546/316; 546/337; 546/338; 546/355
[58] Field of Search ..................... 514/255, 277, 514/365, 238.2, 249, 357, 386, 404, 424, 452, 470, 473; 544/360, 162, 237, 349, 383; 546/225, 226, 355; 548/200, 322.5, 370.1, 543; 549/373, 465, 475

[56] References Cited

U.S. PATENT DOCUMENTS

| | | | |
|---|---|---|---|
| 3,743,722 | 7/1973 | Mohrs et al. | 424/98 |
| 4,330,542 | 5/1982 | Descamps et al. | 424/248.5 |
| 4,629,724 | 12/1986 | Ryono et al. | 514/18 |
| 5,196,438 | 3/1993 | Martin et al. | 514/311 |
| 5,354,866 | 10/1994 | Kempf et al. | 546/265 |

FOREIGN PATENT DOCUMENTS

| | | |
|---|---|---|
| 0 022 118 | 1/1981 | European Pat. Off. |
| 0 181 071 | 3/1986 | European Pat. Off. |
| 0 264 795 | 4/1988 | European Pat. Off. |
| 0 346 847 | 12/1989 | European Pat. Off. |
| 0 364 804 | 4/1990 | European Pat. Off. |
| 0 468 641 | 1/1992 | European Pat. Off. |
| 0 486 948 | 5/1992 | European Pat. Off. |
| 0 541 168 | 5/1993 | European Pat. Off. |
| 3542567 | 6/1986 | Germany. |
| 59-046252 | 3/1984 | Japan. |
| 59-048449 | 3/1984 | Japan. |
| 61-071830 | 4/1986 | Japan. |
| 2167759 | 6/1986 | United Kingdom. |
| 2200115 | 7/1988 | United Kingdom. |
| WO 90/07329 | 7/1990 | WIPO. |
| WO 91/00725 | 1/1991 | WIPO. |
| WO 91/18866 | 12/1991 | WIPO. |
| WO 92/08688 | 5/1992 | WIPO. |
| WO 92/08698 | 5/1992 | WIPO. |
| WO 92/08699 | 5/1992 | WIPO. |
| WO 92/08700 | 5/1992 | WIPO. |
| WO 92/08701 | 5/1992 | WIPO. |
| WO 92/17176 | 10/1992 | WIPO. |
| WO 93/23368 | 11/1993 | WIPO. |
| WO 93/23379 | 11/1993 | WIPO. |
| WO 93/23388 | 11/1993 | WIPO. |
| WO 94/04491 | 3/1994 | WIPO. |
| WO 94/04492 | 3/1994 | WIPO. |
| WO 94/04493 | 3/1994 | WIPO. |
| WO 94/10134 | 5/1994 | WIPO. |
| WO 94/10136 | 5/1994 | WIPO. |
| WO 94/18192 | 8/1994 | WIPO. |
| WO 94/19322 | 9/1994 | WIPO. |

OTHER PUBLICATIONS

R.D. Bindal et al., "Ab Initio Calculations on N–Methylmethanesulfonamide and Methyl Methanesulfonate for the Development of Force Field Torsional Parameters and Their Use in the Conformational Analysis of Some Novel Estrogens", *J. Am. Chem. Soc.*, 112, pp. 7861–7868 (1990).

R. Bone et al., "X–ray Crystal Structure of the HIV Protease Complex with L–700,417, an Inhibitor with Pseudo $C_2$ Symmetry", *J. Am. Chem. Soc.*, 113, pp. 9382–9384 (1991).

R.F. Borch et al., "The Cyanohydridoborate Anion as a Selective Reducing Agent", *J. Am. Chem. Soc.*, 93, pp. 2897–2904 (1971).

J.C. Craig et al., "Antiviral Synergy Between Inhibitors of HIV Proteinase and Reverse Transcriptase", *Antiviral Chem. and Chemotherapy*, 4(3), pp. 161–166 (1990).

(List continued on next page.)

*Primary Examiner*—Richard L. Raymond
*Attorney, Agent, or Firm*—Fish & Neave; James F. Haley, Jr.; Karen Mangasarian

[57] ABSTRACT

This invention provides a novel class of sulfonamide compounds of formula I which are aspartyl protease inhibitors:

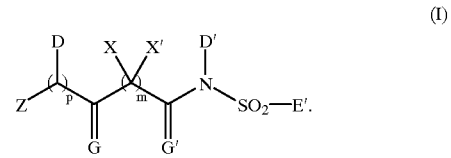

(I)

This invention also provides pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also provides methods for inhibition aspartyl protease activity and methods for treating viral infections using the compounds and compositions of this invention.

23 Claims, No Drawings

OTHER PUBLICATIONS

S. Crawford et al., "A Deletion Mutation in the 5' Part of the pol Gene of Moloney Murine Leukemia Virus Blocks Proteolytic Processing of the gag and pol Polyproteins", *J. Virol.*, 53, pp. 899–907 (1985).

M. Cushman et al., "Delvelopment of Methodology for the Synthesis of Stereochemically Pure Pheψ[CH$_2$N]Pro Linkages in HIV Protease Inhibitors", *J. Org. Chem.*, 56, pp. 4161–4167 (1991).

D.S. Dhanoa et al., "The Synthesis of Potent Macrocyclic Renin Inhibitors", *Tetrahedron Lett.*, 33, pp. 1725–1728 (1992).

G.B. Dreyer et al., "Hydroxyethylene Isostere Inhibitors of Human Immunodeficiency Virus–1 Protease: Structure–Activity Analysis Using Enzyme Kinetics, X–ray Crystallography, and Infected T–Cell Assays", *Biochemistry*, 31, pp. 6646–6659 (1992).

B.E. Evans et al., "A Stereocontrolled Synthesis of Hydroxyethylene Dipeptide Isosteres Using Novel, Chiral Aminoalkyl Epoxides and γ-(Aminoalkyl) γ-Lactones", *J. Org. Chem.*, 50, pp. 4615–4625 (1985).

G.A. Flynn et al., "An Acyl–Iminium Ion Cyclization Route to a Novel Conformationally Restricted Dipeptide Mimic: Applications to Angiotensin–Converting Enzyme Inhibition", *J. Am. Chem. Soc.*, 109, pp. 7914–7915 (1989).

G. Fontenot et al., "PCR Amplification of HIV–1 Proteinase Sequences Directly from Lab Isolates Allows Determination of Five Conserved Domains", *Virology*, 190, pp. 1–10 (1992).

P.G. Gassman and T.L. Guggenheim, "Opening of Epoxides with Trimethylsilyl Cyanide to Produce β–Amino Alcohols", *J. Am. Chem. Soc.*, 104, pp. 5849–5850 (1982).

E.E. Gilbert, "Recent Developments in Preparative Sulfonation and Sulfation", *Synthesis*, 1969, pp. 3–10 (1969).

A. Goldblum, "Modulation of the Affinity of Aspartic Proteases by the Mutated Residues in Active Site Models", *FEBS*, 261, pp. 241–244 (1990).

D. Grobelny et al., "Selective Phosphinate Transition–State Analogue Inhibitors of the Protease of Human Immunodeficiency Virus", *Biochem. Biophys. Res. Commun.*, 169, pp. 1111–1116 (1990).

G.D. Hartman et al., "4–Substituted Thiophene– and Furan–2–sulfonamides as Topical Carbonic Anhydrase Inhibitors", *J. Med. Chem.*, 35, pp. 3822–3831 (1992).

J.R. Huff, "HIV Protease: A Novel Chemotherapeutic Target for AIDS", *Journal of Medicinal Chemistry*, 34(8), pp. 2305–2314 (1991).

K.Y. Hui et al., "A Rational Approach in the Search for Potent Inhibitors Against HIV Proteinase", *FASEB*, 5, pp. 2606–2610 (1991).

N.E. Kohl et al., "Active HIV Protease Is Required for Viral Infectivity", *Proc. Natl. Acad. Sci. USA*, 85, pp. 4686–4690 (1988).

X. Lin et al., "Enzymic Activities of Two–Chain Pepsinogen, Two–Chain Pepsin, and the Amino–Terminal Lobe of Pepsinogen", *J. Biol. Chem.*, 267(24), pp. 17257–17263 (1992).

K.P. Manfredi et al., "Examination of HIV–1 Protease Secondary Structure Specificity Using Conformationally Constrained Inhibitors", *J. Med. Chem.*, 34, pp. 3395–3399 (1991).

F.R. Marshall, "Computer–Aided Drug Design", *Ann. Ref. Pharmacol. Toxicol.*, 27. pp. 193–213 (1987).

J.A. Martin, "Recent Advances in the Design of HIV Proteinase Inhibitors", *Antiviral Research*, 17, pp. 265–278 (1992).

T.D. Meek et al., "Inhibition of HIV–1 Protease in Infected T–Lymphocytes by Synthetic Peptide Analogues", *Nature*, 343, pp. 90–92 (1990).

M. Miller et al., "Structure of Complex of Synthetic HIV–1 Protease with a Substrate–Based Inhibitor at 2.3 Å Resolution", *Science*, 246, pp. 1149–1152 (1989).

M. Miller et al., "Crystal Structure of a Retroviral Protease Proves Relationship to Aspartic Protease Family", *Nature*, 337, pp. 576–579 (1989).

H. Mitsuya and S. Broder, "Inhibition of the in vitro Infectivity and Cytopathic Effect of Human T–Lymphotropic Virus Type III/Lymphoadenopathy–Associated Virus (HTLV–III/LAV) by 2',3'–Dideoxynucleosides", *Proc. Natl. Acad. Sci. USA*, 83, pp. 1911–1915 (1986).

K.H.M. Murthy et al., "Crystal Structures at 2.2–Å Resolution of Hydroxyethylene–Based Inhibitors Bound to Human Immunodeficiency Virus Type 1 Protease Show That the Inhibitors Are Present in Two Distinct Orientations", *J. Biol. Chem.*, 267, pp. 22770–22778 (1992).

J.B. Nichols et al., "A Molecular Mechanics Valence Force Field for Sulfonamides Derived by ab initio Methods", *J. Phys. Chem.*, 95, pp. 9803–9811 (1991).

L.E. Overman and L.A. Flippin, "Facile Aminolysis of Epoxides with Diethylaluminum Amides", *Tetrahedron Letters*, 195, pp. 195–198 (1981).

J. Palca, "Shooting at a New HIV Target", *Science*, 247, p. 410 (1990).

L.H. Pearl et al., "A Structural Model for the Retroviral Proteases", *Nature*, 329. pp. 329–351 (1987).

M. Popvic et al., "Detection, Isolation, and Continuous Production of Cytopathic Retroviruses (HTLV–III) from Patients with AIDS and Pre–AIDS", *Science*, 224, pp. 497–500 (1984).

G.H. Posner and D.Z. Rogers, "Organic Reactions at Alumina Surfaces. Mild and Selective Opening of Epoxides by Alcohols, Thiols, Benzeneselenol, Amines, and Acetic Acids", *J. Am. Chem. Soc.*, 99, 8208–18 (1977).

M.D. Power et al., "Nucleotide Sequence of SRV–1, a Type D Simian Acquired Immune Deficiency Syndrome Retrovirus" *Science*, 231, pp. 1567–1573 (1986).

N.A. Roberts, "Rational Design of Peptide–Based HIV Proteinase Inhibitors", *Science*, 248, pp. 358–361 (1990).

S. Scharpe et al., "Proteases and Their Inhibitors: Today and Tomorrow", *Biochimie*, 73, pp. 121–126 (1991).

S.K. Sharma et al., "Could Angiotensin I Be Produced from a Renin Substrate by the HIV–1 Protease?", *Anal. Biochem.*, 198, pp. 363–367 (1991).

H. Toh et al., "Close Structural Resemblance Between Putative Polymerase of a Drosophila Transposable Genetic Element 17.6 and pol Gene Product of Moloney Murine Leukemia Virus", *EMBO J.*, 4. pp. 1267–1272 (1985).

Baker et al., "An anitmalarial alkyloid from hydrangea. IV. Functional derivatives of 3–alkyl–4–quinazolones," *Journal of Organic Chemistry*, 17:1, pp. 35–51 (Jan. 1952).

Boon, W.R., "Respiratory stimulants. Part II. Fully substituted bisureas derived from 2.2'–diaminodiethyl ether and 1,3–diamino–2–alkoxypropanes," *Journal of the Chemical Society*, pp. 1378–1380 (1949).

Degutis et al., "Reactivity of 2–chloroethyl derivatives of aromatic diamines and aminosulphonic acids," *Chemical Abstracts*, 66:1, p. 198 (Jan. 2, 1967).

Goldenberg et al., "Synthèse de dérivés N–amino–3 hydroxy–2 propyl de N–sulfonylanilines. Étude de leur potentiel antiangineux," *European Journal of Medicinal Chemistry, Chimica Therapeutica,* 15:6, pp. 545–550 (1980).

Nair et al., "Folate analogues altered in the C9–N10 bridge region: N10–tosylisohofolic acid and N10–tosylisohomoaninopterin," *Journal of Medicinal Chemistry,* 21:7, pp. 673–677 (Jul. 1978).

SULFONAMIDE INHIBITORS OF ASPARTYL PROTEASE

CROSS-REFERENCE TO RELATED APPLICATIONS

This application is a 371 of PCT/US95/02420, filed Feb. 24, 1995, which is a continuation-in-part of U.S. patent application Ser. No. 08/207,580, filed Mar. 7, 1994, now abandoned.

TECHNICAL FIELD OF THE INVENTION

The present invention relates to a novel class of sulfonamides which are aspartyl protease inhibitors. In one embodiment, this invention relates to a novel class of HIV aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting. aspartyl protease activity and methods for treating viral infections using the compounds and compositions of this invention.

BACKGROUND OF THE INVENTION

The human immunodeficiency virus ("HIV") is the causative agent for acquired immunodeficiency syndrome ("AIDS")—a disease characterized by the destruction of the immune system, particularly of $CD4^+$ T-cells, with attendant susceptibility to opportunistic infections—and its precursor AIDS-related complex ("ARC")—a syndrome characterized by symptoms such as persistent generalized lymphadenopathy, fever and weight loss.

As in the case of several other retroviruses, HIV encodes the production of a protease which carries out post-translational cleavage of precursor polypeptides in a process necessary for the formation of infectious virions (S. Crawford et al., "A Deletion Mutation in the 5' Part of the pol Gene of Moloney Murine Leukemia Virus Blocks Proteolytic Processing of the gag and pol Polyproteins", *J. Virol.*, 53, p. 899 (1985)). These gene products include pol, which encodes the virion RNA-dependent DNA polymerase (reverse transcriptase), an endonuclease, HIV protease, and gag, which encodes the core-proteins of the virion (H. Toh et al., "Close Structural Resemblance Between Putative Polymerase of a Drosophila Transposable Genetic Element 17.6 and pol gene product of Moloney Murine Leukemia Virus", *EMBO J.*, 4, p. 1267 (1985); L. H. Pearl et al., "A Structural Model for the Retroviral Proteases", *Nature, pp.* 329–351 (1987); M. D. Power et al., "Nucleotide Sequence of SRV-1, a Type D Simian Acquired Immune Deficiency Syndrome Retrovirus", *Science,* 231, p. 1567 (1986)).

A number of synthetic anti-viral agents have been designed to target various stages in the replication cycle of HIV. These agents include compounds which block viral binding to $CD4^+$ T-lymphocytes (for example, soluble CD4), and compounds which interfere with viral replication by inhibiting viral reverse transcriptase (for example, didanosine and zidovudine (AZT)) and inhibit integration of viral DNA into cellular DNA (M. S. Hirsh and R. T. D'Aqulia, "Therapy for Human Immunodeficiency Virus Infection", *N. Eng. J. Med.,* 328, p. 1686 (1993)). However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, drug design efforts have been directed toward creating compounds which inhibit the formation of infectious virions by interfering with the processing of viral polyprotein precursors. Processing of these precursor proteins requires the action of virus-encoded proteases which are essential for replication (Kohl, N. E. et al. "Active HIV Protease is Required for Viral Infectivity" *Proc. Natl. Acad. Sci. USA,* 85, p. 4686 (1988)). The anti-viral potential of HIV protease inhibition has been demonstrated using peptidal inhibitors. Such peptidal compounds, however, are typically large and complex molecules that tend to exhibit poor bioavailability and are not generally consistent with oral administration. Accordingly, the need still exists for compounds that can effectively inhibit the action of viral proteases, for use as agents for preventing and treating chronic and acute viral infections. Such agents would be expected to act as effective therapeutic agents in their own right. In addition, since they act at a separate stage in the virus life cycle from previously described antiretroviral agents, the administration of a combination of agents would be expected to result in increased therapeutic efficacy.

SUMMARY OF THE INVENTION

The present invention provides a novel class of compounds, and pharmaceutically acceptable derivatives thereof, that are useful as inhibitors of aspartyl proteases, and in particular, HIV aspartyl protease. These compounds can be used alone or in combination with other therapeutic or prophylactic agents, such as anti-virals, antibiotics, immunomodulators or vaccines, for the treatment or prophylaxis of viral infection.

According to a preferred embodiment, the compounds of this invention are capable of inhibiting HIV viral replication in human $CD_4^+$ cells including T-cells, monocytic lines including macrophages and dendrocytes and other permissive cells. These compounds are useful as therapeutic and prophylactic agents to treat or prevent infection by HIV-1 and related viruses which may result in asymptomatic infection, AIDS-related complex ("ARC"), acquired immunodeficiency syndrome ("AIDS"), or similar disease of the immune system.

It is a principal object of this invention to provide a novel class of sulfonamides that are aspartyl protease inhibitors, and particularly, HIV aspartyl protease inhibitors. This novel class of sulfonamides is represented by formulas I and II:

Formula I:

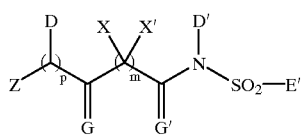
(I)

Formula II:

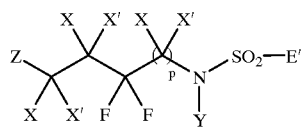

(II)

wherein:
each Z is selected from the group consisting of —N(D)SO$_2$E; —N(H)A; —N(D)A; —N(H)E; —N(H)C(O)N(D)(E); N(HTHt; —Ht and —N(D)—Ht;

each A is independently selected from the group consisting of H; Ht; R$^1$—Ht; —R$^1$—C$_1$–C$_6$ alkyl, which may be optionally substituted with one or more groups selected from the group consisting of hydroxy, C$_1$–C$_4$ alkoxy, Ht, —O—Ht, —NR$^2$—CO—N(R$^2$) (R$^2$), —NR$^2$—CO—OR$^2$ and —CO—N(R$^2$) (R$^2$); and —R$^1$—C$_2$–C$_6$ alkenyl, which may be optionally substituted with one or more groups selected from the group consisting of hydroxy, C$_1$–C$_4$ alkoxy, Ht, —D—Ht, —NR$^2$—CO—N(R$^2$) (R$^2$) and —CO—N(R$^2$) (R$^2$);

each Ht is independently selected from the group consisting of C$_3$–C$_7$ cycloalkyl; C$_5$–C$_7$ cycloalkenyl; C$_6$–C$_{10}$ aryl; phenyl fused with heterocycle; and heterocycle; wherein any member of said Ht may be optionally substituted with one or more substituents selected from the group consisting of oxo, —OR$^2$, —R$^2$, —N(R$^2$) (R$^2$), —NHOH, —R$^2$—OH, —CN, —CO$_2$R$^2$, —C(O)—N(R$^2$)(R$^2$), —S(O)$_2$—N(R$^2$) (R$^2$), —N(R$^2$)—C(O)—R$^2$, —C(O)—R$^2$, —S(O)$_n$—R$^2$, —OCF$_3$, —S(O)$_n$—D, —N(R$^2$)—S(O)$_2$(R$^2$), halo, —CF$_3$, —NO$_2$, —R$^6$, —O—R$^6$, —C(O)N(D)(D) and —C(O)N(H)D;

each D and D' is independently selected from the group consisting of R$^6$; —N(R$^2$) (R$^2$); C$_1$–C$_6$ alkyl, which may be optionally substituted with one or more groups selected from C$_3$–C$_6$ cycloalkyl, —OR$^2$, —R$^3$, —O—R$^6$—S—R$^6$ and R$^6$; C$_2$–C$_4$ alkenyl, which may be optionally substituted with one or more groups selected from the group consisting of C$_3$–C$_6$ cycloalkyl, —OR$^2$, —R$^3$, —O—R$^6$ and R$^6$; C$_3$–C$_6$ cycloalkyl, which may be optionally substituted with or fused with R$^6$; and C$_5$–C$_6$ cycloalkenyl, which may be optionally substituted with or fused with R$^6$;

each E and E' is independently selected from the group consisting of Ht; —O—Ht; Ht—Ht; —O—R$^3$; —NR$^2$R$^3$; C$_1$–C$_6$ alkyl, which may be optionally substituted with one or more groups selected from the group consisting of R$^4$ and Ht; and C$_2$–C$_6$ alkenyl, which may be optionally substituted with one or more groups selected from the group consisting of R$^4$ and Ht;

each R$^1$ is independently selected from the group consisting of —C(O)—, —S(O)$_2$—, —C(O)—C(O)—, —O—C(O)—, —O—S(O)$_2$, —NR$^2$—S(O)$_2$—, —NR$^2$—C(O)— and —NR$^2$—C(O)—C(O)—;

each R$^2$ is independently selected from the group consisting of H, —R$^6$, and C$_1$–C$_4$ alkyl optionally substituted with R$^6$;

each R$^3$ is independently selected from the group consisting of H, Ht, C$_1$–C$_6$ alkyl and C$_2$–C$_6$ alkenyl wherein any member of said R$^3$, except H, may be optionally substituted with one or more substituents selected from the group consisting of —OR$^2$, —C(O)—NH—R$^2$, —S(O)$_n$—N(R$^2$) (R$^2$), Ht, —CN, —SR$^2$, —CO$_2$R$^2$, NR$^2$—C(O)—R$^2$;

each R$^4$ is independently selected from the group consisting of —OR$^2$, —C(O)—NHR$^2$, —S(O)$_2$—NHR$^2$, halo, —NR$^2$—C(O)—R$^2$, —CN, —N(R$^2$)(R$^2$), —NO$_2$, —C(O)N(D)(D) and —C(O)N(H)D;

each R$^5$ is independently selected from the group consisting of H and C$_1$–C$_3$ alkyl;

each R$^6$ is independently selected from the group consisting of aryl, carbocycle and heterocycle, wherein said carbocycle or heterocycle may be optionally substituted with one or more groups selected from the group consisting of oxo, —OR$^5$, —R$^5$, —N(R$^5$)(R$^5$), —N(R$^5$)—C(O)—R$^5$, —R$^5$—OH, —CN, —CO$_2$R$^5$, —C(O)—N(R$^5$)(R$^5$), halo and —CF$_3$;

each n is independently 1 or 2;

m is an integer selected from 1, 2 and 3;

p is an integer selected from 0 and 1;

each G and G' is independently selected from the group consisting of H$_2$ and O;

each X and X' is independently selected from the group consisting of hydrogen; —OH; —NH$_2$; —SH; D; halogen and, if X and X' are taken together, oxygen; and each Y is independently selected from the group consisting of hydrogen and D.

It is also an object of this invention to provide pharmaceutical compositions comprising the sulfonamides of formulas I and II, methods for preparing those sulfonamides, and methods for their use as inhibitors of aspartyl protease, and particularly, HIV aspartyl protease.

It is a further object of this invention to provide methods for treating viral diseases, and in particular HIV-related diseases, using the compounds and compositions of this invention.

DETAILED DESCRIPTION OF THE INVENTION

In order that the invention herein described may be more fully understood, the following detailed description is set forth. In the description, the following abbreviations are used:

| Designation | Reagent or Fragment |
| --- | --- |
| Ac | acetyl |
| Me | methyl |
| Et | ethyl |
| Bn | benzyl |
| Trityl | triphenylmethyl |
| Asn | D- or L-asparagine |
| Ile | D- or L-isoleucine |
| Phe | D- or L-phenylalanine |
| Val | D- or L-valine |
| Boc | tert-butoxycarbonyl |
| Cbz | benzyloxycarbonyl (carbobenzyloxy) |
| Fmoc | 9-fluorenylmethoxycarbonyl |
| DCC | dicyclohexylcarbodiimide |
| DIC | diisopropylcarbodiimide |
| EDC | 1-(3-dimethylaminopropyl)-3-ethylcarbodiimide hydrochloride |
| HOBt | 1-hydroxybenzotriazole |
| HOSu | 1-hydroxysuccinimide |
| TFA | trifluoroacetic acid |
| DIEA | diisopropylethylamine |
| DBU | 1,8-diazabicyclo(5.4.0)undec-7-ene |

| Designation | Reagent or Fragment |
| --- | --- |
| EtOAc | ethyl acetate |
| t-Bu | tert-butyl |
| iBu | iso-butyl |
| DMF | dimethylformamide |
| THP | tertrahydropyran |
| THF | tetrahydrofuran |
| DMSO | dimethylsulfoxide |

The following terms are employed herein:

Unless expressly stated to the contrary, the terms "—SO$_2$—" and "—S(O)$_2$—" as used herein refer to a sulfone or sulfone derivative (i.e., both appended groups linked to the S), and not a sulfinate ester.

The term "alkoxy" refers to an alkyl ether radical, wherein the term "alkyl" is as defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "alkyl", alone or in combination with any other term, refers to a straight-chain or branch-chain saturated aliphatic hydrocarbon radical containing the specified number of carbon atoms, or where no number is specified, preferably from 1–10 and more preferably from 1–5 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, preferably from 2–10 carbon atoms and more preferably, from 2–6 carbon atoms. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "anti-viral agent" or "anti-retroviral agent" refers to a compound or drug which possesses viral inhibitory activity. Such agents include reverse transcriptase inhibitors (including nucleoside and non-nucleoside analogs) and protease inhibitors. Preferably the protease inhibitor is an HIV protease inhibitor. Examples of nucleoside analog reverse transcriptase inhibitors include, but are not limited to, zidovudine (AZT), dideoxycytidine (ddC), didanosine (ddI), stavudine (d4T), 3TC, 935U83, i592U89 and 524W91. Examples of non-nucleoside analog reverse transcriptase inhibitors include, but are not limited to TIBO, delavirdine (U90) and nevirapine. Examples of HIV protease inhibitors include, but are not limited to, saquinavir (Ro 31-8959), L-735,524, ABT 538 (A80538), AG 1341, XM 412, XM 450, BMS 186318 and CPG 53,437.

The term "aryl", alone or in combination with any other term, refers to a carbocyclic aromatic radical (such as phenyl or naphthyl) containing the specified number of carbon atoms, preferably from 6–14 carbon atoms, and more preferably from 6–10 carbon atoms. Examples of aryl radicals include, but are not limited to phenyl, naphthyl, indenyl, indanyl, azulenyl, fluorenyl, anthracenyl and the like.

The term "backbone" refers to the structural representation of a compound of this invention, as set forth in the figures drawn in this application.

The term "carbocycle" refers to a non-aromatic stable 3- to 8-membered carbon ring which may be saturated, mono-unsaturated or poly-unsaturated. The carbocycle may be attached at any endocyclic carbon atom which results in a stable structure. Preferred carbocycles have 5–6 carbons.

The term "heterocycle", unless otherwise defined herein, refers to a stable 3–7 membered monocyclic heterocyclic ring or 8–11 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. In addition, any ring nitrogen or carbon may be optionally substituted with a substituent R$^2$, as defined herein for compounds of formula I or II. A heterocycle may be attached at any endocyclic carbon or heteroatom which results in the creation of a stable structure. Preferred heterocycles include 5–7 membered monocyclic heterocycles and 8–10 membered bicyclic heterocycles. Preferred heterocycles defined above include, for example, benzimidazolyl, imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, S-carbolinyl, tetrazolyl, thiazolidinyl, benzofuranoyl, thiamorpholinyl sulfone, oxazolyl, benzoxazolyl, oxopiperidinyl, oxopyrroldinyl, oxoazepinyl, azepinyl, isoxazolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetrahydrofurofuranyl and tetrahydropyranofuranyl.

The term "halo" refers to a radical of fluorine, chlorine, bromine or iodine.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "substituted", whether preceded by the term "optionally" or not, and substitutions contained in formulas of this invention, refer to the replacement of one or more hydrogen radicals in a given structure with the radical of a specified substituent. When more than one position in a given structure may be substituted with more than one substituent selected from a specified group, the substituents may be either the same or different at every position (for example, the moiety —N(R$^2$)(R$^2$) or -phenyl-R$^7$). Typically, when a structure may be optionally substituted, 0–3 substitutions are preferred, and 0–1 substitutions is more preferred. Most preferred substituents are those which enhance protease inhibitory activity or intracellular antiviral activity in permissive mammalian cells or immortalized mammalian cell lines, or which enhance deliverability by enhancing solubility characteristics or enhancing pharmacokinetic or pharmacodynamic profiles as compared to the unsubstituted compound. Other more preferred substituents include those used in the compounds shown in Tables 1–8 and the most preferred substituents include those used in the compounds in Tables 1, 5, 6, and 7.

The term "$R^2$" when used as a linker between two radicals excludes $R^2$ as H.

The term "-phenyl-$R^7$" as used herein refers to a phenyl radical having $R^7$, the same or different, at each free position and expressly envisions polycyclic ring systems formed by joining multiple $R^7$ substituents on the phenyl ring. Preferably, 0–3 $R^7$ in a particular phenyl radical are not H. In addition to H, —OH, —OCH$_3$, —NH$_2$, —NO$_2$ and CN are preferred $R^7$. Such ring systems are preferably mono- or bi-cyclic. These ring systems may be carbocyclic or may optionally contain one or more heteroatoms, such as N, O or S. Preferred ring systems include benzimidazolyl, benzoxazolyl, benzothiazolyl, benztriazolyl, imidazolyl, indolyl, isoxazolyl, isothiazolyl, oxazolyl, thianaphthenyl, thiazolyl, and triazolyl.

The term "pharmaceutically effective amount" refers to an amount effective in treating HIV infection in a patient either as monotherapy or in combination with other agents. The term "treating" as used herein refers to the alleviation of symptoms of a particular disorder in a patient or the improvement of an ascertainable measurement associated with a particular disorder. Specifically, with respect to HIV, effective treatment using the compounds and compositions of this invention would result in an improvement in an HIV associated ascertainable measurement. The term "prophylactically effective amount" refers to an amount effective in preventing HIV infection in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiretroviral agent.

As used herein, the compounds of this invention, including the compounds of formula I and II are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and N-($C_{1-4}$ alkyl)$_4^+$ salts.

The term "thiocarbamates" refers to compounds containing the functional group N—SO$_2$—O.

The term "if X and X' are taken together, oxygen" refers to a carbonyl formed on the carbon that bears that X and X'. When X and X' are both geminal substitutents on the same carbon, if one is —OH the other is H.

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

The compounds of the present invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The sulfonamides of this invention are those of formulas I and II:

Formula I:

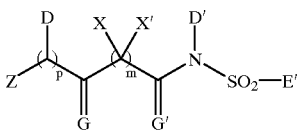

(I)

Formula II:

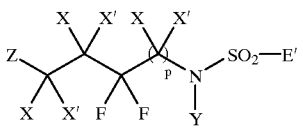

(II)

wherein:
- each Z is selected from the group consisting of —N(D)SO$_2$E; —N(H)A; —N(D)A; —N(H)E; —N(H)C(O)N(D)(E); —N(H)—Ht; —Ht and —N(D)—Ht;
- each A is independently selected from the group consisting of H; Ht; —R$^1$—Ht; —R$^1$—C$_1$–C$_6$ alkyl, which may be optionally substituted with one or more groups selected from the group consisting of hydroxy, C$_1$–C$_4$ alkoxy, Ht, —O—Ht, —NR$^2$—CO—N(R$^2$) (R$^2$), —NR$^2$—CO—OR$^2$ and —CO—N(R$^2$) (R$^2$) ; and —R$^1$—C$_2$–C$_6$ alkenyl, which may be optionally substituted with one or more groups selected from the group consisting of hydroxy, C$_1$–C$_4$ alkoxy, Ht, —O—Ht, —NR$^2$—CO—N(R$^2$) (R$^2$) and —CO—N(R$^2$) (R$^2$);
- each Ht is independently selected from the group consisting of C$_3$–C$_7$ cycloalkyl; C$_5$–C$_7$ cycloalkenyl; C$_6$–C$_{10}$ aryl; phenyl fused with heterocycle; and heterocycle; wherein any member of said Ht may be optionally substituted with one or more substituents selected from the group consisting of oxo, —OR$^2$, —R$^2$, —N(R$^2$) (R$^2$), —NHOH, —R$^2$—OH, —CN, —CO$_2$R$^2$, —C(O)—N(R$^2$) (R$^2$), —S(O)$_2$—N(R$^2$) (R$^2$), —N(R$^2$)—C(O)—R$^2$, —C(O)—R$^2$, —S(O)$_n$—R$^2$, —OCF$_3$, —S(O)$_n$—D, —N(R$^2$)—S(O)$_2$(R$^2$), halo, —CF$_3$, —NO$_2$, —R$^6$, —O—R$^6$, —C(O)N(D)(D) and —C(O)N(H)D;
- each D and D' is independently selected from the group consisting of R$^6$; —N(R$^2$) (R$^2$); C$_1$–C$_6$ alkyl, which may be optionally substituted with one or more groups selected from C$_3$–C$_6$ cycloalkyl, —OR$^2$, —R$^3$, —O—R$^6$, —S—R$^6$ and R$^6$; C$_2$–C$_4$ alkenyl, which may be optionally substituted with one or more groups selected from the group consisting of C$_3$–C$_6$ cycloalkyl, —OR$^2$, —R$^3$, —O—R$^6$ and R$^6$; C$_3$–C$_6$ cycloalkyl, which may be optionally substituted with or fused with R$^6$; and C$_5$–C$_6$ cycloalkenyl, which may be optionally substituted with or fused with R$^6$;
- each E and E' is independently selected from the group consisting of Ht; —O—Ht; Ht—Ht; —O—R$^3$; —NR$^2$R$^3$; C$_1$–C$_6$ alkyl, which may be optionally substituted with one or more groups selected from the group consisting of R$^4$ and Ht; and C$_2$–C$_6$ alkenyl, which may be optionally substituted with one or more groups selected from the group consisting of R$^4$ and Ht;
- each R$^1$ is independently selected from the group consisting of —C(O)—, —S(O)$_2$—, —C(O)—C(O)—, —O—C(O)—, —O—S(O)$_2$, —NR$^2$—S(O)$^2$—, —NR$^2$—C(O)— and —NR$^2$—C(O)—C(O)—;
- each R$^2$ is independently selected from the group consisting of H, R$^6$, and C$_1$–C$_4$ alkyl optionally substituted with R$^6$;
- each R$^3$ is independently selected from the group consisting of H, Ht, C$_1$–C$_6$ alkyl and C$_2$–C$_6$ alkenyl wherein any member of said R$^3$, except H, may be optionally substituted with one or more substituents selected from the group consisting of —OR$^2$, —C(O)—NH—R$^2$, —S(O)$_n$—N(R$^2$) (R$^2$) , Ht, —CN, —SR$^2$, —CO$_2$R$^2$, NR$^2$—C(O)—R$^2$;
- each R$^4$ is independently selected from the group consisting of —OR$^2$, —C(O)—NHR$^2$, —S(O)$_2$—NHR$^2$, halo, —NR$^2$—C(O)—R$^2$, —CN, —N(R$^2$) (R$^2$), —NO$_2$, —C(O)N(D)(D) and —C(O)N(H)D;
- each R$^5$ is independently selected from the group consisting of H and C$_1$–C$_3$ alkyl;
- each R$^6$ is independently selected from the group consisting of aryl, carbocycle and heterocycle, wherein said carbocycle or heterocycle may be optionally substituted with one or more groups selected from the group consisting of oxo, —OR$^5$, —R$^5$, —N(R$^5$) (R$^5$), —N(R$^5$)—C(O)—R$^5$, —R$^5$—OH, —CN, —CO$_2$R$^5$, —C(O)—N(R$^5$)(R$^5$), halo and —CF$_3$;
- each n is independently 1 or 2;
- m is an integer selected from 1, 2 and 3;
- p is an integer selected from 0 and 1;
- each G and G' is independently selected from the group consisting of H$_2$ and 0;
- each X and X' is independently selected from the group consisting of hydrogen; —OH; —NH$_2$; —SH; D; halogen and, if X and X' are taken together, oxygen;
- each Y is independently selected from the group consisting of hydrogen and D.

Except where expressly noted to the contrary, the term "[variable] as defined for formula I or II", or any equivalent term used herein, refers to the definitions shown directly above. In addition, where no reference is made to a particular definition for a given variable, the definition is to be taken as that defined for formulas I and II shown directly above.

Preferred compounds of formula I include those compounds wherein G or G' or both are oxygen. More preferably, when G or G' or both are oxygen (i.e, form a carbonyl with the carbon to which they are attached), the X and X' on the carbon adjacent to the carbonyl are independently selected from the group consisting of H, OH, F, or taken together, oxygen. Preferably, the compounds of formula I contain from 1 to 4 carbonyls, and more preferably 1 to 3 carbonyls, in the backbone of the structures.

Other preferred compounds of formula I and II are those wherein E' is selected from Ht and —R$^2$—Ht. More preferred E' are those selected from the group consisting of -phenyl-R$^7$; carbocycle; heterocycle optionally substituted with —NHAc, alkyl, alkoxy, —OH, and CF$_3$; and C$_1$–C$_6$ alkyl optionally substituted with Ht wherein Ht may be optionally substituted with —NH— C(O)—C$_1$–C$_3$ alkyl, oxo, C$_1$–C$_6$ alkyl, alkoxy, —OH, and CF$_3$ and wherein R$^7$ is selected from the group consisting of H, —OH, —OR$^2$, R$^2$, —N(R$^2$) (R$^2$), —N(R$^2$)—C(O)—R$^2$, —R$^2$—OH, —CN, —CO$_2$R$^2$, —C(O)—N(R$^2$)(R$^2$), —NO$_2$, halo and —CF$_3$. Most preferred E' are those selected from the group -phenyl-R$^7$. Preferred R$^7$ are selected from the group consisting of H, —OH, —OR$^2$, —R$^2$, —N(R$^2$) (R$^2$), —N(R$^2$)—C(O)—R$^2$, and —NO$_2$. Most preferred R$^7$ are —NH$_2$, —OH and —OCH$_3$. Unless expressly noted to the contrary, the term "R$^7$" refers to the definitions shown above.

Other preferred compounds of formula I include those compounds having the structures of formulas IV, VI, VII, C and CI:

Formula IV:

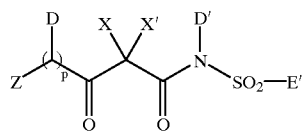

(IV)

Formula VI:

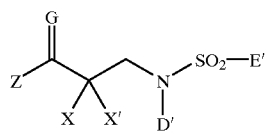

(VI)

Formula VII:

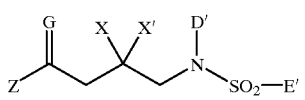

(VII)

Formula C:

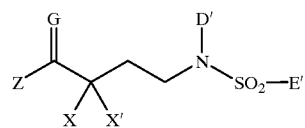

(C)

Formula CI:

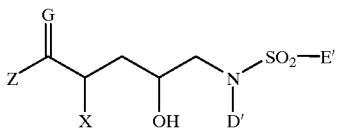

(CI)

wherein the variables are as defined for the compounds of formula I with the exception that in formula C, Z is selected from the group consisting of —N(H)A; —N(D)A; —N(H)E; —N(H)C(O)N(D)(E); —N(H)—Ht; —Ht and —N(D)—Het. The most preferred compounds of formula I are those compounds of formulas VI, VII, and C.

Preferred compounds of formula IV include those compounds having the following definitions for one or more of the below-specified variables:

each D and D' is independently selected from the group consisting of C$_1$–C$_6$ alkyl, which may be optionally substituted with R$^6$;

each E and E' is independently selected from C$_5$–C$_6$ aryl, which may be optionally substituted with R$^4$;

each R$^4$ is independently selected from the group consisting of —OR$^2$, —N(R$^2$) (R$^2$) and —NO$_2$;

each Z is independently selected from the group consisting of —N(H)Ht; —N(H)A; —N(D)A and —Ht;

each Ht is independently selected from the group consisting of C$_6$–C$_{10}$ aryl and 5–10 membered saturated or unsaturated heterocycle, wherein any member of said Ht may be optionally substituted with one or more substituents, the same or different, selected from the group consisting of —OR$^2$, R$^2$, —N(R$^2$) (R$^2$), —NO$_2$, —C(O)N(R$^2$) (R$^2$) and —S(O)$_n$—R$^6$;

each X and X' is independently selected from the group consisting of H, —OH and, most preferably, if X and X' are taken together, oxygen;

each A is independently selected from the group consisting of H; —R$^1$—Ht and —R$^1$—C$_1$–C$_6$ alkyl; and each R$^1$ is independently selected from the group consisting of —C(O)— and —O—C(O)—.

Preferred compounds of formula VI include those compounds having the following definitions for one or more of the below-identified variables:

each D and D' is independently selected from the group consisting of C$_1$–C$_6$ alkyl, which may be optionally substituted with R$^6$;

each X and X' is independently selected from the group consisting of H, OH, and if X and X' are taken together, oxygen;

each E' is independently selected from C$_5$–C$_6$ aryl, which may be optionally substituted with R$^4$;

each R$^1$ is selected from the group consisting of —C(O)— and —O—C(O)—;

each R$^4$ is independently selected from the group consisting of —OR$^2$, —N(R$^2$) (R$^2$) and —NO$_2$;

each Z is selected from the group consisting of —N(H)Ht; —N(H)A; —N(D)A and —Ht;

each Ht is independently selected from the group consisting of C$_6$–C$_{10}$ aryl and 5–10 membered saturated or unsaturated heterocycle, and wherein any member of said Ht may be optionally substituted with one or more substituents, the same or different, selected from the group consisting of —OR$^2$, R$^2$, —N(R$^2$) (R$^2$), —NO$_2$, —C(O)N(R$^2$) (R$^2$) and —S(O)$_n$—R$^6$; and each A is selected from the group consisting of H; —R$^1$—Ht and —R$^1$—C$_1$–C$_6$ alkyl.

Other preferred compounds of formula VI include those compounds of formula CIII:

Formula CIII:

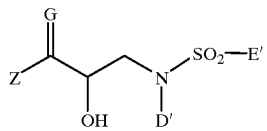

(CIII)

wherein the variables are defined as above for the compounds of formula I. Preferred compounds of formula CIII include those compounds having one or more variables as defined for preferred compounds of formula VI. In addition, preferred compounds of formula CIII include those compounds having the formula LVIIa:

Formula LVIIa:

(LVIIa)

$$\underset{A}{\overset{D}{N}}\underset{}{\overset{OH}{\underset{}{\bigwedge}}}\underset{SO_2-E'}{\overset{D'}{N}}$$

wherein A is selected from the group consisting of —R¹—Ht and —R¹—$C_1$-$C_6$ alkyl substituted with —N($R^2$)—CO—N($R^2$) ($R^2$) or —N($R^2$)—CO—O—$R^2$; $R^1$ is selected from the group consisting of —C(O)— and —O—C(O)—; and the other variables are defined as above for the compounds of formula I. For compounds of formula LVIIa, preferred definitions for A include —$R^1$-phenyl-$R^7$, —$R^1$-heterocycle and —Val—$R^1$—$R^2$. More preferred definitions for A include:

[chemical structures]

Preferred D and D' for compounds of formula LVIIa include $C_1$-$C_6$ alkyl, which may be optionally substituted with $R^6$.

Preferred compounds of formula CIII also include those compounds having the formula LVIIb:

Formula LVIIb:

(LVIIb)

$$Z\underset{}{\overset{OH}{\bigwedge}}\underset{SO_2-E'}{\overset{D'}{N}}$$

wherein Z is selected from the group consisting of:

[chemical structures]

and wherein $R^8$ is selected from the group consisting of $R^2$, —N—C(O)—O—$R^2$ and —N—C(O)—$R^2$; $R^9$ is selected from the group consisting of $R^2$, —C(O)—O—$R^2$ and —C(O)—$R^2$ and $R^2$ is as defined above for compounds of formula I.

For compounds of formula LVIIb, preferred D and D' are $C_1$-$C_6$ alkyl which may be optionally substituted with $R^6$.

Preferred compounds of formula VII include those compounds having the following definitions for one or more of the below-specified variables:

each D and D' is $C_1$-$C_6$ alkyl, which may be optionally substituted with $R^6$;

G is $H_2$;

each X and X' is independently selected from the group consisting of H, OH, and if X and X' are taken together, oxygen;

each E' is independently selected from $C_5$-$C_6$ aryl, which may be optionally substituted with $R^4$;

each $R^1$ is selected from the group consisting of —C(O)— and —O—C(O)—;

each $R^4$ is independently selected from the group consisting of —$OR^2$, —N($R^2$) ($R^2$) and —$NO_2$;

each Z is selected from the group consisting of —N(H)Ht; —N(H)A; —N(D)$SO_2$E; —N(D)A and —Ht; and more preferably from either —N(D)$SO_2$E or —N(H)Ht;

each Ht is independently selected from the group consisting of $C_6$-$C_{10}$ aryl and 5–10 membered saturated or unsaturated heterocycle, and wherein any member of said Ht may be optionally substituted with one or more substituents, the same or different, selected from the group consisting of —OR², R², —N(R²) (R²), —NO₂, —C(O)N(R²) (R²) and —S(O)ₙ—R⁶ ; and each A is selected from the group consisting of H; —R¹—Ht and —R¹—C₁-C₆ alkyl.

Other preferred compounds of formula VII are those compounds having the structure of formula CIV:

Formula CIV:

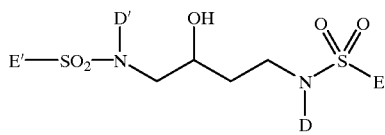

(CIV)

wherein the variables are defined as above for the compounds of formula VII.

Still other preferred compounds of formula VII are those compounds having the structure of formula LXII:

Formula LXII:

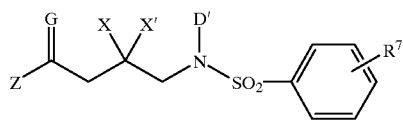

(LXII)

wherein the variables are defined as above for compounds of formula I and R⁷ is selected from the group consisting of H, —OH, —OR², —R², —N(R²) (R²), —N(R²)—C(O)—R², —R²—OH, —CN, —CO₂R², —C(O)—N(R²)(R²), halo and —CF₃. Preferred compounds of formula LXII include those compounds having one or more variables as defined for preferred compounds of formula VII.

Preferred compounds of formula C include those compounds having each Z is selected from the group consisting of —N(H)Ht; —N(H)A; —N(D)A and —Ht; and one or more variables as defined for preferred compounds of formula VI.

More preferred compounds of formula C include those compounds wherein G is H₂, X is —OH or H, and X' is —OH or H.

Preferred compounds of formula CI include those compounds wherein X is a C₁ alkyl substituted with R⁶ and D' is a C₁-C₄ alkyl optionally substituted with R⁶. Most preferably, X is benzyl and D' is i-Bu or cyclopentylmethyl.

Preferred compounds of formula II include those compounds wherein X and X' on the carbon adjacent to the backbone carbon bearing Z, taken together, are oxygen. Other preferred compounds of formula II are those compounds having the structure of formula VIII:

Formula VIII:

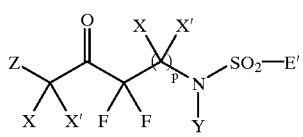

(VIII)

wherein the variables are as defined above for compounds of formula II.

Preferred compounds of formula VIII include those compounds wherein one or more of the variables are defined as follows: on the backbone carbon bearing Z, X is H and X' is D; on the backbone carbon adjacent to N—Y, X and X' are independently selected from D, and preferably from C₁-C₆ alkyl and H, and most preferably both are H; Y is selected from D, preferably from C₁-C₆ alkyl and H; and E is a C₆-C₁₀ aryl optionally substituted with one or two substituents, the same or different, selected from —OH, —OCH₃ and —NH₂ and Z is selected from (3S)—THF—OC(O)NH— or 5-(1,3-dioxanyl)—OC(O)NH—.

Other preferred compounds of formula VIII are those compounds having the structure of formula CV:

Formula CV:

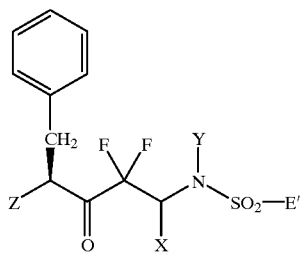

(CV)

wherein the variables are as defined above for compounds of formula II. Preferred compounds of formula CV include those compounds where X and Y are independently selected from the group consisting of H or C₁-C₆ alkyl, which may be optionally substituted with R⁶; and Z is selected from the group consisting of —N(H)(A) or —N(D)(A).

Preferred sulfonamides of this invention of formulas I and II include the specific compounds contained in Tables 1 through 8. Preferred compounds are those which appear in Tables 1, 5, 6, and 7. Although particular —phenyl-R⁷ variables are specified in these tables, this invention expressly encompasses the specific compounds shown having any -phenyl-R⁷, as defined above. In such compounds, preferably, at least three, and more preferably four, of the R⁷ substituents are H.

The following list summarizes the content of each Table:

Table 1: preferred compounds of Formula CIII
Table 2: preferred compounds of Formula LVIIb
Table 3: preferred compounds of Formula CV
Table 4: preferred compounds of Formula IV
Table 5: preferred compounds of Formula LXII
Table 6: preferred compounds of Formula CIV
Table 7: preferred compounds of Formula C
Table 8: preferred compounds of Formula CI

TABLE 1

| COMPOUND | OH | Z | G | D' | R⁷ |
|---|---|---|---|---|---|
| XVI | R,S | t-Bu-NH-CO-[(3-pyridylmethyl)-4-methylpiperazinyl] | H$_2$ | i-Bu | 4-OCH$_3$ |
| XVII | R,S | t-Bu-NH-CO-(N-methylthiazolidinyl) | H$_2$ | i-Bu | 4-OCH$_3$ |
| XVIII | R,S | t-Bu-NH-CO-(N-methylthiazolidinyl) | O | i-Bu | 4-OCH$_3$ |
| XIX | R,S | (2-hydroxy-indanyl)NH- | H$_2$ | i-Bu | 4-OCH$_3$ |
| XX | R,S | t-Bu-NH-CO-(2-methylphenyl) | H$_2$ | i-Bu | 4-OCH$_3$ |
| XXI | R,S | (tetrahydrofuran-3-yl)-O-CO-N(CH$_3$)(CH$_2$Ph) | | H$_2$ | 4-OCH$_3$, cyclopentylmethyl |
| LXV | R,S | (1,3-dioxan-5-yl)-O-CO-N(CH$_3$)(CH$_2$Ph) | | H$_2$ | 4-OCH$_3$, cyclopentylmethyl |

TABLE 1-continued

| COMPOUND | OH | Z | G | D' | R⁷ |
|---|---|---|---|---|---|
| XXII | R,S | t-Bu—NH—C(O)—N(CH₂-phenyl)— | H₂ | —CH₂-cyclopentyl | 4-OCH₃ |
| 1000 | R | (tetrahydrofuran-3-yl)-O-C(O)-N(CH₃)(CH₂)₂-phenyl | H₂ | —CH₂-cyclopentyl | 4-OCH₃ |
| 1001 | S | (tetrahydrofuran-3-yl)-O-C(O)-N(CH₃)(CH₂)₂-phenyl | H₂ | —CH₂-cyclopentyl | 4-OCH₃ |
| XXIV | R,S | phenyl-SO₂—N(CH₃)(CH₂)₂-phenyl | H₂ | —CH₂-cyclopentyl | 4-OCH₃ |
| 1002 | R,S | t-Bu—NH—C(O)—(2-NH-phenyl)— | H₂ | i-Bu | 4-OCH₃ |

TABLE 1-continued

| COMPOUND | OH | Z | G | D' | R⁷ |
|---|---|---|---|---|---|
| 1003 | S | (1,3-dioxolan-2-yl)methyl N-isopentyl-N-methylcarbamate | $H_2$ | cyclopentylmethyl | 4-OCH₃ |
| 1004 | S | (tetrahydrofuran-3-yl) N-isobutyl-N-methylcarbamate | $H_2$ | cyclopentylmethyl | 4-OCH₃ |
| 1005 | S | (1,3-dioxan-5-yl) N-(2-phenylethyl)-N-methylcarbamate | $H_2$ | cyclopentylmethyl | 4-OCH₃ |
| 1006 | S | (tetrahydrofuran-3-yl) N-(3-phenylpropyl)-N-methylcarbamate | $H_2$ | cyclopentylmethyl | 4-OCH₃ |
| 1007 | S | (tetrahydrofuran-3-yl) N-(2-phenylethyl)-N-methylcarbamate | $H_2$ | cyclopentylmethyl | 4-OH |

TABLE 1-continued
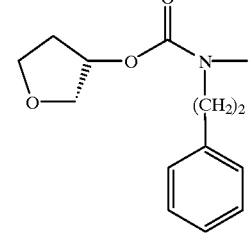
| COMPOUND | OH | Z | G | D' | R[7] |
|---|---|---|---|---|---|
| 1008 | S | 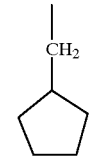 | H$_2$ | 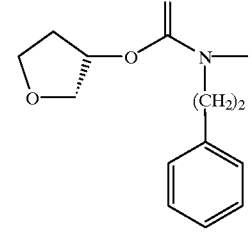 | 4-NH$_2$ |
| 1009 | S | 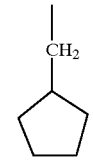 | H$_2$ | 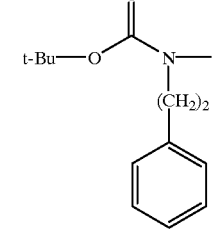 | 3-NH$_2$ |
| 1010 | S | 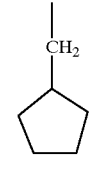 | H$_2$ | 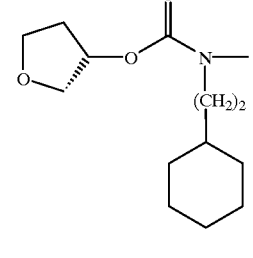 | 4-OCH$_3$ |
| 1011 | S | 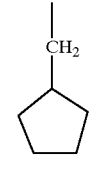 | H$_2$ | 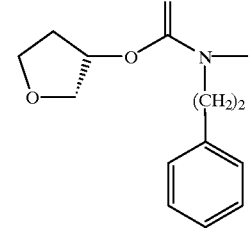 | 4-OCH$_2$ |
| 1012 | S |  | H$_2$ | i-Bu | 3-NH$_2$ |

TABLE 1-continued

| COMPOUND | OH | Z | G | D' | R[7] |
|---|---|---|---|---|---|
| 1013 | S | (bicyclic furofuran-O-C(O)-N(CH₃)-(CH₂)₂-phenyl) | H₂ | CH₂-cyclopentyl | 3-NH₂ |
| 1014 | S | (1,3-dioxane-O-C(O)-N(CH₃)-(CH₂)₂-phenyl) | H₂ | CH₂-cyclopentyl | 3-NH₂ |
| 1015 | S | (pyridin-3-yl-CH₂-O-C(O)-N(CH₃)-(CH₂)₂-phenyl) | H₂ | CH₂-cyclopentyl | 4-OCH₃ |
| 1016 | S | (tetrahydrofuran-3-yl-O-C(O)-N(CH₃)-(CH₂)₂-(4-hydroxyphenyl)) | H₂ | CH₂-cyclopentyl | 4-OCH₃ |

TABLE 1-continued

| COMPOUND | OH | Z | G | D' | R⁷ |
|---|---|---|---|---|---|
| 1017 | S | (3S)-tetrahydrofuran-3-yl O-C(=O)-N(CH₃)-(CH₂)₂-(3,4-dihydroxyphenyl) | H₂ | -CH₂-cyclopentyl | 4-OCH₃ |
| 1018 | S | 1,3-dioxolan-2-yl O-C(=O)-N(CH₃)-(CH₂)₂-phenyl | H₂ | -CH₂-cyclopentyl | 4-OCH₃ |
| 1019 | S | benzyl O-C(=O)-N(CH₃)-(CH₂)₂-phenyl | H₂ | -CH₂-cyclopentyl | 4-OCH₃ |
| 1020 | S | phenyl-CH₂-C(=O)-N(CH₃)-(CH₂)₂-phenyl | H₂ | -CH₂-cyclopentyl | 4-OCH₃ |
| 1021 | S | allyl O-C(=O)-N(CH₃)-(CH₂)₂-phenyl | H₂ | -CH₂-cyclopentyl | 4-OCH₃ |

TABLE 1-continued

| COMPOUND | OH | Z | G | D' | R⁷ |
|---|---|---|---|---|---|
| 1022 | S | phenyl O-C(=O)-N(CH₃)-(CH₂)₂-phenyl | H₂ | CH₂-cyclopentyl | 4-OCH₃ |
| 1023 | S | (pyridin-3-yl)CH₂-O-C(=O)-N(CH₃)-(CH₂)₂-phenyl | H₂ | CH₂-cyclopentyl | H |
| 1024 | S | 3-hydroxy-2-methylphenyl-C(=O)-N(CH₃)-(CH₂)₂-phenyl | H₂ | CH₂-cyclopentyl | 4-OCH₃ |
| 1025 | S | (pyridin-3-yl)CH₂-O-C(=O)-N(CH₃)-(CH₂)₂-(pyridin-3-yl) | H₂ | CH₂-cyclopentyl | 4-OCH₃ |
| 1026 | S | phenyl-C(=O)-N(CH₃)-(CH₂)₂-phenyl | H₂ | CH₂-cyclopentyl | 4-OCH₃ |

TABLE 1-continued

| COMPOUND | OH | Z | G | D' | R⁷ |
|---|---|---|---|---|---|
| 1027 | R,S | Cbz-Val-N(Me)(CH₂)₂Ph | H₂ | CH₂-cyclopentyl | 4-OCH₃ |
| 1028 | S | PhC(O)CH₂-N(Me)(CH₂)₂Ph | H₂ | CH₂-cyclopentyl | 4-OCH₃ |
| 1029 | S | PhC(O)CH₂-N(Me)(CH₂)₂CH₃ | H₂ | CH₂-cyclopentyl | 4-OCH₃ |
| 1043 | S | PhC(O)CH₂-N(Me)(CH₂)₂Ph | H₂ | CH₂-cyclopentyl | 3-NH₂ |
| 1044 | S | 3-pyridyl-C(O)-N(Me)(CH₂)₂Ph | H₂ | CH₂-cyclopentyl | 3-NH₂ |

TABLE 1-continued

| COMPOUND | OH | Z | G | D' | R⁷ |
|---|---|---|---|---|---|
| 1045 | S | N-methyl-N-(2-phenylethyl)nicotinamide | H₂ | CH₂-cyclopentyl | 3-NH₂ |
| 1046 | R,S | (4S)-4-benzyl-3-methyl-oxazolidin-2-one | H₂ | CH₂-cyclopentyl | 4-OCH₃ |
| 1047 | S | N-methyl-N-(2-phenylethyl)acetamide | H₂ | CH₂-cyclopentyl | 4-OCH₃ |
| 1048 | R,S | 2-methyl-4-phenyl-3,4-dihydroisoquinolin-1(2H)-one | H₂ | CH₂-cyclopentyl | 4-OCH₃ |
| 1125 | R,S | N-benzyl-N'-methyl-nicotinohydrazide | H₂ | CH₂-cyclopentyl | 3-NH₂ |

TABLE 2
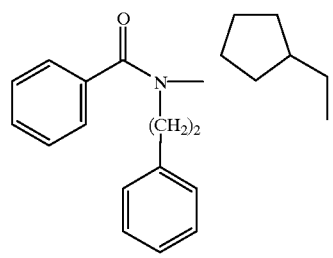
| COMPOUND | Z | D' | E' |
|---|---|---|---|
| 1050 | 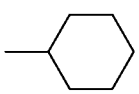 |  | 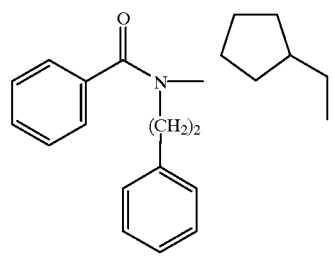 |
| 1051 |  | 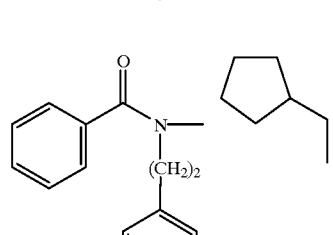 | t-Bu |
| 1052 | 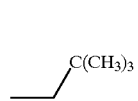 |  |  C(CH$_3$)$_3$ |
| 1053 |  |  |  |
| 1054 |  |  |  |

TABLE 2-continued

Structure: Z–CH₂–CH(OH)–CH₂–N(D')–SO₂–E'

| COMPOUND | Z | D' | E' |
| --- | --- | --- | --- |
| 1055 | benzoyl-N(CH₃)-(CH₂)₂-phenyl | cyclopentylethyl | 3-methyl-6-methoxy-tetrahydropyran |
| 1056 | benzoyl-N(CH₃)-(CH₂)₂-phenyl | cyclopentylethyl | 4-methyl-tetrahydrothiopyran-1,1-dioxide |
| 1057 | benzoyl-N(CH₃)-(CH₂)₂-phenyl | cyclopentylethyl | 3-methyl-tetrahydrothiopyran-1,1-dioxide |
| 1058 | benzoyl-N(CH₃)-(CH₂)₂-phenyl | cyclopentylethyl | 4-ethyl-tetrahydrothiopyran-1,1-dioxide |
| 1059 | benzoyl-N(CH₃)-(CH₂)₂-phenyl | cyclopentylethyl | 3,6,6-trimethyl-2,4-dioxo-thiane |

TABLE 2-continued

| COMPOUND | Z | D' | E' |
|---|---|---|---|
| 1060 | benzamide-N-methyl-(CH₂)₂-phenyl | cyclopentyl-ethyl | 3,6,6-trimethyl-2,4-dioxo-thiane 1,1-dioxide |
| 1061 | benzamide-N-methyl-(CH₂)₂-phenyl | cyclopentyl-ethyl | 3-methyl-tetrahydrothiophene 1,1-dioxide |
| 1062 | benzamide-N-methyl-(CH₂)₂-phenyl | cyclopentyl-ethyl | 4-hydroxy-3-methyl-tetrahydrothiophene 1,1-dioxide |
| 1063 | benzamide-N-methyl-(CH₂)₂-phenyl | cyclopentyl-ethyl | 4-ethyl-3-hydroxy-tetrahydrothiophene 1,1-dioxide |
| 1064 | benzamide-N-methyl-(CH₂)₂-phenyl | cyclopentyl-ethyl | 3-ethyl-tetrahydrofuran |

TABLE 2-continued

| COMPOUND | Z | D' | E' |
|---|---|---|---|
| 1065 | benzoyl-N-methyl-N-(2-phenylethyl)amino-methyl | cyclopentylethyl | 1,3-dioxolan-4-ylmethyl |
| 1066 | benzoyl-N-methyl-N-(2-phenylethyl)amino-methyl | cyclopentylethyl | 2,4-dioxoimidazolidin-5-ylmethyl |
| 1067 | benzoyl-N-methyl-N-(2-phenylethyl)amino-methyl | cyclopentylethyl | 1H-imidazol-4-ylmethyl |
| 1068 | benzoyl-N-methyl-N-(2-phenylethyl)amino-methyl | cyclopentylethyl | 5-methyl-1H-imidazol-4-ylmethyl |
| 1069 | benzoyl-N-methyl-N-(2-phenylethyl)amino-methyl | cyclopentylethyl | 2-methyl-1H-imidazol-4-ylmethyl |

TABLE 2-continued

Structure: Z-CH2-CH(OH)-CH2-N(D')-SO2-E'

TABLE 2-continued
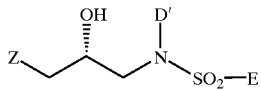
| COMPOUND | Z | D' | E' |
|---|---|---|---|
| 1075 | 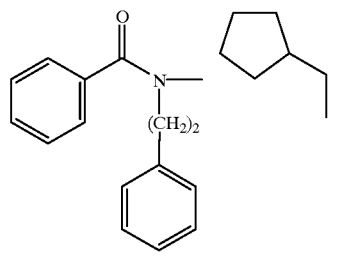 | 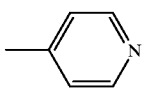 | 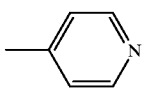 |
| 1076 | 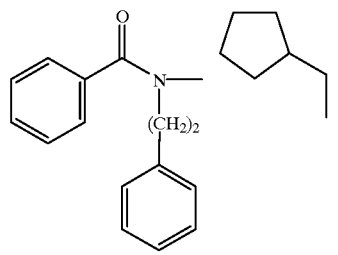 | 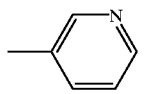 | 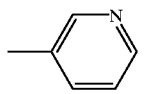 |
| 1077 | 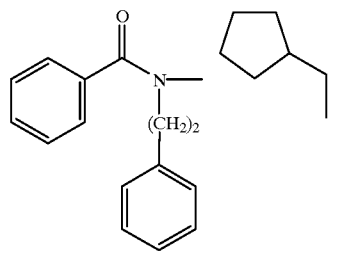 | 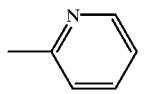 | 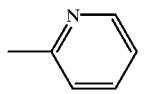 |
| 1078 | 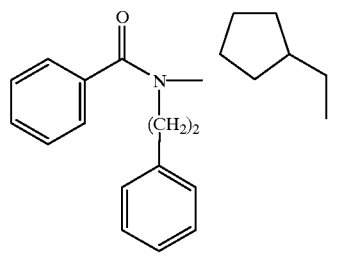 | 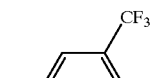 | 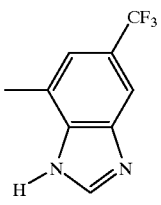 |
| 1079 | 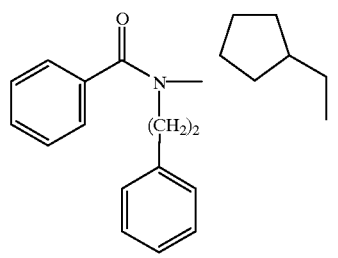 | 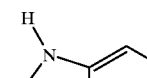 | 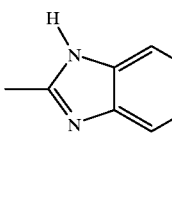 |

TABLE 2-continued

| COMPOUND | Z | D' | E' |
|---|---|---|---|
| 1080 | benzoyl-N-methyl-N-(2-phenylethyl) | cyclopentylethyl | 5-methyl-1H-benzimidazol-yl |
| 1081 | benzoyl-N-methyl-N-(2-phenylethyl) | cyclopentylethyl | benzoxazol-2-yl |
| 1082 | benzoyl-N-methyl-N-(2-phenylethyl) | cyclopentylethyl | 2-methyl-7-ethyl-benzoxazol-yl |
| 1083 | benzoyl-N-methyl-N-(2-phenylethyl) | cyclopentylethyl | 7-ethyl-benzotriazol-1-yl |
| 1084 | benzoyl-N-methyl-N-(2-phenylethyl) | cyclopentylethyl | 4,5-dimethyl-2-(NHAc)-thiazol-yl |

TABLE 2-continued

| COMPOUND | Z | D' | E' |
|---|---|---|---|
| 1085 | benzoyl-N-methyl-N-(2-phenylethyl) | cyclopentylethyl | 2-methylthiazolyl |

TABLE 3

| COMPOUND | Z | X | Y | R⁷ |
|---|---|---|---|---|
| XXXIV | (S)-tetrahydrofuran-3-yl-O-C(O)-NH- | | $CH_2$-phenyl | 4-$NH_2$ |
| LXVIII | 1,3-dioxan-5-yl-O-C(O)-NH- | | $CH_2$-phenyl | 4-$OCH_3$ |
| XXXV | (S)-tetrahydrofuran-3-yl-O-C(O)-NH- | | | 4-$NH_2$, $CH_2$-phenyl |

TABLE 3-continued

| COMPOUND | Z | X | Y | R7 |
|---|---|---|---|---|
| LXIX | 1,3-dioxan-5-yl-O-C(O)-NH- | H | benzyl | 4-OCH₃ |
| La | (S)-tetrahydrofuran-3-yl-O-C(O)-NH- | H | i-Bu | 4-OCH₃ |
| Lb | (S)-tetrahydrofuran-3-yl-O-C(O)-NH- | H | cyclopentyl-CH₂ | 4-OCH₃ |
| Lc | (S)-tetrahydrofuran-3-yl-O-C(O)-NH- | i-Bu | H | 4-OCH₃ |
| Ld | benzyl-O-C(O)-NH- | H | benzyl | 4-OCH₃ |
| Lf | (S)-tetrahydrofuran-3-yl-O-C(O)-NH- | H | benzyl | 4-OCH₃ |

TABLE 4
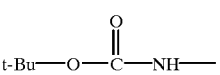
| COMPOUND | Z | D | D' | R⁷ |
|---|---|---|---|---|
| XL | t-Bu—O—C(=O)—NH— | benzyl | cyclopentylmethyl (CH₂-cyclopentyl) | 4-OCH₃ |
| LXX | (S)-tetrahydrofuran-3-yl-O—C(=O)—NH— | benzyl | cyclopentylmethyl | 4-OCH₃ |
| LXXI | 1,3-dioxan-5-yl-O—C(=O)—NH— | benzyl | cyclopentylmethyl | 4-OCH₃ |
| LIV | t-Bu—O—C(=O)—NH— | benzyl | i-Bu | 4-OCH₃ |
| LXXII | (S)-tetrahydrofuran-3-yl-O—C(=O)—NH— | benzyl | i-Bu | 4-OCH₃ |
| LXXIII | 1,3-dioxan-5-yl-O—C(=O)—NH— | benzyl | i-Bu | 4-OCH₃ |

TABLE 5

| COMPOUND | Z | G | X | X' | D' | R⁷ |
|---|---|---|---|---|---|---|
| XLI | t-Bu—NH—CO—(2-methylphenyl) | H₂ | OH | H | i-Bu | 4-OCH₃ |
| 1030 | 3-methylthiazolidine-4-CO—NH-t-Bu | O | OH | H | i-Bu | 4-OCH₃ |
| LXXXV | 3-methylthiazolidine-4-CO—NH-t-Bu | H₂ | OH (R,S) | H (R,S) | i-Bu | 4-OCH₃ |
| XLIII | 1-methylpiperidine-2-CO—NH-t-Bu | H₂ | OH | H | i-Bu | 4-OCH₃ |
| XLVI | 2-methyl-decahydroisoquinoline-3-CO—NH-t-Bu | H₂ | OH (R,S) | H (R,S) | i-Bu | 4-OCH₃ |
| XLVII | t-Bu—NH—CO—(1-methyl-4-(pyridin-3-ylmethyl)piperazin-2-yl) | H₂ | OH (R,S) | H (R,S) | i-Bu | 4-OCH₃ |
| LXXXIII | t-Bu—NH—CO—(1-methyl-4-(pyridin-3-ylmethyl)piperazin-2-yl) | O | OH (R,S) | H (R,S) | i-Bu | 4-OCH₃ |
| 1031 | 1-Cbz-4-methyl-piperazine-3-CO—NH-t-Bu | O | OH | H | i-Bu | 4-OCH₃ |

TABLE 5-continued

| COMPOUND | Z | G | X | X' | D' | R⁷ |
|---|---|---|---|---|---|---|
| 1032 | (t-Bu—NH—CO, 1-methyl-4-(pyridin-3-ylmethyl)piperazin-2-yl) | O | OH | H | i-Bu | 4-OCH₃ |
| 1033 | (CO—NH-t-Bu, 1-methylpiperidin-2-yl) | H₂ | OH | H | i-Bu | 4-OCH₃ |
| 1036 | (hexahydrofuro[3,2-b]furan-3-yl N-methyl-N-phenethylcarbamate) | H₂ | OH | H | i-Bu | 4-OCH₃ |
| 1037 | (tetrahydrofuran-3-yl N-methyl-N-phenethylcarbamate) | H₂ | OH | H | i-Bu | 4-OCH₃ |
| 1038 | (tetrahydrofuran-3-yl N-methyl-N-phenethylcarbamate) | H₂ | OH | H | i-Bu | 4-OCH₃ |

TABLE 5-continued

[Structure shown: Z-C(=G)-CX(X')-CH2-N(D')-SO2-phenyl-R7]

| COMPOUND | Z | G | X | X' | D' | R7 |
|---|---|---|---|---|---|---|
| 1039 | [tetrahydrofuran-3-yl-O-C(=O)-N(CH3)-CH2-cyclopentyl] | H2 | OH | H | i-Bu | 4-OCH3 |
| 1040 | [tetrahydrofuran-3-yl-O-C(=O)-N(CH3)-CH2-cyclopentyl] | H2 | OH | H | i-Bu | 4-OCH3 |
| 1042 | [H2N-C(=O)-(5-t-Bu-3-(NHCH3)-thiophen-2-yl)] | H2 | OH | H | i-Bu | 4-OCH3 |

TABLE 6

[Structure: R7-phenyl-SO2-N(D')-CH2-CH(OH)-CH2-CH2-N(D)-S(=O)2-E]

| COMPOUND | OH | R7 | D' | D | E |
|---|---|---|---|---|---|
| XLIVa | S | 4-OCH3 | i-Bu | i-Bu | [4-OCH3-phenyl] |
| XLIVb | R | 4-OCH3 | i-Bu | i-Bu | [4-OCH3-phenyl] |
| XLV | S | 4-OH | i-Bu | [CH2-cyclopentyl] | [4-OH-phenyl] |

TABLE 6-continued

| COMPOUND | OH | R⁷ | D' | D | E |
|---|---|---|---|---|---|
| XLIX | S | 4-NH₂ | cyclopentyl-ethyl | cyclopentyl-methyl | 4-aminophenyl |
| LVa | S | 4-OCH₃ | i-Bu | cyclopentyl-methyl | 4-methoxyphenyl |
| LVb | R | 4-OCH₃ | i-Bu | cyclopentyl-methyl | 4-methoxyphenyl |
| 1034 | S | 4-OCH₃ | i-Bu | i-Bu | —N(CH₃)₂ |
| 1035 | S | 4-OCH₃ | i-Bu | phenyl-propyl | 4-methoxyphenyl |
| 1041 | S | 4-OCH₃ | i-Bu | cyclopentyl-methyl | 3-aminophenyl |
| 1086 | S | 4-OCH₃ | i-Bu | cyclopentyl-methyl | cyclohexyl |
| 1087 | S | 4-OCH₃ | i-Bu | cyclopentyl-methyl | t-Bu |
| 1088 | S | 4-OCH₃ | i-Bu | cyclopentyl-methyl | —CH₂C(CH₃)₃ |

TABLE 6-continued

| COMPOUND | OH | R⁷ | D' | D | E |
|---|---|---|---|---|---|
| 1089 | S | 4-OCH₃ | i-Bu | ethyl-cyclopentyl | methyl-cyclopentyl |
| 1090 | S | 4-OCH₃ | i-Bu | ethyl-cyclopentyl | methyl-tetrahydropyran |
| 1091 | S | 4-OCH₃ | i-Bu | ethyl-cyclopentyl | methyl-(methoxy)tetrahydropyran |
| 1092 | S | 4-OCH₃ | i-Bu | ethyl-cyclopentyl | methyl-tetrahydrothiopyran-1,1-dioxide (4-position) |
| 1093 | S | 4-OCH₃ | i-Bu | ethyl-cyclopentyl | methyl-tetrahydrothiopyran-1,1-dioxide (3-position) |
| 1094 | S | 4-OCH₃ | i-Bu | ethyl-cyclopentyl | ethyl-tetrahydrothiopyran-1,1-dioxide |
| 1095 | S | 4-OCH₃ | i-Bu | ethyl-cyclopentyl | dimethyl-dioxo-thiopyranone |
| 1096 | S | 4-OCH₃ | i-Bu | ethyl-cyclopentyl | dimethyl-dioxo-thiopyranone sulfone |

TABLE 6-continued

| COMPOUND | OH | R⁷ | D' | D | E |
|---|---|---|---|---|---|
| 1097 | S | 4-OCH₃ | i-Bu | ethylcyclopentyl | 3-methyl-tetrahydrothiophene 1,1-dioxide |
| 1098 | S | 4-OCH₃ | i-Bu | ethylcyclopentyl | 3-methyl-4-hydroxy-tetrahydrothiophene 1,1-dioxide |
| 1099 | S | 4-OCH₃ | i-Bu | ethylcyclopentyl | 3-ethyl-4-hydroxy-tetrahydrothiophene 1,1-dioxide |
| 1100 | S | 4-OCH₃ | i-Bu | ethylcyclopentyl | 3-ethyl-tetrahydrofuran |
| 1101 | S | 4-OCH₃ | i-Bu | ethylcyclopentyl | 4-ethyl-1,3-dioxolane |
| 1102 | S | 4-OCH₃ | i-Bu | ethylcyclopentyl | 5-ethyl-hydantoin |
| 1103 | S | 4-OCH₃ | i-Bu | ethylcyclopentyl | 3-ethyl-1H-pyrrole |
| 1104 | S | 4-OCH₃ | i-Bu | ethylcyclopentyl | 4-ethyl-5-methyl-1H-imidazole |

TABLE 6-continued

| COMPOUND | OH | R⁷ | D' | D | E |
|---|---|---|---|---|---|
| 1105 | S | 4-OCH₃ | i-Bu | CH₂-cyclopentyl | 2-ethyl-1H-imidazol-1-yl |
| 1106 | S | 4-OCH₃ | i-Bu | CH₂-cyclopentyl | 5-ethyloxazole |
| 1107 | S | 4-OCH₃ | i-Bu | CH₂-cyclopentyl | 3-ethyl-5-methylisoxazole |
| 1108 | S | 4-OCH₃ | i-Bu | CH₂-cyclopentyl | 5-t-butyl-3-ethylisoxazole |
| 1109 | S | 4-OCH₃ | i-Bu | CH₂-cyclopentyl | 5-ethylthiazole |
| 1110 | S | 4-OCH₃ | i-Bu | CH₂-cyclopentyl | 2-isopropyl-4-ethylthiazole |
| 1111 | S | 4-OCH₃ | i-Bu | CH₂-cyclopentyl | 4-methylpyridine |
| 1112 | S | 4-OCH₃ | i-Bu | CH₂-cyclopentyl | 3-methylpyridine |

TABLE 6-continued
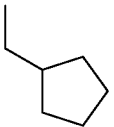
| COMPOUND | OH | R⁷ | D' | D | E |
|---|---|---|---|---|---|
| 1113 | S | 4-OCH₃ | i-Bu | 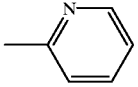 | 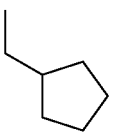 |
| 1114 | S | 4-OCH₃ | i-Bu | 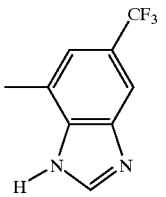 | 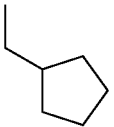 |
| 1115 | S | 4-OCH₃ | i-Bu | 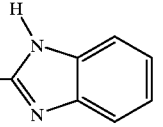 | 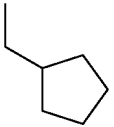 |
| 1116 | S | 4-OCH₃ | i-Bu | 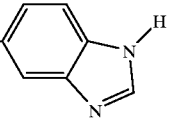 | 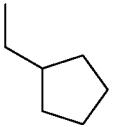 |
| 1117 | S | 4-OCH₃ | i-Bu | 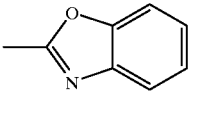 | 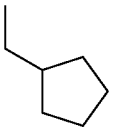 |
| 1118 | S | 4-OCH₃ | i-Bu | 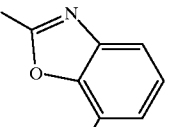 | 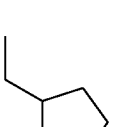 |
| 1119 | S | 4-OCH₃ | i-Bu | 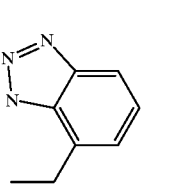 | 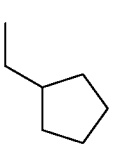 |
| 1120 | S | 4-OCH₃ | i-Bu | 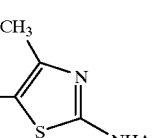 | |

TABLE 6-continued
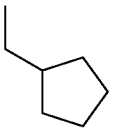
| COMPOUND | OH | R⁷ | D' | D | E |
|---|---|---|---|---|---|
| 1121 | S | 4-OCH$_3$ | i-Bu |  | 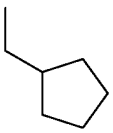 |
| 1122 | S | 4-OCH$_3$ | i-Bu | 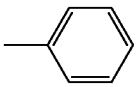 | 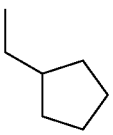 |
| 1123 | S | 4-OCH$_3$ | i-Bu |  | 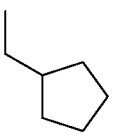 |
| 1124 | S | 4-OCH$_3$ | i-Bu | 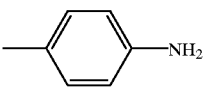 | 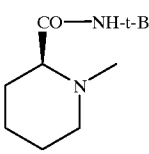 |
TABLE 7
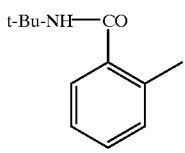
| COMPOUND | Z | G | X | X' | D' | R⁷ |
|---|---|---|---|---|---|---|
| XLVIII | 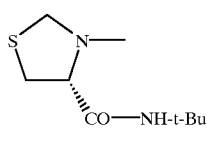CO—NH-t-Bu | H$_2$ | H | OH | i-Bu | 4-OCH$_3$ |
| LXXIV | t-Bu-NH—CO (2-methylphenyl) | H$_2$ | OH | H | i-Bu | 4-OCH$_3$ |
| LXXV | (3-methylthiazolidin-4-yl)—CO—NH-t-Bu | H$_2$ | OH | H | i-Bu | 4-OCH$_3$ |

TABLE 7-continued

![structure with G, D', Z, X, X', SO2, R7]

| COMPOUND | Z | G | X | X' | D' | R7 |
|---|---|---|---|---|---|---|
| LXXVI | (benzyl carbamate-piperazinyl-C(O)NH-t-Bu structure) | H₂ | OH | H | i-Bu | 4-OCH₃ |

TABLE 8

![structure with G, Z, X, OH, D', SO2, R7]

| COMPOUND | OH (Z) | Z | X | D' | R7 |
|---|---|---|---|---|---|
| LI | S | i-Bu—NH | CH₂-phenyl | i-Bu | 4-OCH₃ |
| LII | S | (2-hydroxyindanyl-NH) | CH₂-phenyl | i-Bu | 4-OCH₃ |
| LIII | S | t-Bu-NH—CO-(thiazolidinyl) | CH₂-phenyl | i-Bu | 4-OCH₃ |

More preferred sulfonamides of this invention include the following compounds: XLIVa, XLV, LII, LVa, 1000, 1001, 1005, 1007, 1008, 1009, 1010, 1011, 1012, 1013, 1014, 1015, 1016, 1017, 1018, 1019, 1020, 1021, 1022, 1023, 1024, 1025, 1026, 1027, 1045, and 1041.

The most preferred sulfonamides of this invention are compounds XLIVa, XLV, LII, LVa, 1001, 1005, 1007, 1008, 1009, 1010, 1011, 1013, 1015, 1016, 1018, 1019, 1021, 1023, 1024, 1026, 1027, 1045, and 1041.

In an alternative embodiment, the sulfonamides of this invention are those of formulas I', II' and III':

Formula I':

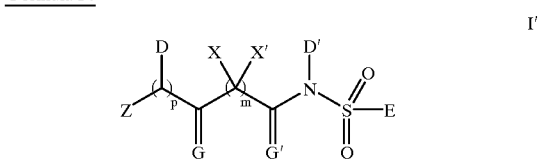

wherein:

each D and D' is independently selected from the group consisting of Ar; $C_1$–$C_6$ alkyl, which may be optionally substituted with one or more groups selected from $C_3$–$C_6$ cycloalkyl, —$OR^2$, —$R^3$, —O—Ar and Ar; $C_2$–$C_4$ alkenyl, which may be optionally substituted with one or more groups selected from the group consisting of $C_3$–$C_6$ cycloalkyl, —$OR^2$, —$R^3$, —O—Ar and Ar; $C_3$–$C_6$ cycloalkyl, which may be optionally substituted with or fused with Ar; and $C_5$–$C_6$ cycloalkenyl, which may be optionally substituted with or fused with Ar;

each Ar is independently selected from the group consisting of phenyl; 3–6 membered carbocyclic ring and 5–10 membered heterocyclic ring containing one or more heteroatoms selected from the group consisting of O, N, S, $S(O)_n$ and $N(R^2)$, wherein said carbocyclic or heterocyclic ring may be saturated or unsaturated and optionally substituted with one or more groups selected from the group consisting of oxo, —$OR^2$, —$R^2$, —$N(R^2)(R^2)$, —$N(R^2)$—C(O)—$R^2$, —$R^2$—OH, —CN, —$CO_2R^2$, —C(O)—$N(R^2)(R^2)$, halo and —$CF_3$;

each $R^2$ is independently selected from the group consisting of H and $C_1$–$C_4$ alkyl optionally substituted with phenyl, 3–6 membered carbocyclic ring and 5–10 membered heterocyclic ring containing one or more heteroatoms selected from the group consisting of O, N, S and $S(O)_n$, wherein said carbocyclic or heterocyclic ring may be saturated or unsaturated and optionally substituted with one or more groups selected from the group consisting of OH, $NH_2$, CN, $C_1$–$C_4$ alkyl, $C_1$–$C_4$ alkoxy, halogen and $CF_3$;

each $R^3$ is independently selected from the group consisting of H, Ht, $C_1$–$C_6$ alkyl, $C_2$–$C_6$ alkenyl, $C_3$–$C_6$ cycloalkyl and $C_5$–$C_6$ cycloalkenyl, wherein any member of said $R^3$, except H, may be optionally substituted with one or more substituents selected from the group consisting of —$OR^2$, —C(O)—NH—$R^2$, —S(O)$_n$—N($R^2$) ($R^2$), Ht, —CN, —$SR^2$, —$CO_2R^2$ and $NR^2$—C(O)—$R^2$;

each Ht is independently selected from the group consisting of $C_3$–$C_7$ cycloalkyl; $C_5$–$C_7$ cycloalkenyl; $C_6$–$C_{10}$ aryl; and 5–10 membered saturated or unsaturated heterocycle, containing one or more heteroatoms selected from the group consisting of N, N($R^2$), O, S and S(O)$_n$, wherein said heterocycle may optionally be benzofused; wherein said heterocycle may be bicyclic or monocyclic; and wherein any member of said Ht may be optionally substituted with one or more substituents selected from the group consisting of oxo, —$OR^2$, —$R^2$, —N($R^2$) ($R^2$), —$R^2$—OH, —CN, —$CO_2R^2$, —C(O)—N($R^2$) ($R^2$), —S(O)$_2$—N($R^2$) ($R^2$), —N($R^2$)—C(O)—$R^2$, —C(O)—$R^2$, —S(O)$_n$—$R^2$, —$OCF_3$, —S(O)$_n$—Ar, methylenedioxy, —N($R^2$)—S(O)$_2$($R^2$), halo, —$CF_3$, —$NO_2$, Ar, —O—Ar, —C(O)—N(D)(D), —C(O)—N(H)D, and —S(O)$_n$—D;

each E is independently selected from the group consisting of Ht; O—Ht; Ht—Ht; —O—$R^3$; —$NR^2R^3$; $C_1$–$C_6$ alkyl, which may be optionally substituted with one or more groups selected from the group consisting of $R^4$ and Het; $C_2$–$C_6$ alkenyl, which may be optionally substituted with one or more groups selected from the group consisting of $R^4$ and Ht; $C_3$–$C_6$ saturated monocyclic carbocycle, which be optionally benzofused, and which may optionally be substituted with one or more groups selected from the group consisting of $R^4$ and Ht; $C_5$–$C_6$ unsaturated carbocycle, which may optionally be substituted with one or more groups selected from the group consisting of $R^4$ and Ht; $C_8$–$C_{10}$ saturated bicyclic carbocycle, which may be optionally substituted with one or more groups selected from the group consisting of $R^4$ and Ht;

each $R^4$ is independently selected from the group consisting of —$OR^2$, —C(O)—$NHR^2$, —S(O)$_2$—$NHR^2$, halo, —$NR^2$—C(O)—$R^2$, —CN, —N($R^2$) ($R^2$), —$NO_2$, —C(O)N(D) (D) and —C(O)N(H)D;

each n is independently 1 or 2;

m is an integer selected from 1, 2 and 3;

p is an integer selected from 0 and 1;

G and G' are independently selected from the group consisting of $H_2$ and O;

each X and X' is independently selected from the group consisting of hydrogen; —OH; —$NH_2$; —SH; D; halogen and, if X and X' are taken together, oxygen;

Z is selected from the group consisting of —N(D)SO$_2$E; —N(D)SO$_2$Ht; —N(H)A; —N(D)A; —N(H)E; —N(H)C(O)N(D)(E); —N(H)-Ht; —Ht and —N(D)—Ht;

each A is independently selected from the group consisting of H; Ht; —$R^1$—Ht; —$R^1$—$C_1$–$C_6$ alkyl, which may be optionally substituted with one or more groups selected from the group consisting of hydroxy, $C_1$–$C_4$ alkoxy, Ht, —O—Ht, —$NR^2$—CO—N($R^2$) ($R^2$) and —CO—N($R^2$) ($R^2$); and —$R^1$—$C_2$–$C_6$ alkenyl, which may be optionally substituted with one or more groups selected from the group consisting of hydroxy, $C_1$–$C_4$ alkoxy, Ht, —O—Ht, —$NR^2$—CO—N($R^2$) ($R^2$) and —CO—N($R^2$) ($R^2$); and each $R^1$ is independently selected from the group consisting of —C(O)—, —S(O)$_2$—, —C(O)—C(O)—, —O—C(O)—, —O—S(O)$_2$, —$NR^2$—S(O)$_2$—, —$NR^2$—C(O)— and —$NR^2$—C(O)—C(O)—.

Formula II':

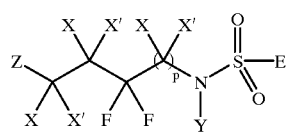

wherein:

each E is independently selected from the group consisting of Ht; O—Ht; Ht—Ht; —O—$R^3$; —$NR^2R^3$; $C_1$–$C_6$ alkyl, which may be optionally substituted with one or more groups selected from the group consisting of $R^4$ and Ht; $C_2$–$C_6$ alkenyl, which may be optionally substituted with one or more groups selected from the group consisting of $R^4$ and Ht; $C_3$–$C_6$ saturated monocyclic carbocycle, which be optionally benzofused, and which may optionally be substituted with one or more groups selected from the group consisting of $R^4$ and Het; $C_5$–$C_6$ unsaturated carbocycle, which may optionally be substituted with one or more groups selected from the group consisting of $R^4$ and Ht; $C_8$–$C_{10}$ saturated bicyclic carbocycle, which may be optionally substituted with one or more groups selected from the group consisting of $R^4$ and Ht;

each $R^4$ is independently selected from the group consisting of —$OR^2$, —C(O)—$NHR^2$, —S(O)$_2$—$NHR^2$, halo, —$NR^2$—C(O)—$R^2$, —CN, —C(O)N(D)(D) and —C(O)N(H)D;

each n is independently 1 or 2;

p is an integer selected from 0 and 1;

each Y is independently selected from the group consisting of hydrogen and D;

each D is independently selected from the group consisting of Ar; $C_1$–$C_6$ alkyl, which may be optionally substituted with one or more groups selected from the group consisting of $C_3$–$C_6$ cycloalkyl, —$OR^2$, —$R^3$, —O—Ar and Ar; $C_2$–$C_4$ alkenyl, which may be optionally substituted with one or more groups selected from the group consisting of $C_3$–$C_6$ cycloalkyl, —$OR^2$, —$R^3$, —O—Ar and Ar; $C_3$–$C_6$ cycloalkyl, which may be optionally substituted with or fused with Ar; and $C_5$–$C_6$ cycloalkenyl, which may be optionally substituted with or fused with Ar;

each Ar is independently selected from the group consisting of phenyl; 3–6 membered carbocyclic ring and 5–10 membered heterocyclic ring containing one or more heteroatoms selected from the group consisting of O, N, S, S(O) and N($R^2$), wherein said carbocyclic or heterocyclic ring may be saturated or unsaturated and optionally substituted with one or more groups selected from the group consisting of oxo, —$OR^2$, —$R^2$, —N($R^2$) ($R^2$), —N($R^2$)—C(O)—$R^2$, —$R^2$—OH, —CN, —$CO_2R^2$, —C(O)—N($R^2$) ($R^2$), halo and —$CF_3$;

each $R^2$ is independently selected from the group consisting of H and $C_1$–$C_4$ alkyl optionally substituted with phenyl, 3–6 membered carbocyclic ring and 5–10 membered heterocyclic ring containing one or more heteroatoms selected from the group consisting of O, N, S and S(O)$_n$, wherein said carbocyclic or heterocyclic ring may be saturated or unsaturated and optionally substituted with one or more groups selected from the group consisting of OH, NH$_2$, CN, C$_1$–C$_4$ alkyl, C$_1$–C$_4$ alkoxy, halogen and CF$_3$;

each R$^3$ is independently selected from the group consisting of H, Ht, C$_1$–C$_6$ alkyl, C$_2$–C$_6$ alkenyl, C$_3$–C$_6$ cycloalkyl and C$_5$–C$_6$ cycloalkenyl, wherein any member of said R$^3$, except H, may be optionally substituted with one or more substituents selected from the group consisting of —OR$^2$, —C(O)—NH—R$^2$, —S(O)$_n$—N(R$^2$) (R$^2$), Ht, —CN, —SR$^2$, —CO$_2$R$^2$ and NR$^2$—C(O)—R$^2$;

each Ht is independently selected from the group consisting of C$_3$–C$_7$ cycloalkyl; C$_5$–C$_7$ cycloalkenyl; C$_6$–C$_{10}$ aryl; and 5–10 membered saturated or unsaturated heterocycle, containing one or more heteroatoms selected from the group consisting of N, N(R$^2$), O, S and S(O)$_n$, wherein said heterocycle may optionally be benzofused; wherein said heterocycle may be bicyclic or monocyclic; and wherein any member of said Ht may be optionally substituted with one or more substituents selected from the group consisting of oxo, —OR$^2$, —R$^2$, —N(R$^2$) (R$^2$), —R$^2$—OH, —CN, —CO$_2$R$^2$, —C(O)—N(R$^2$) (R$^2$), —S(O)$_2$—N(R$^2$) (R$^2$), —N(R$^2$)—C(O)—R$^2$, —C(O)—R$^2$, —S(O)$_n$—R$^2$, —OCF$_3$, —S(O)$_n$—Ar, methylenedioxy, —N(R$^2$)—S(O)$_2$(R$^2$), halo, —CF$_3$, —NO$_2$, Ar, —O—Ar, —C(O)—N(D) (D), —C(O)N(H)D, and —S(O)$_n$—D;

each Z is independently selected from the group consisting of —N(D)SO$_2$E; —N(D)SO$_2$Ht; —N(H)A; —N(D)A; —N(H)E; —N(H)C(O)N(D)(E); —N(H)—Ht; —Ht and —N(D)—Ht;

each A is independently selected from the group consisting of H; Ht; —R$^1$—Ht; —R$^1$—C$_1$–C$_6$ alkyl, which may be optionally substituted with one or more groups selected from the group consisting of hydroxy, C$_1$–C$_4$ alkoxy, Ht and —O—Ht, —NR$^2$—CO—N(R$^2$) (R$^2$) and —CO—N(R$^2$) (R$^2$); and —R$^1$—C$_2$–C$_6$ alkenyl, which may be optionally substituted with one or more groups selected from the group consisting of hydroxy, C$_1$–C$_4$ alkoxy, Ht, —O—Ht—, —NR$^2$—CO—N(R$^2$) (R$^2$) and —CO—N(R$^2$) (R$^2$);

each R$^1$ is independently selected from the group consisting of —C(O)—, —S(O)$_2$—, —C(O)—C(O)—, —O—C(O)—, —O—S(O)$_2$, —NR$^2$—S(O)$_2$—, —NR$^2$—C(O)— and —NR$^2$—C(O)—C(O)—; and each X and X' is independently selected from the group consisting of hydrogen; —OH; —NH$_2$; —SH; D and, if X and X' are taken together, oxygen.

Formula III':

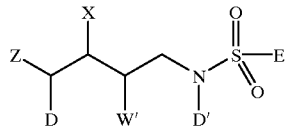

III' wherein:
each D and D' is independently selected from the group consisting of Ar; C$_1$–C$_6$ alkyl, which may be optionally substituted with one or more groups selected from the group consisting of C$_3$–C$_6$ cycloalkyl, —OR$^2$, —R$^3$, —O—Ar and Ar; C$_2$–C$_4$ alkenyl, which may be optionally substituted with one or more groups selected from the group consisting of C$_3$–C$_6$ cycloalkyl, —OR$^2$, —R$^3$, —O—Ar and Ar; C$_3$–C$_6$ cycloalkyl, which may be optionally substituted with or fused with Ar; and C$_5$–C$_6$ cycloalkenyl, which may be optionally substituted with or fused with Ar;

each Ar is independently selected from the group consisting of phenyl; 3–6 membered carbocyclic ring and 5–10 membered heterocyclic ring containing one or more heteroatoms selected from the group consisting of O, N, S, S(O)$_n$ and N(R$^2$), wherein said carbocyclic or heterocyclic ring may be saturated or unsaturated and optionally substituted with one or more groups selected from the group consisting of oxo, —OR$^2$, —R$^2$, —N(R$^2$) (R$^2$), —N(R$^2$)—C(O)—R$^2$, —R$^2$—OH, —CN, —CO$_2$R$^2$, —C(O)—N(R$^2$) (R$^2$), halo and —CF$_3$;

each R$^2$ is independently selected from the group consisting of H and C$_1$–C$_4$ alkyl optionally substituted with phenyl, 3–6 membered carbocyclic ring and 5–10 membered heterocyclic ring containing one or more heteroatoms selected from the group consisting of O, N, S and S(O), wherein said carbocyclic or heterocyclic ring may be saturated or unsaturated and optionally substituted with one or more groups selected from the group consisting of OH, NH$_2$, CN, C$_1$–C$_4$ alkyl, C$_1$–C$_4$ alkoxy, halogen and CF$_3$;

each R$^3$ is independently selected from the group consisting of H, Het, C$_1$–C$_6$ alkyl, C$_2$–C$_6$ alkenyl, C$_3$–C$_6$ cycloalkyl and C$_5$–C$_6$ cycloalkenyl, wherein any member of said R$^3$, except H, may be optionally substituted with one or more substituents selected from the group consisting of —OR$^2$, —C(O)—NH—R$^2$, —S(O)$_n$—N(R$^2$) (R$^2$), Ht, —CN, —SR$^2$, —CO$_2$R$^2$ and NR$^2$—C(O)—R$^2$;

each Ht is independently selected from the group consisting of C$_3$–C$_7$ cycloalkyl; C$_5$–C$_7$ cycloalkenyl; C$_6$–C$_{10}$ aryl; and 5–10 membered saturated or unsaturated heterocycle, containing one or more heteroatoms selected from the group consisting of N, N(R$^2$), O, S and S(O)$_n$, wherein said heterocycle may optionally be benzofused; wherein said heterocycle may be bicyclic or monocyclic; and wherein any member of said Ht may be optionally substituted with one or more substituents selected from the group consisting of oxo, —OR$^2$, —R$^2$, —N(R$^2$) (R$^2$), —R$^2$—OH, —CN, —CO$_2$R$^2$, —C(O)—N(R$^2$) (R$^2$), —S(O)$_2$—N(R$^2$) (R$^2$), —N(R$^2$)—C(O)—R$^2$, —C(O)—R$^2$, —S(O)$_n$—R$^2$—R$^2$, —OCF$_3$, —S(O)$_n$—Ar, methylenedioxy, —N(R$^2$)—S(O)$_2$(R$^2$), halo, —CF$_3$, —NO$_2$, Ar, —O—Ar, —C(O)—N(D) (D), —C(O)N(H)D, and —S(O)$_n$—D;

each E is independently selected from the group consisting of Ht; O—Ht; Ht—Ht; —O—R$^3$; —NR$^2$R$^3$; C$_1$–C$_6$ alkyl, which may be optionally substituted with one or more groups selected from the group consisting of R$^4$ and Ht; C$_2$–C$_6$ alkenyl, which may be optionally substituted with one or more groups selected from the group consisting of R$^4$ and Ht; C$_3$–C$_6$ saturated monocyclic carbocycle, which may be optionally benzofused, and which may optionally be substituted with one or more groups selected from the group consisting of R$^4$ and Het; C$_5$–C$_6$ unsaturated carbocycle, which may optionally be substituted with one or more groups selected from the group consisting of R$^4$ and Ht; C$_8$–C$_{10}$ saturated bicyclic carbocycle, which may be optionally substituted with one or more groups selected from the group consisting of R$^4$ and Ht; and each R$^4$ is independently selected from the group consisting of —OR$^2$, —C(O)—NHR$^2$, —S(O)$_2$—NHR$^2$, halo, —NR²—C(O)—R², —CN, —C(O)—N(D) (D) and —C(O)—N(H)D;

each n is independently 1 or 2;

W and W' are independently selected from the group consisting of hydrogen, D and —OH;

each Z is independently selected from the group consisting of —N(D)SO₂E; —N (D)SO₂Ht; —N (H)A; —N(D)A; —N(H)E; —N(H)C(O)N(D) (E); —N(H)—Ht; —Ht and —N(D)—Ht;

each A is independently selected from the group consisting of H; —Ht; —R¹—Ht; —R¹—C₁-C₆ alkyl, which may be optionally substituted with one or more groups selected from the group consisting of hydroxy, C₁–C₄ alkoxy, Ht, —O—Ht, —NR²—CO—N(R²) (R²) and —CO—N(R²) (R²); and —R¹—C₂-C₆ alkenyl, which may be optionally substituted with one or more groups selected from the group consisting of hydroxy, C₁–C₄ alkoxy, Ht, —O—Ht, —NR²—CO—N(R²) (R²) and —CO—N(R²) (R²); and each R¹ is independently selected from the group consisting of —C(O)—, —S(O)₂—, —C(O)—C(O)—, —O—C(O)—, —O—S(O)₂, —NR²—S(O)₂—, —NR²—C(O)— and —NR²—C(O)—C(O)—.

Except where expressly noted to the contrary, the term for any given variable, the term "[variable] as defined for formulas I', II' or III'" refers to the definitions shown directly above.

Preferred compounds of formula I' include those compounds wherein G or G' or both are oxygen. More preferably, when G or G' or both are oxygen (i.e, form a carbonyl with the carbon to which they are attached), the X and X' on the carbon adjacent to the carbonyl are independently selected from the group consisting of H, OH, F, or taken together, oxygen. Preferably, the compounds of formula I' contain from 1 to 4 carbonyls in the backbone of the structures.

Other preferred compounds of formula I' include those compounds having the structures of formulas IV', V', VI', VII', LXIII' and LXIV':

Formula IV':

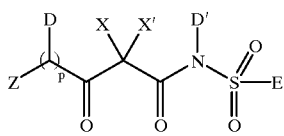

IV'

Formula V':

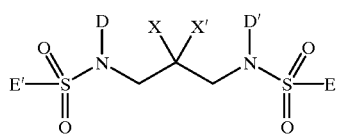

V'

Formula VI':

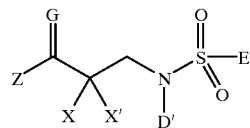

VI'

Formula VII':

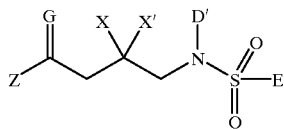

VII'

Formula LXIII':

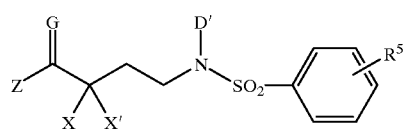

(LXIII')

Formula LXIV':

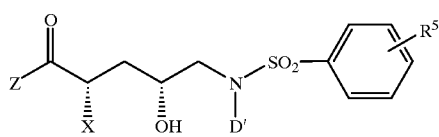

(LXIV')

wherein D, D', Ar, R¹, R², R³, Ht, E, R⁴, n, m, p, G, G', X, X', Z and A are as defined for the compounds of formula I' and R⁵ is selected from the group consisting of H, —OH, —OR², —R², —N(R²) (R²), —N(R²)—C(O)—R², —R²—OH, —CN, —CO₂R², —C(O)—N(R²)(R²), halo and —CF₃. Unless expressly noted to the contrary, the term for any given variable, the term "[variable] as defined for formula IV', V', VI', VII', LXIII' or LXIV'" refers to the definitions shown directly above.

Preferred compounds of formula IV' include those compounds wherein:

each D and D' is independently selected from the group consisting of C₁–C₆ alkyl, which may be optionally substituted with one or more groups selected from the group consisting of C₃–C₆ cycloalkyl and Ar;

each Ar is independently selected from the group consisting of phenyl; 3–6 membered carbocyclic ring and 5–10 membered heterocyclic ring containing one or more heteroatoms selected from the group consisting of O, N, S, S(O)ₙ and N(R²), wherein said carbocyclic or heterocyclic ring may be saturated or unsaturated and optionally substituted with one or more groups selected from the group consisting of oxo, —OR², —R², —N(R²) (R²), —N(R²)—C(O)—R², —R²—OH, —CN, —CO₂R², —C(O)—N(R²) (R²), halo and —CF₃;

each R² is independently selected from the group consisting of H and C₁–C₄ alkyl optionally substituted with phenyl, 3–6 membered carbocyclic ring and 5–10 membered heterocyclic ring containing one or more heteroatoms selected from the group consisting of O, N, S and S(O)$_n$, wherein said carbocyclic or heterocyclic ring may be saturated or unsaturated and optionally substituted with one or more groups selected from the group consisting of OH, NH$_2$, CN, C$_1$–C$_4$ alkyl, C$_1$–C$_4$ alkoxy, halogen and CF$_3$;

each E is independently selected from C$_5$–C$_6$ unsaturated carbocycle, which may be optionally substituted with one or more R$^4$;

each R$^4$ is independently selected from the group consisting of —OR$^2$, —N(R$^2$) (R$^2$) and —NO$_2$;

each Z is independently selected from the group consisting of —N(D)SO$_2$E; —N(D)SO$_2$Ht; —N(H)Ht; —N(H)A; —N(D)A and —Ht;

each Ht is independently selected from the group consisting of C$_6$–C$_{10}$ aryl and 5–10 membered saturated or unsaturated heterocycle, containing one or more heteroatoms selected from the group consisting of N, N(R$^2$), O, S, and S(O)$_n$, wherein said heterocycle may optionally be benzofused; wherein said heterocycle may be bicyclic or monocyclic; and wherein any member of said Ht may be optionally substituted with one or more substituents selected from the group consisting of —OR$^2$, R$^2$, —N(R$^2$) (R$^2$), —NO$_2$, —C(O)N(R$^2$) (R$^2$) and —S(O)$_n$—Ar;

X and X' are independently selected from the group consisting of H, —OH and, most preferably, if X and X' are taken together, oxygen;

each A is independently selected from the group consisting of H; —R$^1$—Ht and —R$^1$—C$_1$–C$_6$ alkyl; and each R$^1$ is independently selected from the group consisting of —C(O)—, —S(O)$_2$—, —C(O)—C(O)—, —O—C(O)—, —O—S(O)$_2$, —NR$^2$—S(O)$_2$—, —NR$^2$—C(O)— and —NR$^2$—C(O)—C(O)—.

Other more preferred compounds of formula IV' include those compounds having the structure of formulas LX' and LXI':

Formula LX':

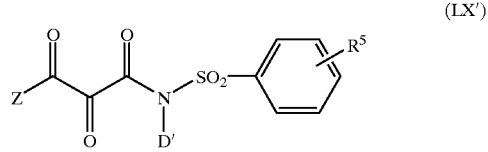
(LX')

Formula LXI':

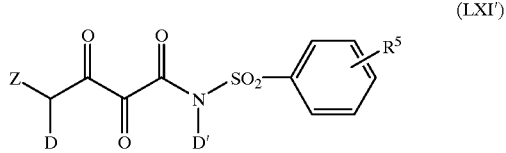
(LXI')

wherein D, D', Ar, R$^1$, R$^2$, R$^3$, Ht, E, R$^4$, n, Z and A are defined as above for the compounds of formula IV' and R$^5$ is selected from the group consisting of H, —OH, —OR$^2$, —R$^2$, —N(R$^2$)(R$^2$), —N(R$^2$)—C(O)—R$^2$, —R$^2$—OH, —CN, —CO$_2$R$^2$, —C(O)—N(R$^2$) (R$^2$), halo and —CF$_3$.

Preferred compounds of formula V' include those compounds wherein D=D' and E=E' in the backbone of the structure (i.e., a C$_2$ symmetric structure). Other preferred compounds of formula V' include those compounds wherein X is H and X' is OH in the central carbon of the backbone. Additional preferred compounds of formula V' include those compounds wherein:

each D and D' is C$_1$–C$_6$ alkyl, which may be optionally substituted with one or more groups selected from the group consisting of C$_3$–C$_6$ cycloalkyl and Ar;

each X and X' is independently selected from the group consisting of H, —OH and, if X and X' are taken together, oxygen;

each E and E' is independently selected from C$_5$–C$_6$ unsaturated carbocycle, which may be optionally substituted with one or more R$^4$; and each R$^4$ is independently selected from the group consisting of —OR$^2$, —N(R$^2$) (R$^2$) and —NO$_2$.

Preferred compounds of formula VI' include those compounds wherein:

each D and D' is independently selected from the group consisting of C$_1$–C$_6$ alkyl, which may be optionally substituted with one or more groups selected from the group consisting of C$_3$–C$_6$ cycloalkyl and Ar;

X and X' are independently selected from the group consisting of H, if X and X' are taken together, oxygen, and preferably, OH;

each E is independently selected from C$_5$–C$_6$ unsaturated carbocycle, which may be optionally substituted with one or more R$^4$;

each R$^4$ is independently selected from the group consisting of —OR$^2$, —N(R$^2$) (R$^2$) and —NO$_2$;

Z is selected from the group consisting of —N(D)SO$_2$E; —N(D)SO$_2$Ht; —N(H)Ht; —N(H)A; —N(D)A and —Het;

each Ht is independently selected from the group consisting of C$_6$–C$_{10}$ aryl and 5–10 membered saturated or unsaturated heterocycle, containing one or more heteroatoms selected from the group consisting of N, N(R$^2$), O, S, and S(O)$_n$, wherein said heterocycle may optionally be benzofused; wherein said heterocycle may be bicyclic or monocyclic; and wherein any member of said Het may be optionally substituted with one or more substituents selected from the group consisting of —OR$^2$, R$^2$, —N(R$^2$) (R$^2$), —NO$_2$, —C(O)N(R$^2$) (R$^2$) and —S(O)$_n$—Ar; and A is selected from the group consisting of H; —R$^1$—Ht and —R$^1$—C$_1$–C$_6$ alkyl.

Other preferred compounds of formula VI' include those compounds of formula LVII':

Formula LVII':

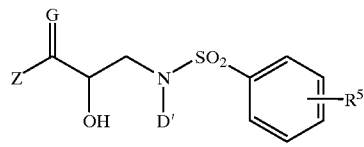
(LVII')

wherein D, D', Ar, R$^1$, R$^2$, R$^3$, Ht, E, R$^4$, G, n, Z and A are defined as above for the compounds of formula VI' and R$^5$ is selected from the group consisting of H, —OH, —OR$^2$, —R$^2$, —N(R$^2$) (R$^2$), —N(R$^2$)—C(O)—R$^2$, —R$^2$—OH, —CN, —CO$_2$R$^2$, —C(O)—N(R$^2$) (R$^2$), halo and —CF$_3$.

Preferred compounds of formula VII' include those compounds wherein:

each D and D' is C$_1$–C$_6$ alkyl, which may be optionally substituted with one or more groups selected from the group consisting of C$_3$–C$_6$ cycloalkyl and Ar;

each X and X' is independently selected from is the group consisting of H, if X and X' are taken together, oxygen, and, preferably, OH;

each E is independently selected from $C_5$–$C_6$ unsaturated carbocycle, which may be optionally substituted with one or more $R^4$;

each $R^4$ is independently selected from the group consisting of —$OR^2$, —$N(R^2)$ $(R^2)$ and —$NO_2$;

Z is selected from the group consisting of —$N(D)SO_2E$; —$N(D)SO_2Ht$; —N(H)Ht; —N(H)A; —N(D)A and —Ht;

each Ht is independently selected from the group consisting of $C_6$–$C_{10}$ aryl and 5–10 membered saturated or unsaturated heterocycle, containing one or more heteroatoms selected from the group consisting of N, $N(R^2)$, O, S, and $S(O)_n$, wherein said heterocycle may optionally be benzofused; wherein said heterocycle may be bicyclic or monocyclic; and wherein any member of said Ht may be optionally substituted with one or more substituents selected from the group consisting of —$OR^2$, $R^2$, —$N(R^2)$ $(R^2)$, —$NO_2$, —$C(O)N(R^2)$ $(R^2)$ and —$S(O)_n$—Ar; and A is selected from the group consisting of H; —$R^1$—Ht and —$R^1$—$C_1$–$C_6$ alkyl.

Other preferred compounds of formula VII, are those compounds having the structure of formula LXII':

Formula LXII':

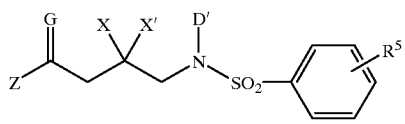

(LXIII')

wherein D, D', Ar, $R^1$, $R^2$, $R^3$, Het, E, $R^4$, G, X, n, Z and A are defined as above for the compounds of formula VII' and $R^5$ is selected from the group consisting of H, —OH, —$OR^2$, —$R^2$, —$N(R^2)$ $(R^2)$, —$N(R^2)$—$C(O)$—$R^2$, —$R^2$—OH, —CN, —$CO_2R^2$, —$C(O)$—$N(R^2)(R^2)$, halo and —$CF_3$.

Preferred compounds of formula LXIII' include those compounds wherein G is $H_2$ and X' is H.

Preferred compounds of formula LXIV' are those compounds wherein X is a $C_1$ alkyl substituted with Ar, as defined above for compounds of Formula I', and D' is a $C_1$–$C_4$ alkyl. Most preferably, X is benzyl and D' is i-Bu.

Preferred compounds of formula II' include those compounds wherein X and X' on the carbon adjacent to the carbon bearing Z on the backbone, taken together, are oxygen. Other preferred compounds of formula II' are those compounds having the structure of formula VIII':

Formula VIII':

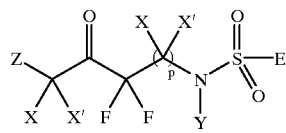

VIII' wherein E, $R^1$, $R^2$, $R^3$, $R^4$ n, p, Y, D, Ar, Ht, Z, A, X and X' are as defined above for compounds of formula II'. Except where expressly noted to the contrary, the term for any given variable, the term "[variable] defined as for a compound of formula VIII'" refers to the definition directly above.

Preferred compounds of formula VIII' include those compounds wherein on the carbon bearing Z, X is H and more preferably, X is H and X' is D. Preferred compounds of formula VIII' also include those compounds wherein E is a $C_6$–$C_{10}$ aryl optionally substituted with $OCH_3$ or $NH_2$ and Z is (S)—THF—OC(O)NH— or 5-(1,3-dioxanyl)—OC(O)NH—. Other preferred compounds of formula VIII' include those compounds wherein:

Y is H; and

X and X' on the carbon adjacent to N—Y are respectively D, preferably $C_1$–$C_6$ alkyl and H.

Other preferred compounds of formula VIII' include those wherein:

Y is D, preferably $C_1$–$C_6$ alkyl; and

X and X' on the carbon adjacent to N—Y are both hydrogen.

Other preferred compounds of formula VIII' are those compounds having the structure of formula LVIII' or LIX':

Formula LVIII':

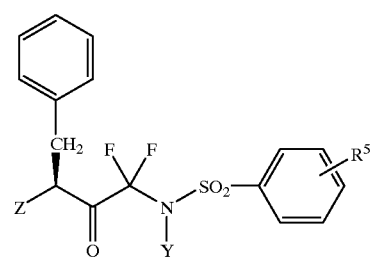

(LVIII')

Formula LIX':

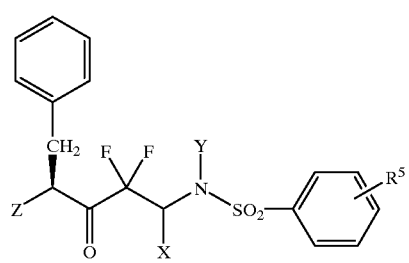

(LIX')

wherein $R^2$, $R^3$, n, Y, D, Ar, Ht; and X are as defined above for compounds of formula VIII' and $R^5$ is selected from the group consisting of H, —OH, —$OR^2$, —$R^2$, —$N(R^2)$ $(R^2)$, —$N(R^2)$—$C(O)$—$R^2$, —$R^2$—OH, —CN, —$CO_2R^2$, —$C(O)$—$N(R^2)$ $(R^2)$, halo and —$CF_3$.

Preferred compounds of formula III' are those compounds having the structure of formula IX':

Formula IX':

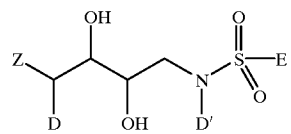

IX' wherein D, D', Ar, $R^1$, $R^2$, $R^3$, Ht, E, $R^4$, n, Z and A are defined as above for the compounds of formula III'.

Preferred sulfonamides of this invention of formulas I', II' and III' include compounds having the general formulas contained in Tables 9 through 17. In each of these tables, $R^5$ may be selected from the group consisting of H, —OH, —$OR^2$, —$R^2$, —$N(R^2)(R^2)$, —$N(R^2)$—C(O)—$R^2$, —$R^2$—OH, —CN, —$CO_2R^2$, —C(O)—$N(R^2)(R^2)$, halo and —$CF_3$; and wherein $R^2$ is defined as above for compounds of formula I'.

Preferably, at least three, and more preferably four or five, of the $R^5$ substituents are H.

TABLE 9

(LVII')

| COMPOUND | Z | G | D' |
|---|---|---|---|
| X' | phenyl-SO₂-(1-methylimidazol-2-yl) | H₂ | i-Bu |
| XI' | t-Bu-NH-C(O)-(1-methylimidazol-2-yl) | H₂ | i-Bu |
| XII' | phenyl-SO₂-(2-methylimidazol-1-yl) | H₂ | i-Bu |
| XIII' | t-Bu-NH-C(O)-NH-(1-methyl-5-CH₃-imidazol-2-yl) | H₂ | i-Bu |
| XIV' | phenyl-SO₂-(4-NH-thiophen-3-yl) | H₂ | i-Bu |

TABLE 9-continued (LVII')

| COMPOUND | Z | G | D' |
|---|---|---|---|
| XV' | t-Bu-(5-NH-pyrazol-3-yl) | H₂ | i-Bu |
| XVI' | t-Bu-NH-CO-(1-methyl-4-(pyridin-3-ylmethyl)piperazin-2-yl) | H₂ | i-Bu |
| XVII' | t-Bu-NH-CO-(3-methylthiazolidin-4-yl) | H₂ | i-Bu |
| XVIII' | t-Bu-NH-CO-(3-methylthiazolidin-4-yl) | O | i-Bu |
| XIX' | 2-hydroxy-1-NH-indanyl | H₂ | i-Bu |
| XX' | t-Bu-NH-CO-(2-methylphenyl) | H₂ | i-Bu |
| XXI' | (tetrahydrofuran-3-yl)-O-C(O)-N(benzyl)- | H₂ | -CH₂-cyclopentyl |

TABLE 9-continued (LVII')

Structure: Z-C(=G)-CH(OH)-CH2-N(D')-SO2-C6H4-R5

| COMPOUND | Z | G | D' |
|---|---|---|---|
| LXV' | 1,3-dioxan-5-yl-O-C(=O)-N(CH3)-CH2-phenyl | H2 | CH2-cyclopentyl |
| XXII' | t-Bu-NH-C(=O)-N(CH3)-CH2-phenyl | H2 | CH2-cyclopentyl |
| XXIII' | tetrahydrofuran-3-yl-O-C(=O)-N(CH3)-CH2-phenyl | H2 | CH2-cyclopentyl |
| LXVI' | 1,3-dioxan-5-yl-O-C(=O)-N(CH3)-CH2-phenyl | H2 | CH2-cyclopentyl |
| XXIV' | phenyl-SO2-N(CH3)-(CH2)2-phenyl | H2 | CH2-cyclopentyl |
| XXV' | CH3O-C6H4-SO2-N(CH3)-CH2-phenyl | H2 | CH2-cyclopentyl |
| XXVI' | CH3O-C6H4-SO2-N(CH3)-CH2-cyclopentyl | H2 | CH2-cyclopentyl |
| XXVII' | HO-C6H4-SO2-N(CH3)-CH2-cyclopentyl | H2 | CH2-cyclopentyl |
| XXVIII' | O2N-C6H4-SO2-N(i-Bu)-i-Bu | H2 | i-Bu |
| XXIX' | phenyl-SO2-N(i-Bu)-i-Bu | H2 | i-Bu |
| XXX' | CH3O-C6H4-SO2-N(i-Bu)-i-Bu | H2 | i-Bu |
| XXXI' | HO-C6H4-SO2-N(i-Bu)-i-Bu | H2 | i-Bu |
| XXXII' | H2N-C6H4-SO2-N(i-Bu)-i-Bu | H2 | i-Bu |

TABLE 10

(LVIII')

| COMPOUND | Z | Y |
|---|---|---|
| XXXII' | (S)-tetrahydrofuran-3-yl O-C(=O)-NH- | -CH2-C6H5 |
| LXVII' | 1,3-dioxan-5-yl O-C(=O)-NH- | -CH2-C6H5 |

TABLE 11

(LIX')

| COMPOUND | Z | X | Y |
|---|---|---|---|
| XXXIV' | (S)-tetrahydrofuran-3-yl O-C(=O)-NH- | H | -CH2-C6H5 |
| LXVIII' | 1,3-dioxan-5-yl O-C(=O)-NH- | H | -CH2-C6H5 |

TABLE 11-continued (LIX')

| COMPOUND | Z | X | Y |
|---|---|---|---|
| XXXV' | (S)-tetrahydrofuran-3-yl O-C(=O)-NH- | H | -CH2-C6H5 |
| LXIX" | 1,3-dioxan-5-yl O-C(=O)-NH- | H | -CH2-C6H5 |
| La' | (S)-tetrahydrofuran-3-yl O-C(=O)-NH- | H | i-Bu |
| Lb' | (S)-tetrahydrofuran-3-yl O-C(=O)-NH- | H | -CH2-C6H5 |
| Lc' | (S)-tetrahydrofuran-3-yl O-C(=O)-NH- | i-Bu | H |

TABLE 12

(LX')

| COMPOUND | Z | D' |
|---|---|---|
| XXXVI' | 4-CH3O-C6H4-SO2-N(CH3)-CH2-cyclopentyl | CH2-cyclopentyl |
| XXXVII' | 3-(phenylSO2)-4-(NH-)thiophene | CH2-cyclopentyl |
| XXXVIII' | 4-HO-C6H4-SO2-N(i-Bu)- | i-Bu |
| XXXIX' | 2-(t-Bu-NH-CO)-C6H4- | CH2-cyclopentyl |
| LVI' | 2-(t-Bu-NH-CO)-C6H4- | i-Bu |

TABLE 13

(LXI')

| COMPOUND | Z | D | D' |
|---|---|---|---|
| XL' | t-Bu-O-C(=O)-NH- | CH2-C6H5 | CH2-cyclopentyl |

TABLE 13-continued (LXI')

| COMPOUND | Z | D | D' |
|---|---|---|---|
| LXX' | (S)-tetrahydrofuran-3-yl-O-C(=O)-NH- | CH2-C6H5 | CH2-cyclopentyl |
| LXXI' | 1,3-dioxan-5-yl-O-C(=O)-NH- | CH2-C6H5 | CH2-cyclopentyl |
| LIV' | t-Bu-O-C(=O)-NH- | CH2-C6H5 | i-Bu |
| LXXII' | (S)-tetrahydrofuran-3-yl-O-C(=O)-NH- | CH2-C6H5 | i-Bu |
| LXXIII' | 1,3-dioxan-5-yl-O-C(=O)-NH- | CH2-C6H5 | i-Bu |

TABLE 14

(LXII')

| COMPOUND | Z | G | X | X' | D' |
|---|---|---|---|---|---|
| XLI' | t-Bu—NH—CO-(2-methylphenyl) | H₂ | OH | H | i-Bu |
| XLII' | N-methylthiazolidine-CO-NH-t-Bu | O | OH | H | i-Bu |
| LXXXV' | N-methylthiazolidine-CO-NH-t-Bu | H₂ | OH | H | i-Bu |
| XLIII' | 1-methylpiperidine-2-CO-NH-t-Bu | H₂ | OH | H | i-Bu |
| XLIVa' | 4-CH₃O-C₆H₄-SO₂-N(CH₃)(i-Bu) | H₂ | OH | H | i-Bu |
| XLIVb' | 4-CH₃O-C₆H₄-SO₂-N(CH₃)(i-Bu) | H₂ | OH | H | i-Bu |
| XLV' | 4-HO-C₆H₄-SO₂-N(CH₃)(CH₂-cyclopentyl) | H₂ | OH | H | i-Bu |
| XLV☐I' | 2-methyl-decahydroisoquinoline-3-CO-NH-t-Bu | H₂ | OH | H | i-Bu |

TABLE 14-continued (LXII')

| COMPOUND | Z | G | X | X' | D' |
|---|---|---|---|---|---|
| XLVIII' | t-Bu—NH—CO-(1-methyl-4-(pyridin-3-ylmethyl)piperazin-2-yl) | H₂ | OH | H | i-Bu |
| LXXXIII' | t-Bu—NH—CO-(1-methyl-4-(pyridin-3-ylmethyl)piperazin-2-yl) | O | OH | H | i-Bu |
| XLIX' | H₂N—C₆H₄—SO₂—N(CH₂-cyclopentyl)— | H₂ | OH | H | CH₂-cyclopentyl |
| LVa' | CH₃O—C₆H₄—SO₂—N(CH₂-cyclopentyl)— | H₂ | OH | H | i-Bu |
| LVb' | CH₃O—C₆H₄—SO₂—N(CH₂-cyclopentyl)— | H₂ | OH | H | i-Bu |

TABLE 15

(LXIII')

COMPOUND | Z | G | X | X' | D'
---|---|---|---|---|---
XLVIII' | (1-methylpiperidin-2-yl)-CO—NH-t-Bu | H₂ | OH | H | i-Bu
LXXIV' | t-Bu—NH—CO-(2-methylphenyl) | H₂ | OH | H | i-Bu
LXXV' | (3-methylthiazolidin-4-yl)-CO—NH-t-Bu | H₂ | OH | H | i-Bu
LXXVI' | t-Bu—NH—CO-(1-methyl-4-(pyridin-3-ylmethyl)piperazin-2-yl) | H₂ | OH | H | i-Bu
LXXVII' | (4-(phenylsulfonyl)thiophen-3-yl)-NH—CH₂— | H₂ | OH | H | i-Bu

TABLE 16

(LXIV')

COMPOUND | Z | X | D'
---|---|---|---
LI' | i-Bu—NH | benzyl (CH₂-phenyl) | i-Bu

TABLE 16-continued (LXIV')

COMPOUND | Z | X | D'
---|---|---|---
LII' | (2-hydroxy-2,3-dihydro-1H-inden-1-yl)-NH— | | i-Bu (CH₂-phenyl)

TABLE 16-continued

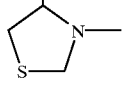
(LXIV')

| COMPOUND | Z | X | D' |

LIII' | t-Bu—NH—CO-[thiazolidine] | [structure] | i-Bu, —CH₂—Ph |

TABLE 17

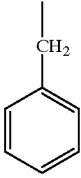
La'

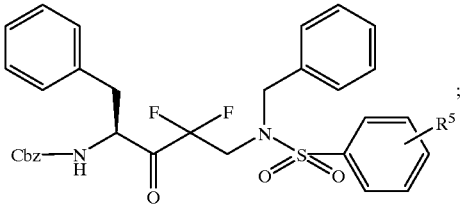
Le'

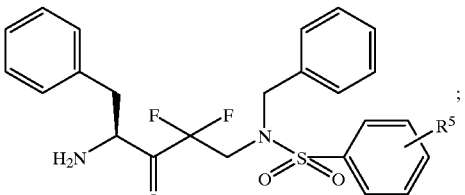
Lf'

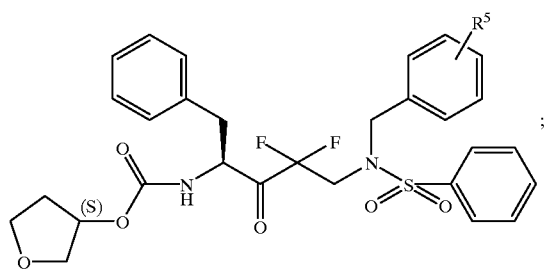
LXXXI'

TABLE 17-continued

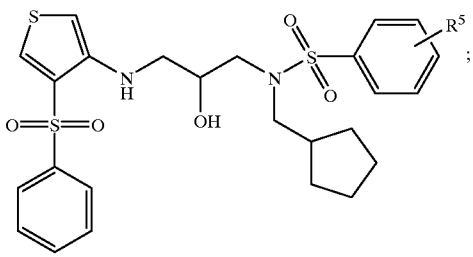
LXXXII'

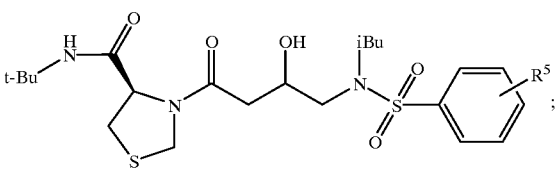
; and

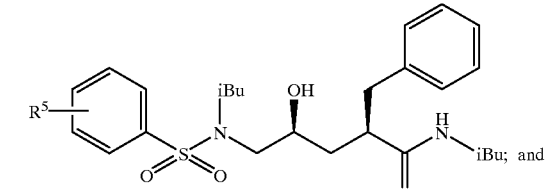
LXXXV'

The sulfonamides of this invention may be synthesized using conventional techniques. Advantageously, these compounds are conveniently synthesized from readily available starting materials.

The compounds of this invention are among the most readily synthesized HIV protease inhibitors known. Previously described HIV protease inhibitors often contain four or more chiral centers and numerous peptide linkages. The relative ease with which the compounds of this invention can be synthesized represents an enormous advantage in the large scale production of these compounds. Although the syntheses of the sulfonamides of this invention are known to those of skill in the art, the following general schemes are set forth to illustrate these methods. These schemes should not be viewed as limiting the scope of this invention in any way.

Using standard techniques, compounds of the present invention having the general formula IVa may be obtained as described in Scheme 1:

Scheme 1

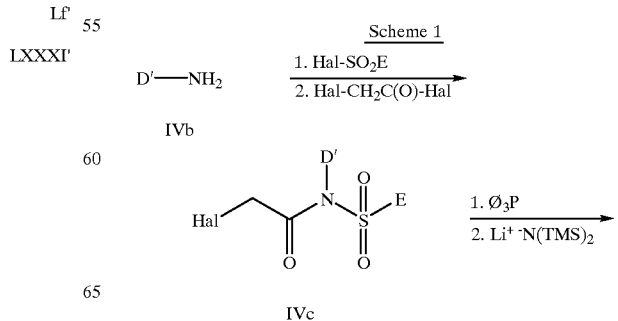

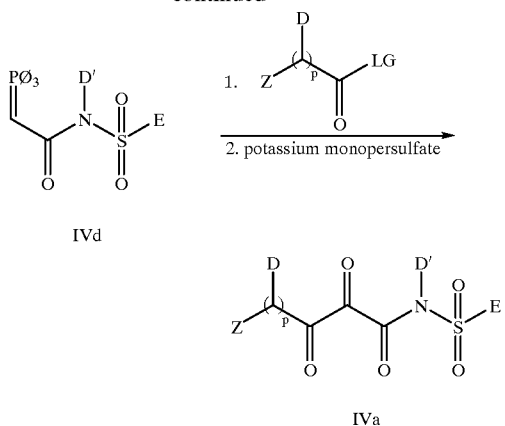

Primary amine IVb, wherein D' is defined as above for the compounds of formula I, may be converted to the N-acylsulfonamide of formula IVc, first by sulfonylating with a sulfonyl halide having the general formula Hal—SO$_2$E, wherein Hal is any halogen and E is defined as above for the compounds of formula I, and then by N-acylating with a haloacetyl halide having the general formula Hal—CH$_2$—C(O)Hal, wherein Hal is defined above.

Preferred sulfonylating agents have the general structure Cl—SO$_2$E, wherein E is defined as above for the compounds of formula I. The sulfonylation reaction may optionally take place in the presence of a base to scavenge the hydrohalic acid product as a reaction byproduct. Such bases include, but are not limited to triethylamine, pyridine, 4-dimethylaminopyridine, sodium bicarbonate and potassium carbonate. We prefer using sodium bicarbonate.

The resulting sulfonamide is then N-acylated with a haloacetyl halide having the general formula Hal—CH$_2$—C(O)Hal, wherein Hal is defined as above, to give the N-acylsulfonamide of formula IVc. Haloacetyl halides include bromoacetyl bromide, chloroacetyl chloride and preferably, bromoacetyl chloride. The acylation reaction is preferably run in the presence of a base strong enough to deprotonate the sulfonamide nitrogen prior to N-acylation. Preferred bases include lithium diisopropyl amide and potassium bis(trimethylsilyl)amide. We especially prefer lithium bis(trimethylsilyl)amide.

The N-acylsulfonamide of formula IVc is then converted to its ylide derivative of formula IVd, wherein D' and E are defined as for the compounds of formula I, first by treating the compound of formula IVc with triphenylphosphine to form the phosphonium halide salt, and then by deprotonating the phosphonium halide salt with a strong base to form the ylide of formula IVd. Such strong bases include, but are not limited to, lithium diisopropyl amide, potassium bis (trimethylsilyl)amide and lithium bis(trimethylsilyl)amide. We prefer to deprotonate the phosphonium halide salt with lithium bis(trimethylsilyl)amide.

The ylide IVd is then converted to tricarbonyl IVa by a two-step acylation/oxidation process. The procedure for carrying out such a process is described in Wasserman et al., J. Org. Chem., 58, pp. 4785–87 (1993) and references cited therein. Ylide IVd is first acylated with Z—(CHD)$_p$C(O)—LG, wherein Z, D and p are defined above as for compounds of formula I and LG is any conventional leaving group. Suitable leaving groups include, but are not limited to, hydroxyl, carboxylates and halides. Preferably, the leaving group is either hydroxyl or halide, most preferably chloride. Acylation reactions of this type may optionally be run in the presence of a base.

When the leaving group in the acylation reaction is halide, suitable bases include, but are not limited to triethylamine, pyridine, 4-dimethylaminopyridine, sodium bicarbonate, potassium carbonate and preferably, bis(trimethylsilyl) acetamide. When the leaving group is hydroxyl, dehydrating agents such as (1-(3-dimethylaminopropyl)-3-ethylcarbodiimide and dicyclohexylcarbodiimide may be optionally used to facilitate acylation. We prefer to use (1-(3-dimethylaminopropyl)-3-ethylcarbodiimide.

The product of the acylation step is treated with an oxidizing agent to give, after rearrangement, triphenylphosphine oxide and tricarbonyl compound IVa, wherein Z, D, p, D' and E are defined as above for compounds of formula I. Suitable oxidizing agents include, but are not limited to hydrogen peroxide, organic peracids such as peracetic acid and m-chloroperbenzoic acid, sodium hypochlorite and preferably, Oxone® (a commercially available mixture of potassium monopersulfate, potassium sulfate and potassium bisulfate).

Compounds of Formula IVa and other compounds of this invention having three adjacent carbonyls on their backbone structures may optionally be hydrated at the central carbonyl. Methods to hydrate or prevent hydration of this central carbonyl are known to those of ordinary skill in the art.

Compounds of the present invention having the general formula VIIIa may be obtained by the synthesis described in Scheme 2a:

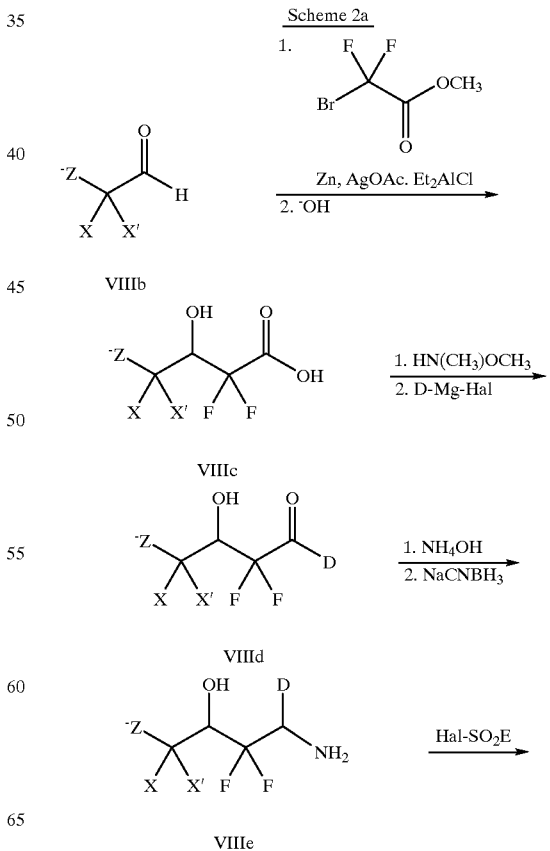

-continued

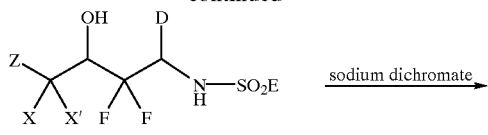

VIIIf

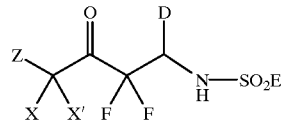

VIIIa

Aldehyde VIIIb is converted to difluoroacid VIIIc, wherein Z, X and X' are defined as above for compounds of formula II, first by condensing the aldehyde with methyl difluorobromoacetate in the presence of zinc, silver(I) acetate and diethylaluminum chloride to give a difluoro methyl ester (as described in T. T. Curran, *J. Org. Chem.*, 58, pp. 6360–63 (1993)) and then hydrolyzing the methyl ester to a carboxylic acid. The present invention envisions the use of either acidic or basic hydrolysis. Bases which may be employed include potassium hydroxide, lithium hydroxide and sodium hydroxide. We prefer basic hydrolysis using sodium hydroxide.

Acid VIIIc is then converted to ketone VIIId, wherein D, X and X' are defined as above for compounds of formula II, via an N-methoxy-N-methylamide which is obtained by treating the acid with N-methoxy-N-methylamine. The N-methoxy-N-methylamide is then treated with a Grignard reagent of the general formula D—Mg—Hal, wherein D is defined as above for compounds of formula II and Hal is any halogen. Preferably, the halogen is chloride or bromine.

Ketone VIIId is then converted to primary amine VIIIe, wherein Z, X, X' and D are defined as above for compounds of formula II, first by forming an imine with an ammonia equivalent and then by reducing the imine to a primary amine. To form the imine, liquid ammonia or preferably, ammonium hydroxide may be used. The reduction of the imine may be carried out using any conventional hydride, but preferably using sodium cyanoborohydride. One convenient reduction scheme is the Borch reduction described in R. F. Borch et al., *J. Amer. Chem. Soc.*, 93, pp. 2897–904 (1971).

The primary amine VIIIe is then sulfonylated with a sulfonyl halide having the general formula Hal—$SO_2$E, wherein Hal is any halogen and E is defined as above for compounds of formula II, to give hydroxysulfonamide VIIIf, wherein Z, X, X', D and E are defined as above for compounds of formula II. Preferably, Hal is chloride.

The hydroxysulfonamide VIIIf is then oxidized to give compounds of the general structure VIIIa, wherein Z, X, X', D and E are defined as above for the compounds for formula II. Typical oxidizing agents include, but are not limited to, pyridinium dichromate, pyridinium chlorochromate, and dimethylsulfoxide/triethylamine/oxalyl chloride (Swern oxidation conditions). Preferably, the oxidizing agent is sodium dichromate.

Compounds of the present invention having the general formula VIIIl may be obtained by the synthetic route described below in Scheme 2b:

Scheme 2b

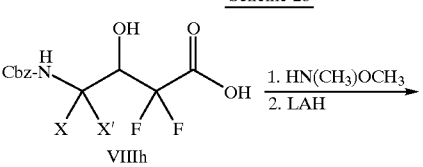

VIIIh

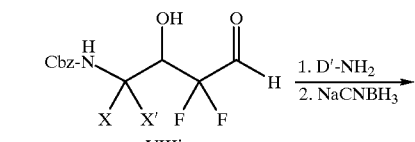

VIIIi

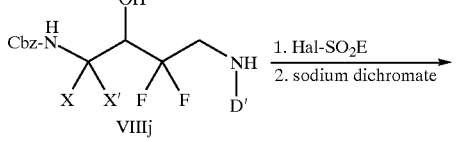

VIIIj

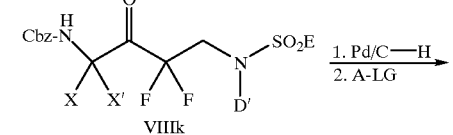

VIIIk

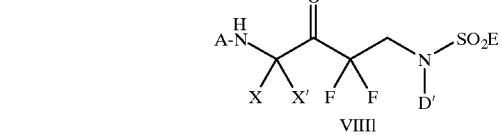

VIIIl

Carboxylic acid VIIIh, wherein X and X' are defined as in formula II, is reduced to aldehyde VIIIi, wherein X and X' are defined as in formula II, first by forming an amide with N-methoxy-N-methylamine and then by reducing the amide to give aldehyde VIIi. Suitable reducing agents include, but are not limited to sodium borohydride, sodium cyanoborohydride, lithium and potassium tri-sec-butylborohydride and preferably, lithium aluminum hydride.

Aldehyde VIIIi is then treated with a primary amine having the general formula D'—$NH_2$, wherein D' is defined the same as D above for compounds of formula II (as used throughout this scheme, D' will be defined as D above for compounds of formula II), to give an imine which is reduced to give a secondary amine having the general formula VIIIj, wherein X and X' are defined as above for the compounds of formula II and D' is defined as above. The reducing agent which is used can be essentially any hydride reducing agent known to those skilled in the art, preferably, sodium cyanoborohydride.

Secondary amine VIIIj is then sulfonylated with a sulfonylating agent having the general formula Hal—$SO_2$E, wherein Hal is any halogen and E is defined above for the compounds of formula II and then oxidized to give N-Cbz ketone of the formula VIIIk, wherein X, X' and E are defined as above for compounds of formula II and D' is defined in the preceding paragraph. Suitable oxidizing agents include, but are not limited to pyridinium dichromate, pyridinium chlorochromate, dimethyl sulfoxide/triethylamine/oxalyl chloride (Swern oxidation conditions) and preferably, sodium dichromate.

Ketone VIIIk is then reduced with hydrogen in the presence of Pd/C catalyst to remove the Cbz group, and then acylated or sulfonylated with A-LG, wherein A is defined as above for compounds of formula II and LG is a suitable leaving group. Suitable leaving groups include, but are not limited to, halogen, hydroxyl, alkanoate, and preferably N-oxysuccinimidate.

Preferred A-LG are 3-(S)-tetrahydrofuranyl succinamidyl carbonate and 1,3 dioxane-p-nitrophenyl carbonate. 1,3 dioxane-p-nitrophenyl carbonate is prepared according to Example 36 below. Treatment of VIIIk, as above, gives compound VIII1, wherein A, X, X' and E are defined as above for compounds having the formula II and D' is defined as in the preceding paragraph.

Compounds of the present invention having the general formula Va and Vc may be obtained by the steps shown below in Scheme 3:

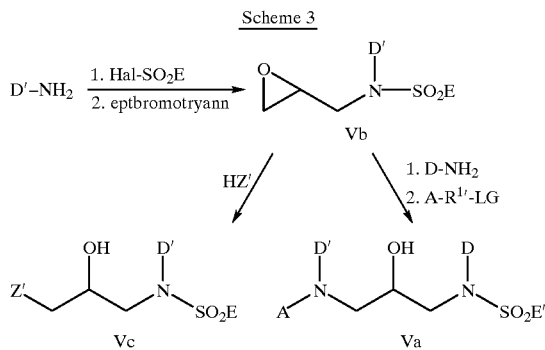

A primary amine having the general formula D'—NH₂, wherein D' is defined as for compounds of formula I, is sulfonylated with a sulfonyl halide having the general formula Hal—SO₂E, wherein Hal is any halogen and E is defined as above for compounds of formula I, to give a sulfonamide, which in turn is alkylated with an epihalohydrin, or if a enantiomerically pure product is desired, a chiral glycidyl derivative to give epoxide Vb. Suitable epihalohydrins include, but are not limited to, epichlorohydrin, epiiodohydrin and preferably, epibromohydrin. Suitable chiral glycidyl derivatives include, but are not limited to, (2S)-(+)- and (2R)-(−)-glycidyl tosylate and (2S)-(+)- and (2R)-(−)-glycidyl 3-nitrobenzenesulfonate.

Epoxide Vb is then selectively ring-opened with a primary amine having the general formula D—NH₂, wherein D is defined as above for compounds of formula I, to give a diamine which is then acylated at the secondary amine position to give compound Va. The acylating agent has the formula A—R¹'—LG, wherein A is as defined above for compounds of formula I, R¹' is selected from the group consisting of —C—(O)—, —O—C—(O)— and —NR²—C(O)— and LG is as defined above.

Alternatively, epoxide Vb may be ring-opened with an amino species HZ', wherein Z' is —N(D)SO₂E, —N(H)A, —N(D)A, —N(H)E, —N(H)C(O)N(D)(E), —N(H)Ht, —N(D)Ht and —Ht', wherein D, E, Het and A are defined above as in formula I and —Ht' is a 5–10 membered nitrogen-containing heterocycle optionally substituted with any of the Ht substituents mentioned for compounds of formula I. Alkylation of Vb with HZ' gives compounds of the general formula Vc, wherein Z' is defined as above and D' and E are defined as above for compounds of formula I.

Compounds of the present invention having the general formulas VIIa and VIIe are obtained by the methods described below in Scheme 4 and 4a:

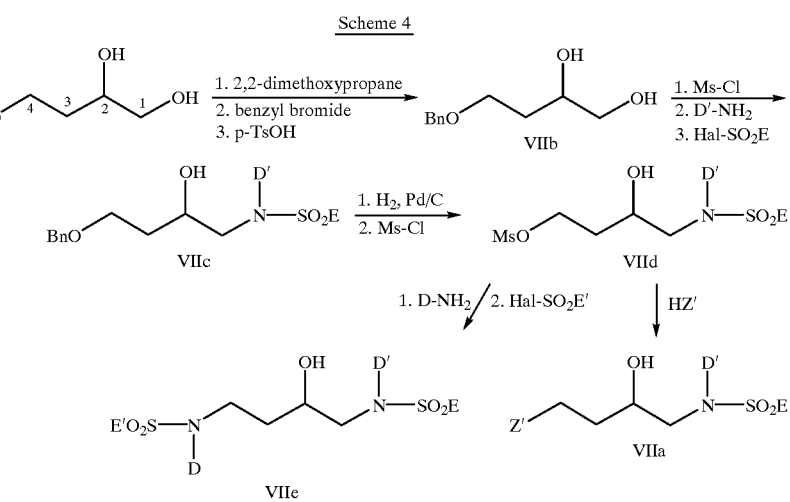

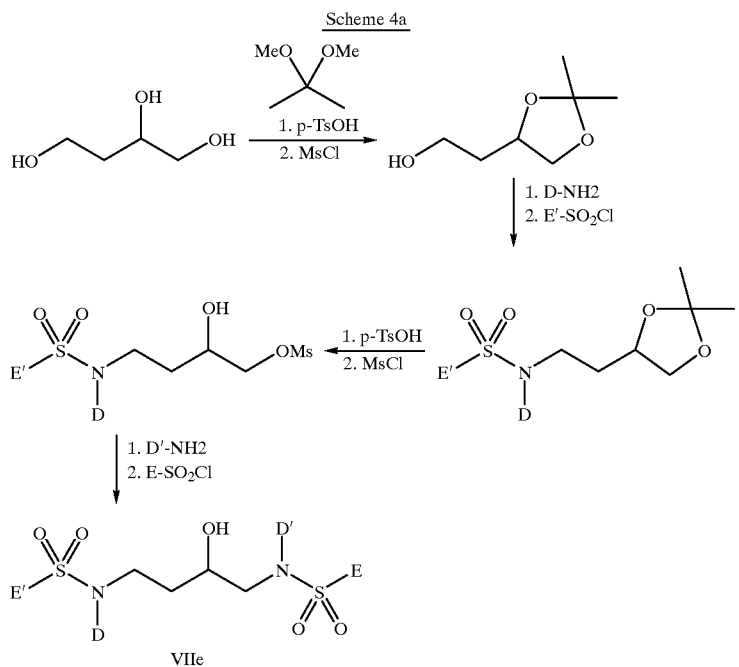

Scheme 4a 1,2,4-Butanetriol is ketalized with any suitable ketone or ketone equivalent, such as a dialkylketal thereof, in the presence of a protic acid, to give a primary alcohol bearing a ketal at the 1 and 2 positions. Such ketones, ketone equivalents, and protic acids are known to those of ordinary skill in the art. A preferred ketone is acetone, a preferred ketone equivalent is 2,2-dimethyoxypropane and a preferred protic acid is p-toluenesulfonic acid. The primary alcohol is then protected with any conventional acid-stable protecting group. Examples of such protecting groups can be found, for example, in T. W. Greene, *Protective Groups in Organic Synthesis*, John Wiley and Sons (1991). A preferred protecting group is benzyl bromide. The resulting benzyl ketal is then deprotected with any conventional protic acid to give the benzyl diol of formula VIIb. We prefer to use p-toluenesulfonic acid.

Diol VIIb is then activated at its primary hydroxyl site. Suitable activating reagents include, but are not limited to, p-toluenesulfonyl halides, trifluoromethanesulfonyl halides, 4-bromobenzenesulfonyl halides and preferably, methanesulfonyl halides. Preferably, diol VIIb is treated with methanesulfonyl chloride to give a mesylate, which is alkylated with a primary amine having the general D'—$NH_2$, wherein D' is defined as above for compounds of formula I. The resulting secondary amine is sulfonylated with a sulfonating agent having the formula Hal—$SO_2E$, wherein Hal is any halogen and E is defined as above for compounds of formula I, to give benzyl sulfonamide VIIc.

Sulfonamide VIIc is then hydrogenated in the presence of a suitable catalyst, such as Pd/C, to remove the benzyl group from the primary hydroxyl group and further activated at its primary hydroxyl site to convert the primary hydroxyl to a better leaving group. Such agents useful for this purpose include, but are not limited to p-toluenesulfonyl halides, trifluoromethanesulfonyl halides, 4-bromobenzenesulfonyl halides and preferably, methanesulfonyl halides. We prefer to treat the resulting primary hydroxyl group with methanesulfonyl chloride to give mesylate VIId.

Mesylate VIId may then be alkylated with a primary amine having the formula D—$NH_2$, wherein D is defined as above for compounds of formula I, to give an aminosulfonamide. The aminosulfonamide is further N-sulfonylated with a sulfonylating agent having the formula Hal—$SO_2E'$, wherein Hal is any halogen and E' is defined as E above for compounds of formula I, to give compounds of the general formula VIIe, wherein D, D' and E are defined as above for compounds of formula I and E' is defined as above.

Alternatively, mesylate VIId may be alkylated with an amino species HZ', wherein Z' is —N(D)$SO_2$E, —N(H)A, —N(D)A, —N(H)E, —N(H)C(O)N(D)(E), —N(H)Ht, —N(D)Ht and —Ht', wherein D, E, Het and A are defined above as in formula I and —Het' is a 5–10 membered nitrogen-containing heterocycle optionally substituted with any of the Ht substituents mentioned for compounds of formula I. Alkylation of VIId with HZ' gives compounds of the general formula VIIa, wherein Z' is defined as above and D' and E are defined as above for compounds of formula I. The reactions described above can be utilized in an alternate order to produce compounds of formula VIIe, as shown in Scheme 4a above.

Compounds of the present invention having the general formula VIIg are obtained by the methods described below in Scheme 5:

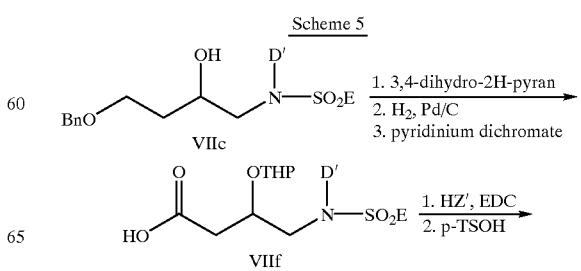

Scheme 5

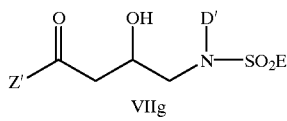

VIIg

Sulfonamide VIIc, wherein D' and E are defined above for compounds of formula I, may be protected as its tetrahydropyran ether, using 3,4-dihydro-2H-pyran and p-toluenesulfonic acid. The resulting tetrahydropyran ether is hydrogenated in the presence of Pd/C to remove the benzyl group and give a primary alcohol. The resulting primary alcohol is then oxidized in the presence of pyridinium dichromate to give carboxylic acid VIIf.

Carboxylic acid VIIf may then be amidated in the presence of EDC and HOBT with an amino species HZ', wherein Z' is —N(D)SO₂E, —N(H)A, —N(D)A, —N(H)E, —N(H)C(O)N(D)(E), —N(H)Ht, —N(D)Ht or —Ht', wherein D, E, Het and A are defined above as in formula I and —Ht' is a 5–10 membered nitrogen-containing heterocycle optionally substituted with any of the Het substituents mentioned for compounds of formula I. Amidation of VIIf with HZ' gives compounds of the general formula VIIg, wherein Z' is defined as above and D' and E are defined as above for compounds of formula I.

As can be appreciated by the skilled artisan, the above synthetic schemes are not intended to comprise a comprehensive list of all means by which the compounds described and claimed in this application may be synthesized. Further methods will be evident to those of ordinary skill in the art.

It should be understood that the compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The compounds of this invention are characterized by a superior ability to inhibit protease activity and viral replication. These compounds are especially well suited for inhibiting HIV aspartyl protease. We believe that this activity is due to specific steric and electronic interactions between the protease and compounds of this invention. This belief stems from our analysis of the structural basis for the activity of compounds of this invention, in view of the known crystal structures of HIV protease and bound inhibitors, such as the structure reported in Miller et al. "Structure of Complex of Synthetic HIV-1 Protease with a Substrate-Based Inhibitor at 2.3 Å Resolution", *Science*, vol. 246, pp. 1149–1152 (1989), which is incorporated herein by reference, as well as structures determined in our laboratories.

The novel compounds of the present invention are excellent ligands for aspartyl proteases, particularly HIV-1 and HIV-2 proteases. Accordingly, these compounds are capable of targeting and inhibiting late stage events in HIV replication, i.e., the processing of the viral polyproteins by HIV encoded proteases. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected cells. Compounds according to this invention advantageously inhibit the ability of the HIV-1 virus to infect immortalized human T cells over a period of days, as determined by an assay of extracellular p24 antigen—a specific marker of viral replication. Other antiviral assays have confirmed the potency of these compounds.

The compounds of this invention may be used in the manufacture of a medicament for treating viral infection in a mammal. It will be evident to one skilled in the art that the compounds of this invention, including the preferred compounds of formulas VI, VII, and C, may be employed in a conventional manner for the treatment of viral infections, such as HIV and HTLV, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally-infected patient in a pharmaceutically acceptable manner and in an amount effective to lessen the severity of the viral infection or to alleviate pathological effects associated with HIV infection or immunosuppression such as opportunistic infections or various cancers.

Alternatively, the compounds of this invention may be used in used in the manufacture of a medicament for preventing viral infection in a mammal. It will be evident to one skilled in the art that the compounds of this invention, including the preferred compounds of formulas VI, VII, and C, may be used in prophylactics and methods for protecting individuals against viral infection during a specific event, such as childbirth, or over an extended period of time. The compounds may be employed in such prophylactics either alone or together with other antiretroviral agents to enhance the efficacy of each agent. As such, the novel protease inhibitors of this invention can be administered as agents for treating or preventing HIV infection in a mammal.

The compounds of formula I or II, especially those having a molecular weight of less than about 700 g/mole, may be readily absorbed into the bloodstream of mammals upon oral administration. Compounds of formula I or II having a molecular weight of less than about 600 g/mole and aqueous solubility of greater than or equal to 0.1 mg/mL are most likely to demonstrate high and consistent oral availability. This surprisingly impressive oral availability makes such compounds excellent agents for orally-administered treatment and prevention regimens against HIV infection.

In addition to being orally bioavailable, the compounds of this invention also have an impressively high therapeutic index (which measures toxicity versus anti-viral effect). Accordingly, the compounds of this invention are effective at lower dosage levels than many previously described conventional antiretroviral agents and avoid many of the severe toxic effects associated with those drugs. The potential of these compounds to be delivered at doses far exceeding their effective antiviral levels is advantageous in slowing or preventing the possibility of resistant variants developing.

The compounds of this invention may be administered to a healthy or HIV-infected patient either as a single agent or in combination with other anti-viral agents which interfere with the replication cycle of HIV. By administering the compounds of this invention with other anti-viral agents which target different events in the viral life cycle, the therapeutic effect of these compounds is potentiated. For instance, the co-administered anti-viral agent can be one which targets early events in the life cycle of the virus, such as cell entry, reverse transcription and viral DNA integration into cellular DNA. Anti-HIV agents targeting such early life cycle events include, didanosine (ddI), dideoxycytidine (ddC), d4T, zidovudine (AZT), 3TC, 935U83, 1592U89, 524W91, polysulfated polysaccharides, sT4 (soluble CD4), ganiclovir, trisodium phosphonoformate, eflornithine, ribavirin, acyclovir, alpha interferon and tri-menotrexate. Additionally, non-nucleoside inhibitors of reverse transcriptase, such as TIBO, delavirdine (U90) or nevirapine, may be used to potentiate the effect of the compounds of this invention, as may viral uncoating inhibitors, inhibitors of trans-activating proteins such as tat or rev, or inhibitors of the viral integrase.

Combination therapies according to this invention exert an additive or synergistic effect in inhibiting HIV replication because each component agent of the combination acts on a different site of HIV replication. The use of such combination therapies may also advantageously reduce the dosage of a given conventional anti-retroviral agent which would be required for a desired therapeutic or prophylactic effect, as compared to when that agent is administered as a monotherapy. Such combinations may reduce or eliminate the side effects of conventional single anti-retroviral agent therapies, while not interfering with the anti-retroviral activity of those agents. These combinations reduce potential of resistance to single agent therapies, while minimizing any associated toxicity. These combinations may also increase the efficacy of the conventional agent without increasing the associated toxicity. In particular, we have discovered that in combination with other anti-HIV agents, the compounds of this invention act in an additive or synergistical manner in preventing the replication of HIV in human T cells. Preferred combination therapies include the administration of a compound of this invention with AZT, ddI, ddC, d4T, 3TC, 935U83, 1592U89, 524W91 or a combination thereof.

Alternatively, the compounds of this invention may also be co-administered with other HIV protease inhibitors such as saquinavir (Ro 31-8959, Roche), L-735,524 (Merck), ABT 538 (A-80538, Abbott), AG 1341 (Agouron), XM 412 (DuPont Merck), XM 450 (DuPont Merck), BMS 186318 (Bristol-Meyers Squibb) and CPG 53,437 (Ciba Geigy) or prodrugs of these or related compounds to increase the effect of therapy or prophylaxis against various viral mutants or members of HIV quasi species.

We prefer administering the compounds of this invention as single agents or in combination with retroviral reverse transcriptase inhibitors, such as nucleoside derivatives, or other HIV aspartyl protease inhibitors, including multiple combinations comprising from 3–5 agents. We believe that the co-administration of the compounds of this invention with retroviral reverse transcriptase inhibitors or HIV aspartyl protease inhibitors may exert a substantial additive or synergistic effect, thereby preventing, substantially reducing, or completely eliminating viral replication or infection or both, and symptoms associated therewith.

The compounds of this invention can also be administered in combination with immunomodulators and immunostimulators (e.g., bropirimine, anti-human alpha interferon antibody, IL-2, GM-CSF, interferon alpha, diethyldithiocarbamate, tumor necrosis factor, naltrexone, tuscarasol, and rEPO); and antibiotics (e.g., pentamidine isethiorate) to prevent or combat infection and disease associated with HIV infections, such as AIDS, ARC and HIV-associated cancers.

When the compounds of this invention are administered in combination therapies with other agents, they may be administered sequentially or concurrently to the patient. Alternatively, pharmaceutical compositions according to this invention may comprise a combination of an aspartyl protease inhibitor of this invention and one or more therapeutic or prophylactic agents.

Although this invention focuses on the use of the compounds disclosed herein for preventing and treating HIV infection, the compounds of this invention can also be used as inhibitory agents for other viruses which depend on similar aspartyl proteases for obligatory events in their life cycle. These viruses include other AIDS-like diseases caused by retroviruses, such as simian immunodeficiency viruses, HTLV-I and HTLV-II. In addition, the compounds of this invention may also be used to inhibit other aspartyl proteases, and in particular, other human aspartyl proteases, including renin and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d$\alpha$-tocopherol polyethyleneglycol 1000 succinate, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$-, and $\gamma$-cyclodextrin, or chemically modified derivatives such as hydroxyalkylcyclodextrins, including 2- and 3-hydroxypropyl-$\beta$-cyclodextrins, or other solublized derivatives may also be advantageously used to enhance delivery of comppunds of formula I or II.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide or may be derivatized to bind to a stable resin as a tethered substrate for affinity chromatography applications. For example, a compound of formula I or II may be tethered to an affinity column to purify recombinantly produced HIV protease. Derivatization of the compounds of this invention to produce affinity chromatography resins and the methods used to purify proteases using such resins are well known and within the skill of the art. These and other uses which characterize commercial aspartyl protease inhibitors will be evident to those of ordinary skill in the art. (See: Rittenhouse, J. et al. *Biochem. Biophys. Res. Commun.* 171, p. 60 (1990) and Heimbach, J. C. et al. Ibid 164, p. 955 (1989)).

In order that this invention be more fully understood, the following examples are set forth. These examples are for the purpose of illustration only and are not to be construed as limiting the scope of the invention in any way.

General Materials and Methods

All temperatures are recorded in degrees Celsius. Thin layer chromatography (TLC) was carried out using 0.25 mm thick E. Merck silica gel 60 $F_{254}$ plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Thick layer silica gel chromatography was also carried out using E. Merck 60 $F_{254}$ plates ("prep plates") of 0.5, 1.0, or 2.0 mm thickness. Following development of the plate, the band of silica containing the desired compound was isolated and eluted with an appropriate solvent. Analytical HPLC was carried out using a Water's Delta Pak, 5 µM silica, C18 reversed-phase column, 3.9 mm ID ×15 cm L with a flow rate of 1.5 mL/min using the following table:

| | |
|---|---|
| Mobile phase: | A = 0.1% CF$_3$CO$_2$H in H$_2$O |
| | B = 0.1% CF$_3$CO$_2$H in CH$_3$CN |
| Gradient: | T = 0 min., A (95%), B (5%) |
| | T = 20 min., A (0%), B (100%) |
| | T = 22.5 min., A (0%), B (100%) |

Preparative HPLC was also carried out using C$_{18}$ reversed-phase media. HPLC retention times were recorded in minutes. NMR spectral data was recorded using a Bruker AMX500, equipped with either a reverse or QNP probe, at 500 MHz, and was taken in the indicated solvent.

We have measured the inhibition constants of each compound against HIV-1 protease using the method described essentially by M. W. Pennington et al., *Peptides* 1990, Gimet, E. and D. Andrew, Eds., Escom; Leiden, Netherlands (1990).

Compounds of invention were tested for their antiviral potency in several virological assays. In the first assay, the compounds were added as a solution in dimethylsulfoxide (DMSO) to a test cell culture of CCRM-CEM cells, a strain of CD4$^+$ human T-cell lymphoma cells, previously acutely infected with HIV$_{IIIb}$ using standard protocols (see Meek, T. D. et al., "Inhibition of HIV-1 protease in infected T-lymphocytes by synthetic peptide analogues", *Nature*, 343, p. 90 (1990). Preferred compounds are those which are able to inhibit 90% of viral infectivity at a concentration of 1 μM or less. More preferred compounds are those which are able to inhibit 90% of viral infectivity at a concentration of 100 nM or less.

The effect of the compounds on inhibiting the replication of the virus was measured by determining the HIV extracellular p24 antigen concentration using a commercial enzyme immunoassay (obtained from Coulter Corporation, Hialeah, Fla.).

Depending on the cell type and the desired readout, syncytia formation, reverse-transcriptase (RT) activity, or cytopathic effect as assayed by a dye uptake method may also be used as readouts of antiviral activity. See H. Mitsuya and S. Broder, "Inhibition of the in vitro infectivity and cytopathic effect of human T-lymphotropic virus type III/lymphoadenopathy-associated virus (HTLV-III/LAV) by 2',3'-dideoxynucleosides", *Proc. Natl. Acad. Sci. USA*, vol. 83, pp. 1911–1915 (1986). The effect of compounds of this invention on clinical isolates of other HIV-1 strains was determined by obtaining low-passaged virus from HIV-infected patients and assaying the effect of the inhibitors in preventing infection of the HIV virus in freshly prepared human peripheral blood mononuclear cells (PBMCs).

Insofar as the compounds of this invention are able to inhibit the replication of the HIV virus in human T-cells and furthermore, may be delivered orally to mammals, they are of evident clinical utility for the treatment of HIV infection. These tests are predictive of the compounds ability to inhibit HIV protease in vivo.

SYNTHETIC EXAMPLES

Example 1

A. Compound 1A. 553 mg of (cyclopentyl)methylamine, 1.152 g of 4-methoxybenzenesulfonyl chloride and 0.937 g of sodium bicarbonate were added to a mixture of 10 mL of methylene chloride and 3 mL of saturated, aqueous sodium bicarbonate. The reaction mixture was allowed to stir at room temperature for 3h and diluted with methylene chloride and brine. The organic layer was separated, dried (MgSO$_4$) and concentrated in vacuo to give 1.780 g of Compound 1A as a white solid, which was used without further purification. TLC: Rf=0.60, 5% diethyl ether/methylene chloride; $^1$H NMR consistent with structure.

B. Compound 1B. To 10 mL of DMF was added 0.832 g of the resultant compound of Example 1A, 120 mg of 80% NaH and 508 mg of epibromohydrin at 0° C. The reaction mixture was allowed to stir at room temperature overnight. The reaction mixture was diluted with 300 mL of diethyl ether and washed with water (three times) and brine. The ether solution was dried (MgSO$_4$), filtered and concentrated in vacuo to give to give 0.774 g of Compound 1B as a colorless, viscous oil. TLC: Rf=0.61, 5% diethyl ether/methylene chloride. $^1$H NMR consistent with structure.

C. Compound 1C. 0.213 g of the resultant compound of Example 1B, 0.351 g of benzylamine and 3 mL of MeOH were heated overnight in a sealed tube at 100° C. The reaction mixture was concentrated in vacuo, purified by silica gel chromatography (10% MeOH/methylene chloride) to remove the remaining benzylamine and repurified by silica gel chromatography (8% MeOH/methylene chloride) is to give 87 mg of Compound 1C. TLC: Rf=0.44, 8% MeOH/methylene chloride. $^1$H NMR consistent with structure.

D. Compound XXI. To 5 mL of methylene chloride was added 21 mg of the resultant compound of Example lC, 11.1 mg of 3-(S)-tetrahydrofuranyl succinamidyl carbonate and 18.8 mg of diisopropylethylamine. The reaction mixture was diluted with 50 mL of methylene chloride and the organic layer was washed with 50 mL of 0.5N HCl, 50 mL of saturated, aqueous NaHCO$_3$ and 50 mL 25 of brine. The organic layer was dried over magnesium sulfate and concentrated in vacuo to give 26.4 mg of Compound XXI as a colorless oil. TLC: Rf=0.28, 20% diethyl ether/methylene chloride. HPLC: Rt=16.33 min.

Example 2

Compound XXII. To 5 mL of methylene chloride was added 29 mg of the resultant compound of Example 1C, 7.3 mg of t-butylisocyanate and 19.1 mg of diisopropylethylamine. After 12h, the reaction mixture was concentrated in vacuo, diluted with ethyl acetate, washed with 0.5N HCl, washed with brine, dried (MgSO$_4$) and reconcentrated in vacuo to afford 35.4 mg of Compound XXII as a yellow oil. TLC: Rf=0.15, 5% diethyl ether/methylene chloride; 0.58, 20% diethyl ether/methylene chloride. HPLC: Rt=17.68 min.

Example 3

A. To 2 mL of MeOH was added 198 mg of the resultant compound of Example 1B and 369 mg of phenethylamine. The reaction mixture was heated for 48 h and then allowed to cool to room temperature. The reaction mixture was concentrated in vacuo.and passed through a silica plug (8% MeOH/methylene chloride) to afford 272 mg of Compound 3A as a yellow oil. TLC: Rf=0.48, 8% MeOH/methylene chloride. $^1$H NMR consistent with structure.

B. Compound XXIV. To a mixture of 5 mL of methylene chloride and 2 mL of saturated, aqueous sodium bicarbonate was added 29 mg of the resultant compound of Example 3A, 12.6 mg of benzenesulfonyl chloride and 16 mg of sodium bicarbonate. The reaction mixture was allowed to stir at room temperature for 3 h. The reaction mixture was diluted with methylene chloride. and brine, and the organic layer was separated, dried (MgSO$_4$) and concentrated in vacuo.

Purification by silica gel chromatography (5% diethyl ether/ methylene chloride) gave 25.5 mg of Compound XXIV. TLC: Rf=0.49, 5% diethyl ether/methylene chloride. HPLC: Rt=18.50 min. $^1$H NMR was consistent with structure.

Example 4

A. Sodium hydride (80% dispersion in oil) (0.024 g, 1.100 mmol) was added to a solution of N-cyclopentylmethyl-4-methoxybenzenesulfonamide (0.288 g, 0.847 mmol) in 10 mL of DMF at 0° C. and the mixture was stirred for 0.5 h. (2S)-Glycidyl tosylate (0.232 g, 1.016 mmol) was then added and the mixture was allowed to warm to R.T. and was stirred overnight. The mixture was quenched with MeOH (1 mL) and concentrated in vacuo. The residue was taken up in EtOAc and was washed with water (3×100 mL), dried over MgSO$_4$, and concentrated to give a colorless oil. Purification by silica gel column chromatography (5% Et$_2$O/CH$_2$Cl$_2$) gave epoxide (273 mg, 99%) as a colorless oil. $^1$H NMR consistent with structure.

B. The epoxide prepared in Example 4A (0.093 g, 0.289 mmol) and isobutylamine (0.105 g, 1.43 mmol) in 5 mL of EtOH were heated at 100° C. in a sealed tube for 1 day. The crude material was taken up in MeOH, concentrated, then purified by silica gel column chromatography (8% MeOH/CH$_2$Cl$_2$) to give the amine. $^1$H NMR consistent with structure.

C. The procedure described in Example 1D was performed using the amine prepared in Example 4B (0.047 g, 0.118 mmol). Purification of the crude material by silica gel column chromatography (10–20% Et$_2$O/CH$_2$Cl$_2$) gave Compound 1004 (43 mg, 71%). $^1$H NMR consistent with structure.

Example 5

A. The procedure described in Example 4B was performed using the 86 mg of epoxide and 2-phenethylamine (0.160 g, 1.32 mmol) to give the amine (0.097 g, 82%). $^1$H NMR consistent with structure.

B. The procedure described in Example 4C was performed using the amine prepared in Example 5A (0.024 g, 0.054 mmol) and 1,3-dioxan-4-yl-4-nitrophenyl carbonate (described in Example 29A) (0.018 g, 0.059 mmol) to give Compound 1005 (3.9 mg, 13%). $^1$H NMR consistent with structure.

Example 6

A. The procedure described in Example 1A was performed using isobutylamine (0.396 g, 5.41 mmol) and 3-nitrobenzenesulfonyl chloride (1.0 g, 4.5 mmol) to give N-isobutyl-3-nitrobenzenesulfonamide (0.916 g, 78%). $^1$H NMR consistent with structure.

B. The procedure described in Example 4A was performed using the sulfonamide prepared in Example 6A (0.560 g, 2.17 mmol) to give the epoxide (0.650 g, 95%). $^1$H NMR consistent with structure.

C. The procedure described in Example 5A was performed using the epoxide prepared in Example 6B (0.410 g, 1.30 mmol) to give the amine (0.244 g, 43%). $^1$H NMR consistent with structure.

D. The procedure described in Example 1D was performed using the amine prepared in Example 6C (0.064 g, 0.147 mmol) to give the nitro sulfonamide (0.061 g, 76%). $^1$H NMR consistent with structure.

E. The nitrosulfonamide prepared in Example 6D (0.061 g, 0.110 mmol) and 10 wt. % palladium on carbon (10 mg) in 20 mL of EtOAc was stirred overnight under hydrogen gas. The mixture was filtered, concentrated and chromatographed on a silica gel column (3% MeOH/CH$_2$Cl$_2$) to give Compound 1012 (0.049 g, 85%). $^1$H NMR consistent with structure.

Example 7

A. The procedure described in Example 1A was performed using cyclopentylmethylamine (0.482 g, 4.86 mmol) and 3-nitrobenzenesulfonyl chloride (1.077 g, 4.86 mmol) to give the amine (1.29 g, 93%). $^1$H NMR consistent with structure.

B. The procedure described in Example 4A was performed using the amine prepared in Example 7A (0.727 g, 2.56 mmol) to give the epoxide (1.20 g, crude material). $^1$H NMR consistent with structure.

C. The procedure described in Example 5A was performed using the epoxide prepared in Example 7B (0.216 g, 0.635 mmol) to give the amine (0.142 g, 48%). $^1$H NMR consistent with structure.

D. The procedure described in Example 1D was performed using the amine prepared in Example 7C (0.034 g, 0.074 mmol) and 4-nitrophenyl-tetrahydrofurodihydrofuran-3-yl carbonate (0.033 g, 0.110 mmol) to give the nitro sulfonamide (0.025 g, 55%). $^1$H NMR consistent with structure.

E. The procedure described in Example 6E was performed using the nitro sulfonamide prepared in Example 7D (0.019 g, 0.031 mmol) to give Compound 1013 (0.011 g, 26%). $^1$H NMR consistent with structure.

Example 8

A. The procedure described in Example 5B was performed using the amine prepared in Example 7C (0.039 g, 0.085 mmol) to give the nitro sulfonamide (0.025 g, 50%). $^1$H NMR consistent with structure.

B. The procedure described in Example 6E was performed using the nitro sulfonamide prepared in Example 8A (0.025 g, 0.042 mmol) to give Compound 1014 (0.020 g, 86%). $^1$H NMR consistent with structure.

Example 9

A. The procedure described in Example 4B was performed using 226 mg of the epoxide and 3,4-dibenzyloxyphenethylamine hydrochloride (1.28 g, 3.47 mmol) to give the amine (0.200 g, 44%). $^1$H NMR consistent with structure.

B. The procedure described in Example 1D was performed using the amine prepared in Example 9A (0.076 g, 0.115 mmol) to give the dibenzyl protected sulfonamide (0.057 g, 64%). $^1$H NMR consistent with structure.

C. The dibenzyl protected sulfonamide (0.057 g, 0.074 mmol) was dissolved in EtOAc whereupon a slurry of 10 wt. % palladium on carbon in EtOAc was added. The mixture was stirred overnight at R.T. under an atmosphere of H$_2$. The crude material was purified by prep TLC (2 plates, 0.5 mm SiO$_2$, 3% MeOH/CHCl$_3$) to give Compound 1017 (0.021 g, 61%). $^1$H NMR consistent with structure.

Example 10

Compound XLVIII is synthesized according to Scheme 10:

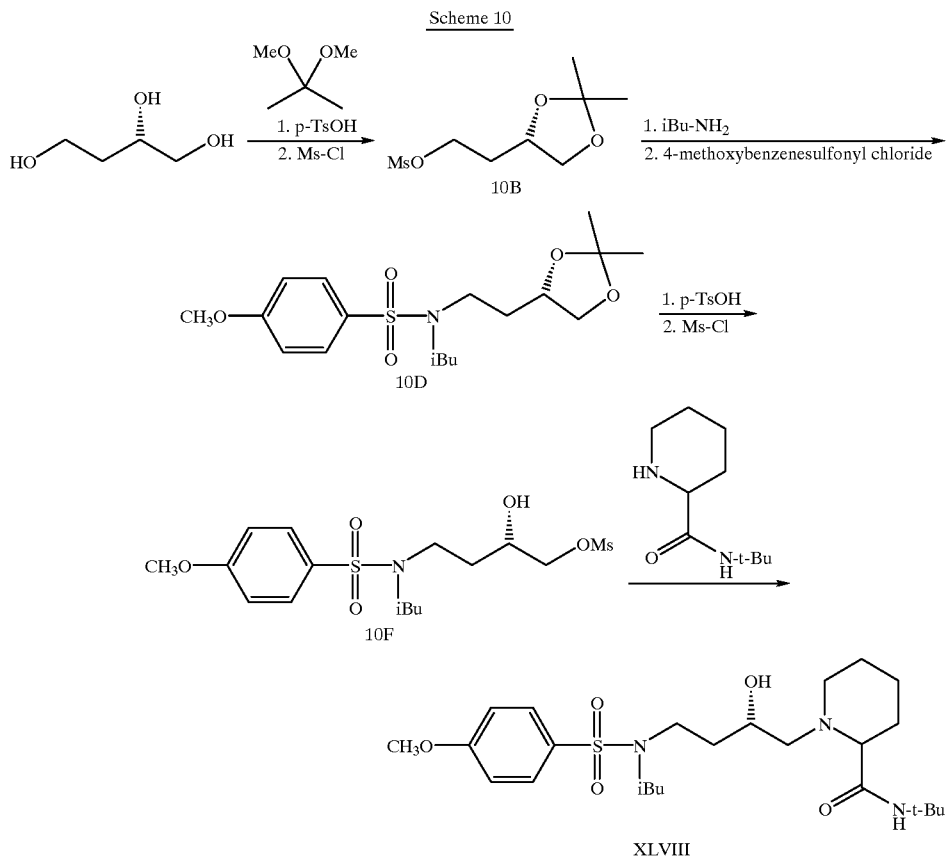

A. Compound 10A. To a solution of 3 mL of (S)-1,2,4-butanetriol and 4.1 mL of 2,2-dimethoxypropane in 10 mL of toluene was added 2 mg of p-toluenesulfonic acid. The reaction mixture was heated at 70° C. for 3 h. After cooling to room temperature, the reaction mixture was diluted with ethyl acetate, washed with brine and dried over magnesium sulfate. Concentration in vacuo gave 3.54 g of Compound 10A. $^1$H NMR consistent with structure.

B. Compound 10E. To a solution of 269.4 mg of the resultant compound of Example 10A in 2 mL of methylene chloride was added 0.35 mL of diisopropylethylamine. The reaction mixture was cooled to −20° C., and to it was added 0.16 mL of methanesulfonyl chloride. The reaction mixture was allowed to warm to room temperature for 0.5 h. The reaction mixture was diluted with 40 mL of methylene chloride and washed with water and brine. The methylene chloride layer was dried (MgSO$_4$), filtered and concentrated in vacuo to give 434.6 mg of Compound 10B as a colorless oil.

C. Compound 10C. A mixture of 154.2 mg of the resultant compound of Example 10B and 1 mL of isobutylamine was allowed to stir at room temperature overnight. After heating at 50° C. for 0.5 h, the reaction mixture was concentrated in vacuo to afford 138.4 mg of Compound 10C as a semi-solid. $^1$H NMR consistent with structure.

D. Compound 10D. To a mixture of 136.8 mg of the resultant compound of Example 10C in 2 mL of methylene chloride and 1 mL of saturated, aqueous sodium bicarbonate was added solid sodium bicarbonate, followed by 210.6 mg of 4-methoxybenzenesulfonyl chloride. The reaction mixture was allowed to stir at room temperature for 0.5 h. The reaction mixture was diluted with methylene chloride and washed with water and brine. The methylene chloride layer was dried over magnesium sulfate and concentrated in vacuo to give 277.4 mg of an almost equimolar mixture of Compound 10D and N-iso-butyl-4-methoxybenzenesulfonamide. TLC: Rf =0.41, 4:1 hexanel-ethyl acetate. $^1$H NMR consistent with structure.

E. Compound 10E. To a solution of 254.4 mg of the resultant mixture of Example 10D in 2 mL of MeOH was added p-toluenesulfonic acid. The reaction mixture was allowed to stir at room temperature until TLC indicated that most of the starting material was consumed. The reaction mixture was concentrated. in vacuo and purified by silica gel chromatography (100% methylene chloride, followed by 50% methylene chloride/ethyl acetate then 100% ethyl acetate) to give 142.4 mg of Compound 10E. TLC: Rf=0.24, 1:1 methylene chloride/ethyl acetate. F. Compound 10F. To a solution of 142.4 mg of the resultant compound of Example 10E in 1 mL of methylene chloride was added 44.7 mmol of methanesulfonyl chloride followed by 1 mL of diisopropylethylamine at −60° C. The reaction was allowed to stir at −60° C. for 10 minutes and to warm to room temperature over 0.5 h. After stirring overnight at room temperature, the reaction mixture was diluted with ethyl acetate and washed with water and brine. The ethyl acetate layer was dried (MgSO$_4$), filtered, concentrated in vacuo and purified by silica gel chromatography (4:1 methylene chloride/ethyl acetate) to give 126.0 mg of Compound 10F. ¹H NMR consistent with structure.

G. Compound XLVIII. A mixture of 126.0 mg of the resultant compound of Example 10F, 68.0 mg of N-t-butyl-L-pipecolinamide and 106 mg of potassium carbonate in 1.5 mL of isopropanol was heated at 80–85° C. overnight. After cooling to room temperature, the reaction mixture was concentrated in vacuo and purified by silica gel chromatography (3:2 methylene chloride/ethyl acetate) to give 113.7 mg of Compound XLVIII. TLC: Rf=0.37, 100% ethyl acetate. HPLC: Rt =13.06 min.

Example 11

Compound LIV is synthesized according to the following scheme:

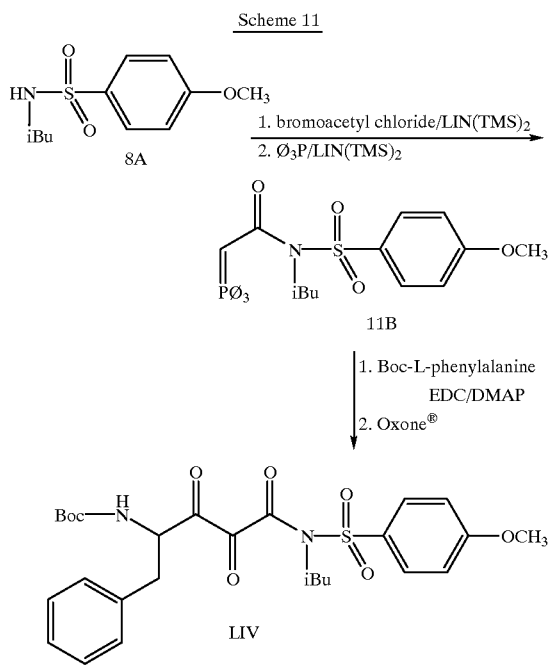

Starting Compound 8A. To a solution of 1.38 g of isobutylamine in methylene chloride was added 3.17 g of sodium bicarbonate, saturated sodium bicarbonate solution and 3.90 g of 4-methoxybenzenesulfonyl chloride. The reaction mixture was allowed to stir at room temperature overnight and diluted with ethyl acetate. The organic phase was washed with 0.5N HCl and brine, and dried (MgSO₄), filtered and concentrated in vacuo to give 4.72 g of Compound 8A.

A. Compound 11A. To a solution of 1 eq. of Compound 8A in dry THF is added 1.1 eq. of lithium bis(trimethylsilyl)amide (1M solution in THF) at 0° C. After 0.5 h, the resulting solution is added dropwise to a solution of 1 eq. of bromoacetyl chloride in THF at 0° C. After an additional 10 min., the reaction mixture is diluted with water. The aqueous mixture is washed with ethyl acetate and combined organic fractions are washed with brine, dried (MgSO₄) and concentrated in vacuo. The resulting residue is purified by silica gel chromatography to give Compound 11A.

B. Compound 11B. To a solution of 1 eq. of the resultant compound of Example 11A in dry toluene is added 1 eq. of triphenylphosphine. The reaction is allowed to stir overnight at 60° C. and gives a triphenylphosphonium salt precipitate. The reaction mixture is cooled to 0° C. and to it is added 1 eq. of lithium bis(trimethylsilyl)amide (1M solution in THF). The reaction mixture is diluted with water and the organic phase is dried (MgSO₄) and concentrated in vacuo. The resulting residue is purified by silica gel chromatography to give Compound 11B.

C. Compound 11C. To a solution of 1 eq. of the resultant compound of Example 11B in dry toluene is added 1 eq. of Boc-L-phenylalanine, 1 eq. of dimethylaminopropylethylcarbodiimide and a catalytic amount of 4-dimethylaminopyridine. After stirring at room temperature until TLC indicates the disappearance of starting material, the reaction mixture is diluted with ethyl acetate and washed with saturated aqueous sodium bicarbonate and brine. The organic phase is dried (MgSO₄) and concentrated in vacuo to give Compound 11C.

D. Compound LIV. To a mixture of 1 eq. of the resultant compound of Example 11C in THF/water (2:1) is added 1.5 eq. of Oxone®. The reaction mixture is stirred at room temperature until TLC indicates a disappearance of starting material. The reaction mixture is diluted with ethyl acetate and concentrated in vacuo. Purification of the resulting residue by silica gel chromatography gives Compound LIV.

Example 12

A. The procedure described in Example 1A was performed using N-(2(S)-hydroxy-4-phenethylamino)butyl-N-isobutyl-4-methoxybenzenesulfonamide (0.043 g, 0.099 mmol) to give Compound 1035. ¹H NMR consistent with structure. R$_f$=0.23 (hexanes:EtOAc, 4:1).

Example 13

Compound XXXIV is synthesized according to scheme 13:

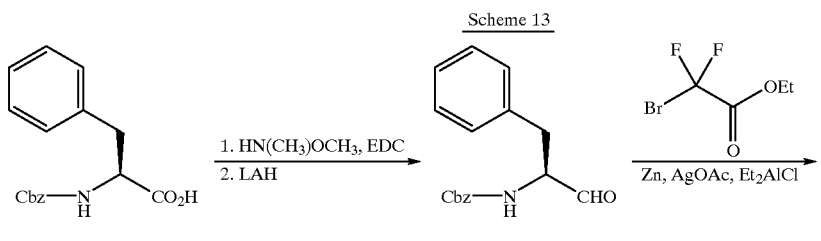

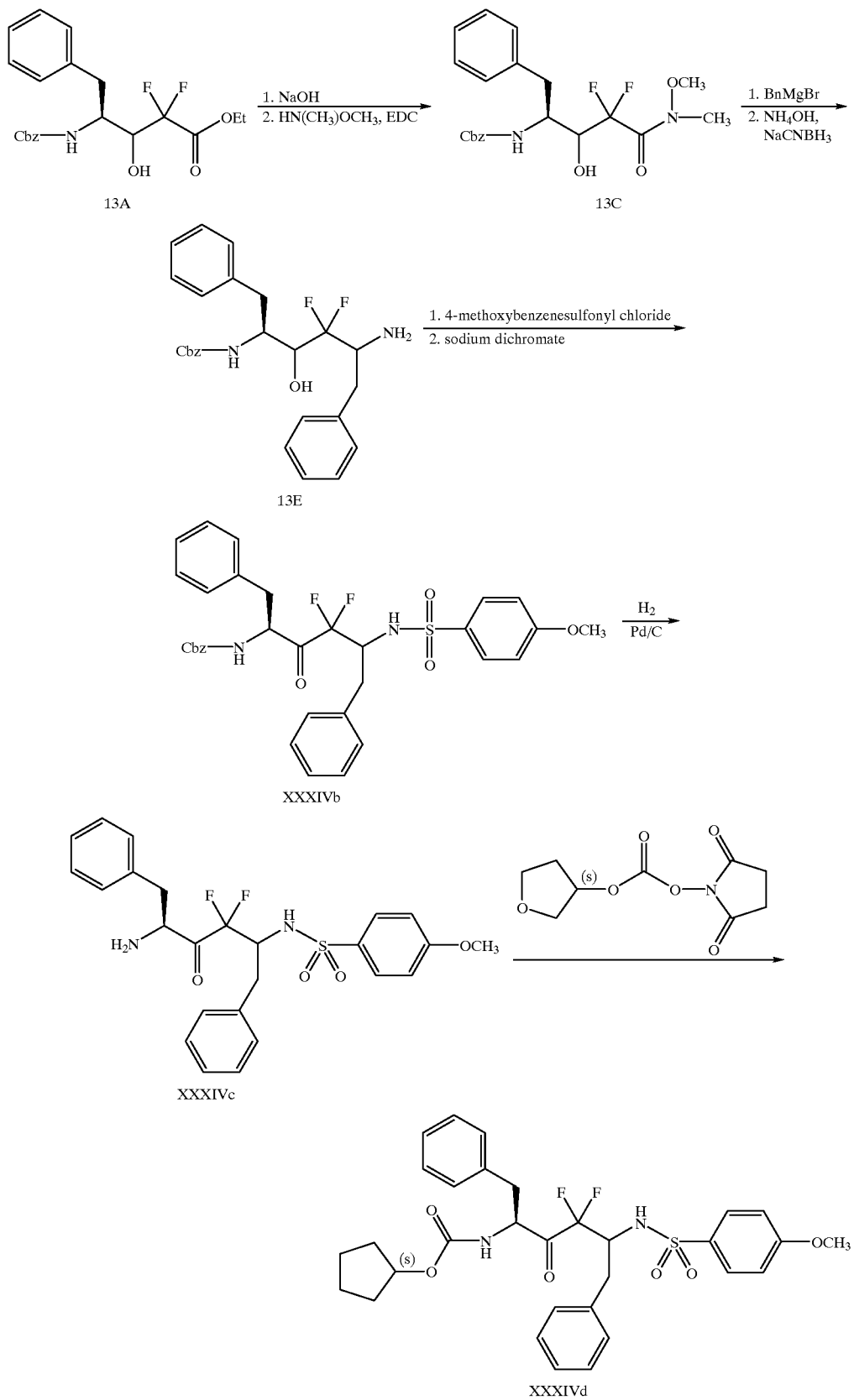

A. Compound 13A. To a solution of 3.2 g of the resultant compound of Example 13K in 20 mL of THF cooled to 0° C. was added 1.84 g of Zn, 0.57 g of AgOAc, 4.6 g of methyl bromodifluoroacetate and 11.3 mmol of diethylaluminum chloride. The reaction mixture was allowed to stir for 3 h at 0° C. and then overnight at room temperature. The reaction mixture was diluted with 10 mL of ethanol, 20 mL of saturated, aqueous ammonium chloride and 30 mL of saturated, aqueous potassium sodium tartrate. The resulting mixture was filtered and the filtrate was washed with 300 mL of ethyl acetate. The ethyl acetate layer was dried over magnesium sulfate, concentrated in vacuo and purified by medium pressure liquid chromatography (100% is methylene chloride followed by 1% MeOH/methylene chloride) to give 3.92 g of Compound 13A.

B. Compound 13B. A methanolic solution of the resultant compound of Example 13A is treated with 1.1 eq. of 1N NaOH. When thin layer chromatography reveals the disappearance of starting material, the reaction mixture is diluted with water and extracted into ethyl acetate. The aqueous layer is acidified to pH 2 with 1N HCl and extracted with ethyl acetate. Concentration in vacuo gives Compound 13B.

C. Compound 13C. The resultant compound of Example 13B is dissolved into THF and to the resulting solution is added 1 eq. of triethylamine, 1 eq. of 1-hydroxybenzotriazole, 1 eq. of EDC and 1 eq. of methoxymethylamine. The reaction is allowed to stir at room temperature. After thin layer chromatography reveals the disappearance of starting material, the reaction mixture is diluted with ethyl acetate and washed with 1N HCl, saturated sodium bicarbonate solution and brine. The organic phase is dried and concentrated in vacuo to give Compound 13C.

D. Compound 13D. To a solution of the resultant compound of Example 13C in THF cooled to 0° C. is added 3–5 eq. of benzylmagnesium chloride. After thin layer chromatography reveals the disappearance of starting material, the reaction mixture is quenched with water and extracted in ethyl acetate. Concentration in vacuo followed by purification by silica gel chromatography gives Compound 13D.

E. Compound 13E. To a solution of the resultant compound of Example 13D in ethanol is added excess ammonium hydroxide and excess sodium cyanoborohydride. The reaction mixture is allowed to stir at room temperature. When thin layer chromatography reveals the disappearance of starting material, the reaction mixture is quenched with water and extracted into ethyl acetate. Concentration of the organic layer in vacuo gives Compound 13E.

F. Compound 13F. The procedure described in Example 10D was performed using the resultant compound of Example 13E to give Compound 13F.

G. Compound XXXIVb. The resultant compound of Example 13F is dissolved in acetic acid and treated with 1 eq. of sodium dichromate. When thin layer chromatography reveals the disappearance of starting material, the reaction mixture is diluted with water and extracted into ethyl acetate. Concentration in vacuo followed by purification by silica gel chromatography gives Compound XXXIVb.

H. Compound XXXIVc. To a solution of the resultant compound of Example 13G in dry ethanol is added under a hydrogen atmosphere Pd/C (10% by weight). The reaction is purged with nitrogen, filtered through Celite® and concentrated in vacuo to give Compound XXXIVc.

I. Compound XXXIVd. To a solution of the resultant compound of Example 13H in methylene chloride is added 1 eq. of 3-(S)-tetrahydrofuranyl succinamidyl carbonate and 1 eq. of diisopropylethylamine. After thin layer chromatography shows the disappearance of starting material, the reaction mixture is concentrated in vacuo and purified by silica gel chromatography to give Compound XXXIVd.

J. Compound 13J. To a solution of 20 g of Cbz-L-phenylalanine in 200 mL of dry THF under nitrogen was added 9.9 g of HOBT, 7.17 g of N-methoxy-N-methylammonium hydrochloride, 14.1 g of EDC and 13.5 g of triethylamine. The reaction mixture was allowed to stir for 60h at room temperature. The reaction mixture was diluted with 200 mL of water, extracted into 1 L of diethyl ether, dried over magnesium sulfate, concentrated in vacuo and purified by medium pressure liquid chromatography (100% methylene chloride, followed by it MeOH/methylene chloride, then 2% MeOH/methylene chloride) to give 19.95 g of Compound 13J.

K. Compound 13K. To a mixture of 1.35 g of lithium aluminum hydride in 250 mL of diethyl ether cooled to –55° C. was added a solution of 10.21 g of the resultant compound of Example 13J in 100 mL of diethyl ether, dropwise, maintaining the reaction temperature below –45° C. The reaction mixture was allowed to stir at –50° C. for 3 h. The reaction mixture was quenched with 200 mL of saturated potassium sodium tartrate solution and was allowed to warm to room temperature. The reaction mixture was diluted with 600 mL of diethyl ether and the organic layer was dried over magnesium sulfate, concentrated in vacuo and purified by medium pressure liquid chromatography (1% MeOH/methylene chloride) to give 5.52 g of Compound 13K.

Example 14

Compound Ld is synthesized according to Scheme 14:

Scheme 14

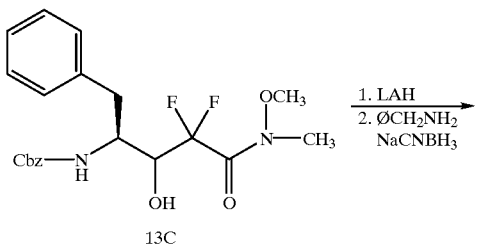

13C

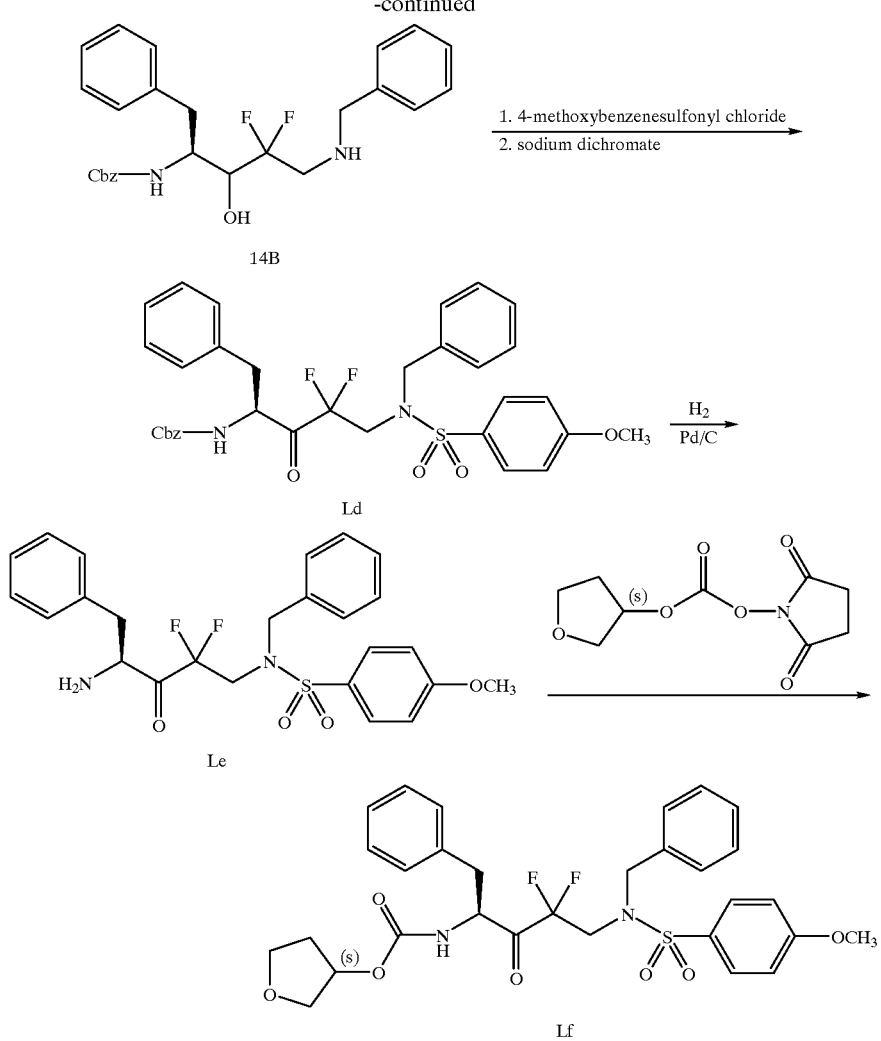

A. Compound 14A. To a solution of the resultant compound of Example 13C in THF cooled to 0° C. is added 1.1 eq. of lithium aluminum hydride. The reaction mixture is quenched with water and extracted into ethyl acetate. Concentration in vacuo gives Compound 14A.

B. Compound 14B. The resultant compound of Example 14A is dissolved in ethanol and treated with an excess of benzylamine and sodium cyanoborohydride. The reaction mixture is worked up as in Example 13E to give Compound 14B.

C. Compound 14C. The resultant compound of Example 14B is treated and worked up as described in Example 13F to give Compound 14C.

D. Compound Ld. The resultant compound of Example 14C is treated and worked up as described in Example 13G to give Compound Ld.

E. Compound Le. The resultant compound of Example 14D is treated and worked up as described in Example 13H to give Compound Le.

F. Compound Lf. The resultant compound of Example 14E is treated and worked up as described in Example 13I to give Compound Lf.

Example 15

A. The procedure described in Example 5B was performed using 30 mg (0.067 mmol) of the amine and 1,3-dioxolan-4-ylmethyl-4-nitrophenyl carbonate (0.045 g, 0.168 mmol) to give Compound 1018 (0.006 g, 14%). $^1$H NMR consistent with structure.

Example 16

A. The procedure described in Example 27K was performed using 4-benzyloxycarbonyl-2(S)-N'-(t-butylcarboxamido)piperazine (0.035 g, 0.110 mmol) to give after prep. TLC (EtOAc/CH$_2$Cl$_2$, 1:1) purification Compound 1031 (0.050 g, 73% for 2 steps). $^1$H NMR consistent with structure.

Example 17

A. Dimethylsulfamoyl chloride (0.022 mL, 0.20 mmol) was added to a solution of N-(2(S)-hydroxy-4-isobutylamino)butyl-N-isobutyl-4-methoxybenzenesulfonamide (0.032 g, 0.08 mmol), sat. aq. NaHCO$_3$ and solid NaHCO$_3$ in CH$_2$Cl$_2$. The mixture was stirred at R.T. overnight then diluted with EtOAc. The is organic phase was washed with water, brine, dried over MgSO$_4$ and concentrated. Purification by prep TLC (15% EtOAc/CH$_2$Cl$_2$) gave Compound 1034 (0.022 g, 55%) as a colorless oil. $^1$H NMR consistent with structure.

Example 18

A. A solution of benzylhydrazine dihydrochloride salt (128 mmol) in CH$_2$Cl$_2$ was treated with di-tert-butyl dicarbonate (170 mmol) and excess of triethylamine (ca. 256 mmol) to give Compound 18A in 90% yield. $^1$H NMR consistent with structure.

B. N-Cyclopentylmethyl-N-glycidyl-3-nitrophenylbenzenesulfonamide (6 mmol) (prepared utilizing the method described in Example 1A using 3-nitrobenzenesulfonyl chloride and subjecting that product to the method described in Example 1B) was treated with neat Compound 18A (43 mmol) at 100° C. for 24 h. The crude materal was purified by silica gel column chromatography (1% MeOH/CH$_2$Cl$_2$ to 5% MeOH/CH$_2$Cl$_2$ to 90:10:1 CH$_2$Cl$_2$/MeOH/NH$_4$OH) to give Compound 18B (1.91 g, 60%). $^1$H NMR consistent with structure.

C. A solution of Compound 18B (0.115 g, 0.20 mmol) in CH$_2$Cl$_2$ was treated with DIEA (0.22 mmol) and benzoyl chloride (0.22 mmol) at 0° C. followed by warming to R.T. The mixture was extracted with EtOAc and the combined extracts washed with 10% aq. HCl, sat. aq. NaHCO$_3$, brine, dried over MgSO$_4$ and concentrated. The crude material was purified by silica gel column chromatography (25% EtOAc/hexanes) to give Compound 18C (0.078 g, 58%). $^1$H NMR consistent with structure.

D. A solution of Compound 18C (0.060 g, 0.10 mmol) was treated with SnCl$_2$ dihydrate (0.50 mmol) in EtOH for 4 h. The mixture was treated with sat. aq. NaHCO$_3$ and extracted with EtOAc. The combined washes were concentrated to give Compound 18D which was used without further purification.

E. A solution of Compound 18D in TFA (1 mL) and CH$_2$Cl$_2$ (2 mL) was stirred 1 h at R.T. The mixture was concentrated and purified by silica gel column chromatography (hexanes/EtoAc, 1:1) to give Compound 1125 (0.030 g, 55% over 2 steps). $^1$H NMR consistent with structure. HPLC: retention time=15.18 min.

Example 19

A. The procedure described in Example 1A was performed using N-(4-cyclopentylmethylamino-2(S)-hydroxy)butyl-N-isobutyl-4-methoxybenzenesulfonamide (0.050 g, 0.121 mmol) and benzenesulfonyl chloride (0.043 g, 0.243 mmol) to give Compound 1122 (0.030 g, 45%). $^1$H NMR consistent with structure.

Example 20

A. The procedure described in Example 1A was performed using N-(4-cyclopentylmethylamino-2(S)-hydroxy)butyl-N-isobutyl-4-methoxybenzenesulfonamide (0.050 g, 0.121 mmol) and 4-benzyloxybenzenesulfonyl chloride (0.069 g, 0.244 mmol) to give Compound 20A (0.047 g, 59%). $^1$H NMR consistent with structure.

B. The procedure described in Example 6E was performed using Compound 20A (0.045 g, 0.068 mmol) to give Compound 1123 (0.035 g, 90%). $^1$H NMR consistent with structure.

Example 21

A. Compound 21A. The resultant compound of Example 27G was treated with isobutylamine in a manner identical to that described in Example 30D to give Compound 21A.

B. Compound XLIVa. The resultant compound of Example 21A was treated with 4-methoxybenzenesulfonyl chloride in a manner identical to that described in Example 10D to give Compound XLIVa. TLC: Rf=0.38, 40% ethyl acetate/hexanes. HPLC: Rt=17.19 min. $^1$H NMR consistent with structure.

Example 22

A. Compound 22A. To a solution of 64.3 mg of the resultant compound of Example 21B in 4.0 mL was added 151.5 mg of triphenylphosphine, 96.5 mg of p-nitrobenzoic acid and 0.577 mmol of diethyl azodicarboxylate. The reaction mixture was allowed to stir at room temperature for 4 days. The reaction mixture was concentrated in vacuo and purified by preparative thin layer chromatography (5% ethyl acetate/hexane) to give 21.2 mg of Compound 22A as a white, foaming solid.

B. Compound XLIVb. To a solution of 21.2 mg of the resultant compound of Example 22A in 1 mL of MeOH was added 0.5 mL of 1M NaOH. The reaction mixture was diluted with 1 mL of THF and was allowed to stir at room temperature for an additional 3 h. The reaction mixture was concentrated in vacuo and purified by preparative thin layer chromatography (95:5 methylene chloride/ethyl acetate) to give 10.5 mg of pure compound XLIVb. TLC: Rf=0.38, 60:40 hexane/ethyl acetate. HPLC: Rt=17.20 min.

Example 23

A. The procedure described in Example 17A was performed using 3-nitrobenzenesulfonyl chloride (0.036 g, 0.161 mmol) and N-(4-cyclopentylmethylamino-2(S)-hydroxy)butyl-N-isobutyl-4-methoxybenzenesulfonamide (0.044 g, 0.108 mmol) to give the nitro sulfonamide in quantitative yield.

B. The procedure described in Example 6E was performed using the nitro sulfonamide prepared in Example 23A (0.064 g, 0.108 mmol) to give Compound 1041 (0.024 g, 39%). $^1$H NMR consistent with structure.

Example 24

A. The procedure described in Example 1A was performed using N-(4-cyclopentylmethylamino-2(S)-hydroxy)butyl-N-isobutyl-4-methoxybenzenesulfonamide (0.075 g, 0.182 mmol) and 4-nitrobenzenesulfonyl chloride (0.081 g, 0.365 mmol) to give Compound 24A (0.074 g, 68%). $^1$H NMR consistent with structure.

B. The procedure described in Example 6E was performed using Compound 24A (0.040 g, 0.067 mmol) to give Compound 1124 (0.025 g, 66%). $^1$H NMR consistent with structure.

Example 25

Compound LXXVI. The resultant compound of Example 10F is treated with 4-(benzyloxycarbonyl)-2-(S)-N'-(t-butylcarboxamido)-piperazine in a manner similar to that described in Example 10G to give Compound LXXVI.

Example 26

A. Compound 26A. To a solution of 1.61 g of 4-nitrobenzyl chloroformate in 20 mL of methylene chloride cooled to 0° C. was added 0.83 g of glycerol formal (prepared according to the method described in J-L. Gras et al., Tett. Lett., 28, p. 6601 (1987)) and 0.9 mL of N-methylmorpholine. The reaction mixture was allowed to stir at room temperature overnight. The reaction mixture was diluted with ethyl acetate, washed with water, 0.5N HCl and brine, dried over magnesium sulfate and concentrated in vacuo. The resulting residue was recrystallized from methylene chloride/hexane to give 0.80 g of Compound 26A.

B. Compound LXVIII. The resultant compound of Example 13H is treated with the resultant compound of Example 26A in a manner similar to that described in Example 13I to give Compound LXVIII.

Example 27

A. Compound 27A. To a solution of 1.04 g of the resultant compound of Example 10A in 7 mL of THF was added 0.28 g of NaH at 0° C. After 5 min., 0.85 mL of benzyl bromide was added to the reaction mixture. After an additional 4 h, the reaction mixture was diluted with 150 mL of diethyl ether and washed with water (two times) and brine. The organic phase was dried (MgSO$_4$) and concentrated in vacuo. The resulting residue was purified by silica gel chromatography (10% ethyl acetate/hexane followed by 20% ethyl acetate/hexane) to give 1.15 g of Compound 27A.

B. Compound 27B. To a solution of 1.15 g of Compound 27A in 8 mL of MeOH was added 0.2 g of p-toluenesulfonic acid. The reaction mixture was allowed to stir for 60 h at room temperature. The reaction mixture was concentrated in vacuo, diluted with methylene chloride and washed with water and brine. The organic layer was dried over MgSO$_4$ and concentrated in vacuo to give 1.47 g of Compound 27B.

C. Compound 27C. To a mixture of 110.9 mg of Compound 27B in 1.0 mL of methylene chloride cooled to −78° C. was added 0.25 mL of diisopropylethylamine, followed by 0.565 mmol of methanesulfonyl chloride. The reaction mixture was allowed to warm to room temperature and was concentrated in vacuo to give a mixture of Compound 27C and the product of bis-mesylation.

D. Compound 27D. A solution of 1.25 g of Compound 27C and 4.0 mL of isobutylamine was heated for 6 h at 60° C. and was allowed to stir at room temperature overnight. The reaction mixture was concentrated in vacuo to give Compound 27D as a light, yellow semi-solid.

E. Compound 27E. The procedure described in Example 10D was performed using 1.145 g of Compound 27D (purification by silica gel chromatography: methylene chloride followed by 5% ethyl acetate/methylene chloride) to give 0.976 g of pure compound 27E. TLC: Rf=0.42, 60:40 hexane/ethyl acetate.

F. Compound 27F. To a 200 mL round bottom flask containing 5 mL of MeOH was added 0.103 g of 10% Pd/C followed by a 25 mL solution of 0.976 g of Compound 27E in MeOH. The flask was fitted with a hydrogen-filled balloon and was allowed to stir for 60 h at room temperature. The reaction mixture was filtered, concentrated in vacuo and purified by silica gel chromatography (3:2 ethyl acetate/methylene chloride) to give 0.6497 g of Compound 27F as a thick, colorless oil.

G. Compound 27G. To a 1 mL solution of 90.5 mg of Compound 27F in methylene chloride was added 0.410 mmol of diisopropylethylamine. The reaction mixture was cooled to −78° C., whereupon 0.273 mmol of methanesulfonyl chloride were added. The reaction mixture was allowed to warm to room temperature and was concentrated in vacuo to give 111.8 mg of Compound 27G.

H. Compound 27H. To a solution of 3.23 g of Compound 27E in 10 mL of diethyl ether was added 3.5 mL of 3,4-dihydro-2H-pyran. The reaction mixture was allowed to stir at room temperature for 60 h. The reaction mixture was diluted with ethyl acetate, washed with water (two times) and brine, dried over magnesium sulfate and concentrated in vacuo to give 4.01 g of Compound 27H as a colorless oil. $^1$H NMR consistent with structure.

I. Compound 27I. To a solution of 3.87 g of Compound 27H in 30 mL of MeOH was added 800 mg of 10% Pd/C. The reaction mixture was placed in a hydrogenating apparatus under a pressure of 35 psi. After 6 h, more catalyst was added and the pressure was increased to 45 psi. The hydrogenolysis was allowed to proceed overnight, whereupon still more catalyst was added. The reaction was allowed to proceed at 42 psi overnight. The reaction mixture was filtered and concentrated in vacuo to give 3.33 g of Compound 27I as a thick, colorless oil. $^1$H NMR consistent with structure.

J. Compound 27J. To a solution of 0.66g of Compound 27I in 4 mL of DMF was added 2.09 g of pyridinium dichromate. The reaction mixture was allowed to stir at room temperature overnight. The reaction mixture was poured into 15 mL of water and extracted into diethyl ether (five times). The combined organic layers were washed with brine, dried over magnesium sulfate, filtered and concentrated in vacuo to give a colorless oil. The resulting colorless oil was purified by medium pressure liquid chromatography to give 0.19 of Compound 27J.

K. Compound LXXXII. To a solution of Compound 27J in DMF is added 1 eq. of S-thiaproline t-butylamide, 1 eq. of EDC and 1 eq. of HOBT. The reaction mixture is diluted with ethyl acetate and washed with saturated, aqueous sodium bicarbonate and brine. The organic phase is concentrated in vacuo and purified by silica gel chromatography to give a THP-protected product. The THP-protected product is dissolved in MeOH and treated with catalytic p-toluenesulfonic acid. The reaction mixture is concentrated in vacuo and purified by silica gel chromatography to give Compound LXXXII.

Example 28

A. Compound 28A. To a solution of 2.0607 g of S-(+)-5-trityloxymethyl-gamma-butyrolactone in 1 mL of THF cooled to −78° C. was added 5.749 mmol of LiN(TMS)$_2$ as a 1M solution in THF. The reaction mixture was allowed to stir for 0.5 h, whereupon 5.75 mL of benzyl bromide were added. The reaction mixture was allowed to stir overnight. The reaction mixture was quenched with 0.5N HCl, extracted into ethyl acetate, concentrated in vacuo and purified by silica gel chromatography (20% ethyl acetate/hexane) to give 0.8834 g of Compound 28A.

B. Compound 28B. To a solution of 0.1899 g of the resultant compound of Example 28A in 1 mL of methylene chloride was added approximately 3 mL of trifluoracetic acid. The reaction mixture was allowed to stir at room temperature for 2 h. The reaction mixture was concentrated in vacuo and purified by silica gel chromatography (100% methylene chloride followed by 20% diethyl ether/methylene chloride) to give 47.5 mg of Compound 28B.

C. Compound 28C. To a solution of 47.5 mg of the resultant compound of Example 28B in methylene chloride cooled to −10° C. was added 0.0443 mL of triethylamine and 0.023 mL of methanesulfonyl chloride. The reaction mixture was allowed to stir overnight at room temperature. The reaction mixture was concentrated in vacuo to give Compound 28C.

D. Compound 28D. To the resultant compound of Example 28C was added excess iso-butylamine. The reaction mixture was allowed to stir at room temperature overnight. The reaction mixture was concentrated in vacuo to give Compound 28D.

E. Compound LI'. The procedure described in Example 10D was performed using the resultant compound of Example 28D (purification by silica gel chromatography: 0–10% diethyl ether/methylene chloride) to give 22.7 mg of Compound LI'. ¹H NMR consistent with structure. TLC: Rf=0.32, 10% diethyl ether/methylene chloride.

Example 29

A. Benzyl chloroformate (0.919 g, 5.38 mmol) was added to a solution of cyclopentylmethylamine (0.445 g, 4.49 mmol) and DIEA (1.74 g, 13.5 mmol) in 50 mL of $CH_2Cl_2$ and the mixture was strried overnight at R.T. The mixture was concentrated in vacuo and the residue was taken up in EtOAc, washed with water, sat. aq. $NaHCO_3$, brine, dried over $MgSO_4$ and concentrated to give the crude N-Cbz-cyclopentylmethylamine (1.275 g) which was used without further purification. ¹H NMR consistent with structure.

B. The procedure described in Example 4A was performed using N-Cbz-cyclopentylmethylamine (1.275 g, crude material) to give the epoxide (0.517 g, 40%). ¹H NMR consistent with structure.

C. The procedure described in Example 5A was performed using the epoxide prepared in Example 29B (0.260 g, 0.899 mmol) to give the amine (0.200 g, 54%). ¹H NMR consistent with structure.

D. The procedure described in Example 29A was performed using isonicotinoyl chloride hydrochloride (0.077 g, 0.435 mmol) and the amine prepared in Example 29C (0.119 g, 0.290 mmol) to give the Cbz-amine. ¹H NMR consistent with structure.

E. The procedure described in Example 6E was performed using the Cbz-amine prepared in Example 29D (0.039 g, 0.071 mmol) to give the free amine (0.036 g, crude material) which was used without further purification. ¹H NMR consistent with structure.

F. 3-nitrobenzenesulfonyl chloride (0.025 g, 0.113 mmol) was added to a solution of the amine prepared in Example 29E (0.036 g, crude material) and DIBA (0.037 g, 0.28 mmol) in 10 mL of $CH_2Cl_2$ and the mixture was stirred overnight at R.T. The mixture was concentrated in vacuo and the residue was taken up in EtOAc, washed with water, sat. aq. $NaHCO_3$, brine, dried over $MgSO_4$ and concentrated. Purification by silica gel column chromatography (3% MeOH/$CH_2Cl_2$) gave the nitro sulfonamide (0.011 g, 28% over 2 steps). ¹H NMR consistent with structure.

G. The procedure described in Example 6E was performed using the nitro sulfonamide prepared in Example 29F (0.011 g, 0.020 mmol) to give Compound 1045 (0.006 g, 59%). ¹H NMR consistent with structure.

Example 30

A. A 1.6M solution of n-BuLi in hexanes (0.705 mL, 1.13 mmol) was added to a solution of (S)-(–)-4-benzyl-2-oxazolidinone (0.200 g, 1.13 mmol) in 10 mL of THF at −78° C. After 20 min., epibromohydrin (0.139 g, 1.02 mmol) was added. The mixture was-stirred 30 min. then was allowed to warm to R.T. and stirred for 2 days. The mixture was quenched with MeOH and concentrated. The residue was taken up in EtOAc and washed with sat. aq. $NaHCO_3$, brine, dried over $MgSO_4$ and concentrated. The crude material was purified by silica gel column chromatography (5% $Et_2O/CH_2Cl_2$) to give the epoxide (0.024 g, 9%). ¹H NMR consistent with structure.

B. The procedure described in Example 1C was performed using the epoxide prepared in Example 30A (0.024 g, 0.102 mmol) and cyclopentylmethylamine (0.051 g, 0.515 mmol) to give the amine (0.034 g, quant.). ¹H NMR consistent with structure.

C. The procedure described in Example 29F was performed using 4-methoxybenzenesulfonyl chloride (0.032 g, 0.153 mmol) and the amine prepared in Example 30B (0.034 g, 0.102 mmol) to give two separable diastereomers ($SiO_2$, 3×0.5 mm plates, 5% MeOH/$CH_2Cl_2$) Compound 1046A (0.018 g, $R_f$=0.51, 5% MeOH/$CH_2Cl_2$) and Compound 1046B (0.018 g, $R_f$=0.45, 5% MeOH/$CH_2Cl_2$) which gave a combined yield of 65%. ¹H NMR consistent with structures.

Example 31

A. The procedure described in Example 4A was performed using 4-phenyl-1,2,3,4-tetrahydroisoquinolinone (0.028 g, 0.143 mmol) to give the epoxide. ¹H NMR consistent with structure.

B. The procedure described in Example 30B was performed using the epoxide prepared in Example 31A to give the amine (0.008 g). ¹H NMR consistent with structure.

C. The procedure described in Example 30C was performed using the amine prepared in Example 31B to give Compound 1048 (0.002 g, 21%, $R_f$=0.36, 3% MeOH/$CH_2Cl_2$).

Example 32

Using the method described by Pennington et al. (supra), we obtained inhibition constants for the following compounds of this invention:

| Compound | $K_i$ (nM) |
| --- | --- |
| XLII | 2,400 |
| XLIVa | 400 |
| XLVIII | 3,300 |
| XLV | 160 |
| LVa | 167 |
| LI | 5,000 |
| LII | 11 |
| LXXVI | 2,700 |
| 1000 | 100 |
| 1001 | 30 |
| 1002 | 16,000 |
| 1003 | 1,200 |
| 1004 | 1,300 |
| 1005 | 15 |
| 1006 | 470 |
| 1007 | 35 |
| 1008 | 260 |
| 1009 | 120 |
| 1010 | 125 |
| 1011 | 110 |
| 1012 | 200 |
| 1013 | 50 |
| 1014 | 130 |
| 1015 | 17 |
| 1016 | 75 |
| 1017 | 110 |
| 1018 | 65 |
| 1019 | 20 |
| 1020 | 170 |
| 1021 | 70 |
| 1022 | 170 |
| 1023 | 52 |
| 1024 | 66 |
| 1025 | 270 |
| 1026 | 20 |
| 1027 | 7 |
| 1028 | 800 |
| 1029 | 3,500 |
| 1031 | 1,400 |
| 1033 | 1,600 |
| 1034 | 1,100 |
| 1035 | 3,600 |
| 1036 | 8,000 |
| 1037 | >10,000 |
| 1038 | >10,000 |

-continued

| Compound | $K_i$ (nM) |
|---|---|
| 1039 | >3,000 |
| 1040 | >10,000 |
| 1041 | 270 |
| 1044 | 220 |
| 1045 | 14 |
| 1046 | 1,200 |
| 1047 | 1,600 |
| 1048 | 3,300 |

While we have described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:

1. A compound of formula I:

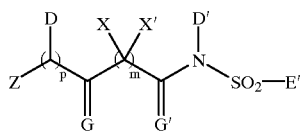

(I)

wherein:
each Z is selected from the group consisting of —N(D)SO$_2$E; —N(H)A; —N(D)A; —N(H)E; —N(H)C(O)N(D)(E); —N(H)—Ht; —Ht and —N(D)—Ht; where Z may not be phthalimidyl;

each A is independently selected from the group consisting of Ht; —R$^1$—Ht;

each Ht is a heterocycle selected from the group consisting of benzimidazolyl, imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, oxazolyl, benzoxazolyl, oxopiperidinyl, oxopyrroldinyl, oxoazepinyl, azepinyl, isoxazolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetrahydrofurofuranyl and tetrahydropyranofuranyl; wherein any member of said Ht may be optionally substituted with one or more substituents, the same or different, selected from the group consisting of oxo, —OR$^2$, —R$^2$, —N(R$^2$) (R$^2$), —NHOH, —R$^2$—OH, —CN, —CO$_2$R$^2$, —C(O)—N(R$^2$) (R$^2$), —S(O)$_2$—N(R$^2$)(R$^2$), —N(R$^2$)—C(O)—R$^2$, —C(O)—R$^2$, —S(O)$_n$—R$^2$, —OCF$_3$, —S(O)$_n$—D, —N(R$^2$)—S(O)$_2$(R$^2$), halo, —CF$_3$, —NO$_2$, —R$^6$, —O—R$^6$, —C(O)N(D)(D) and —C(O)N(H)D;

each D and D' is independently selected from the group consisting of R$^6$; —N(R$^2$) (R$^2$); C$_1$-C$_6$ alkyl, which may be optionally substituted with one or more groups, the same or different, selected from C$_3$-C$_6$ cycloalkyl, —OR$^2$, —R$^3$, —O—R$^6$, —S—R$^6$ and R$^6$; C$_2$-C$_4$ alkenyl, which may be optionally substituted with one or more groups, the same or different, selected from the group consisting of C$_3$-C$_6$ cycloalkyl, —OR$^2$, —R$^3$, —O—R$^6$ and R$^6$; C$_3$-C$_6$ cycloalkyl, which may be optionally substituted with or fused with R$^6$; and C$_5$-C$_6$ cycloalkenyl, which may be optionally substituted with or fused with R$^6$; where D' may not be unsubstituted methyl, unsubstituted ethyl, unsubstituted phenyl, or phenyl substituted with chloro, acetamido, carbamoylmethyl or allyloxy;

each E and E' is independently selected from the group consisting of Ht; —O—Ht; Ht—Ht;

each R$^1$ is independently selected from the group consisting of —C(O)—, —S(O)$_2$—, —C(O)—C(O)—, —O—C(O)—, —O—S(O)$_2$, —NR$^2$—S(O)$_2$—, —NR$^2$—C(O)— and —NR$^2$—C(O)—C(O)—;

each R$^2$ is independently selected from the group consisting of H, R$^6$, and C$_1$-C$_4$ alkyl optionally substituted with R$^6$; wherein when R$^2$ is a linker between two radicals, R$^2$ may not be H;

each R$^3$ is independently selected from the group consisting of H, Ht, C$_1$-C$_6$ alkyl and C$_2$-C$_6$ alkenyl wherein any member of said R$^3$, except H, may be optionally substituted with one or more substituents, the same or different, selected from the group consisting of —OR$^2$, —C(O)—NH—R$^2$, —S(O)$_n$—N(R$^2$)(R$^2$), Ht, —CN, —SR$^2$, —CO$_2$R$^2$, NR$^2$—C(O)—R$^2$;

each R$^5$ is independently selected from the group consisting of H and C$_1$-C$_3$ alkyl;

each R$^6$ is independently selected from the group consisting of aryl, carbocycle and Ht, wherein said carbocycle or Ht may be optionally substituted with one or more groups, the same or different, selected from the group consisting of oxo, —OR$^5$, —R$^5$, —N(R$^5$) (R$^5$), —N(R$^5$)—C(O)—R$^5$, —R$^{15}$—OH, —CN, —CO$_2$R$^5$, —C(O)—N(R$^5$) (R$^5$), halo and —CF$_3$;

each R$^{15}$ is independently selected from the group consisting of divalent C$_1$-C$_3$ alkyl;

each n is independently 1 or 2;

m is an integer selected from 1, 2 and 3;

p is an integer selected from 0 and 1;

each G and G' is independently selected from the group consisting of H$_2$ and O; and each X and X' is independently selected from the group consisting of hydrogen; —OH; —NH$_2$; SH; D; halogen and, if X and X' are taken together, oxygen.

2. The compound according to claim 1, wherein E' is Ht—Ht.

3. The compound according to claim 1 or 2 having the structure of formula IV:

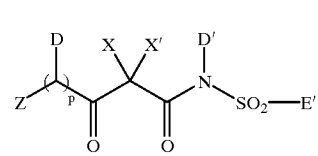

(IV)

4. The compound according to claim 3, wherein:
each D and D' is independently selected from the group consisting of C$_1$-C$_6$ alkyl, which may be optionally substituted with R$^6$;

each E' is independently selected from Ht;

each Z is independently selected from the group consisting of —N(D)SO₂E; —N(H)Ht; —N(H)A; —N(D)A and —Ht;

each Ht is a heterocycle selected from the group consisting of benzimidazolyl, imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, oxazolyl, benzoxazolyl, oxopiperidinyl, oxopyrroldinyl, oxoazepinyl, azepinyl, isoxazolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetrahydrofurofuranyl and tetrahydropyranofuranyl, wherein any member of said Ht may be optionally substituted with one or more substituents, the same or different, selected from the group consisting of —OR², R², —N(R²) (R²), —N₂, —C(O)N (R²) (R²) and S(O)ₙ—R⁶;

each X and X' is independently selected from the group consisting of H, —OH and, if X and X' are taken together, oxygen;

each A is independently selected from the group consisting of —R¹—Ht; and each R¹ is independently selected from the group consisting of —C(O)— and —O—C(O)—.

5. The compound according to claim 1 or 2 having the structure of formula VI:

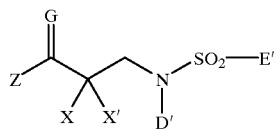

(VI)

6. The compound according to claim 5, wherein:

each D and D' is independently selected from the group consisting of C₁-C₆ alkyl, which may be optionally substituted with R⁶;

each X and X' is independently selected from the group consisting of H, OH, and if X and X' are taken together, oxygen;

each Z is selected from the group consisting of —N(D)SO₂E; —N(H)Ht; —N(H)A; —N(D)A and —Ht;

each Ht is a heterocycle selected from the group consisting of benzimidazolyl, imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, oxazolyl, benzoxazolyl, oxopiperidinyl, oxopyrroldinyl, oxoazepinyl, azepinyl, isoxazolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetrahydrofurofuranyl and tetrahydropyranofuranyl, and wherein any member of said Ht may be optionally substituted with one or more substituents, the same or different, selected from the group consisting of —OR², R², —N(R²) (R²), —NO₂, —C(O)N(R²) (R²) and —S(O)ₙ—R⁶;

each A is selected from the group consisting of —R¹—Ht; and each R¹ is independently selected from the group consisting of —C(O)— and —O—C(O)—.

7. The compound according to claim 6 having the structure of formula CIII:

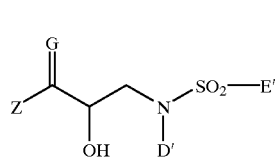

(CIII)

8. The compound according to claim 7 having the structure of formula LVIIa:

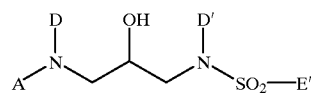

(LVIIa)

wherein:

each A is selected from the group consisting of —R¹—Ht; and each R¹ is independently selected from the group consisting of —C(O)— and —O—C(O)—.

9. The compound according to claim 8, wherein each D and D' are independently selected from the group C₁-C₆ alkyl, which may be optionally substituted with R⁶.

10. The compound according to claim 7 having the structure of formula LVIIb:

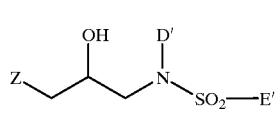

(LVIIb)

wherein Z is selected from the group consisting of:

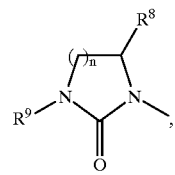

-continued

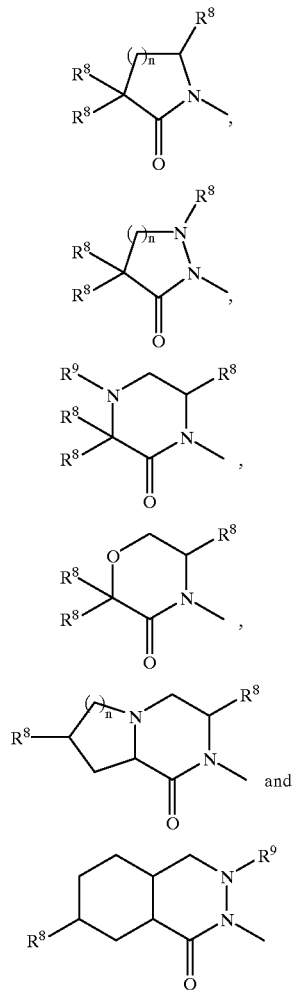

wherein R[8] is selected from the group consisting of R[2], —N—C(O)—O—R[2] and —N—C(O)—R[2]; R[9] is selected from the group consisting of R[2], —C(O)—O—R[2] and —C(O)—R[2] and R[2] is as defined in claim 1.

11. The compound according to claim 10, wherein D and D' are each independently $C_1$-$C_6$ alkyl which may be optionally substituted with R[6].

12. The compound according to claim 1 or 2 having the structure of formula VII:

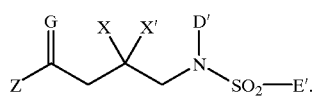
(VII)

13. The compound according to claim 12, wherein:
each D and D' is $C_1$-$C_6$ alkyl, which may be optionally substituted with R[6];
G is $H_2$;
each X and X' is independently selected from the group consisting of H, OH, and if X and X' are taken together, oxygen;
each E' is independently selected from Ht;
each R[1] is selected from the group consisting of —C(O)— and —O—C(O)—;

each Z is selected from the group consisting of —N(H)Ht; —N(H)A; —N(D)SO$_2$E; —N(D)A and —Ht;

each Ht is a heterocycle selected from the group consisting of benzimidazolyl, imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, oxazolyl, benzoxazolyl, oxopiperidinyl, oxopyrrolidinyl, oxoazepinyl, azepinyl, isoxazolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetrahydrofurofuranyl and tetrahydropyranofuranyl, and wherein any member of said Ht may be optionally substituted with one or more substituents, the same or different, selected from the group consisting of —OR[2], R[2], —N(R[2]) (R[2]), —NO$_2$, —C(O)N(R[2]) (R[2]) and —S(O)$_n$—R[6]; and
each A is selected from the group consisting of —R[1]—Ht.

14. The compound according to claim 12 having the structure of formula CIV:

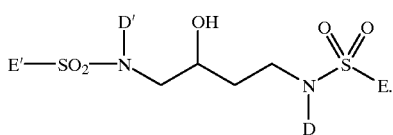
(CIV)

15. The compound according to claim 1 or 2 having the structure of formula C:

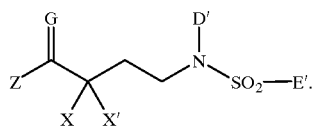
(C)

16. The compound according to claim 15, wherein Z is selected from the group consisting of —N(H)Ht; —N(H)A; —N(D)A and —Ht.

17. The compound according to claim 1 having the structure of formula CI:

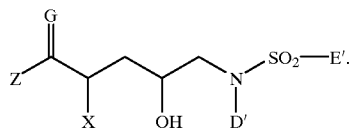
(CI)

18. The compound according to claim 17, wherein X is a $C_1$ alkyl substituted with $R^6$ and D' is a $C_1$–$C_4$ alkyl optionally substituted with $R^6$.

19. A process for producing a compound according to claim 1, comprising:

a first step comprising adding to an amine having the formula D'—$NH_2$, one of either Hal—$SO_2$—E or

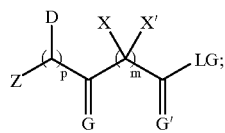

a second step comprising adding to the product of the first step, the other of either Hal—$SO_2$—E or.

20. A pharmaceutical composition comprising a pharmaceutically effective amount of a compound according to claim 1, and a pharmaceutically acceptable carrier, adjuvant or vehicle.

21. The pharmaceutical composition according to claim 20, wherein said pharmaceutical composition is orally administrable.

22. A method for treating HIV infection in a mammal comprising the step of administering to said mammal a pharmaceutical composition comprising a pharmaceutically effective amount of a compound of formula I according to claim 1:

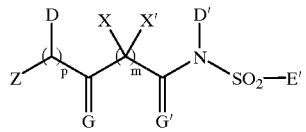

wherein:
each Z is selected from the group consisting of —N(D)$SO_2$E; —N(H)A; —N(D)A; —N(H)E; —N(H)C(O)N(D)(E); —N(H)—Ht; —Ht and —N(D)—Ht;

each D and D' is independently selected from the group consisting of $R^6$; —N($R^2$)($R^2$); $C_1$–$C_6$ alkyl, which may be optionally substituted with one or more groups, the same or different, selected from $C_3$–$C_6$ cycloalkyl, —$OR^2$, —$R^3$, —O—$R^6$, —S—$R^6$ and $R^6$; $C_2$–$C_4$ alkenyl, which may be optionally substituted with one or more groups, the same or different, selected from the group consisting of $C_3$–$C_6$ cycloalkyl, —$OR^2$, —$R^3$, —O—$R^6$ and $R^6$; $C_3$–$C_6$ cycloalkyl, which may be optionally substituted with or fused with $R^6$; and $C_5$–$C_6$ cycloalkenyl, which may be optionally substituted with or fused with $R^6$; and A, Ht, E and E', $R^1$, $R^2$, $R^3$, $R^4$, $R^5$, $R^6$, $R^{15}$, n, m, p, G and G', and X and X' are as defined in claim 1; and a pharmaceutically acceptable carrier, adjuvant or vehicle.

23. The method according to claim 22, wherein said pharmaceutical composition is orally administrable.

* * * * *

UNITED STATES PATENT AND TRADEMARK OFFICE
CERTIFICATE OF CORRECTION

PATENT NO.     : 6,127,372
DATED          : October 3, 2000
INVENTOR(S)    : Tung et al.

It is certified that error appears in the above-identified patent and that said Letters Patent is hereby corrected as shown below:

Title page,
Item [56], References Cited, under OTHER PUBLICATIONS,
In "M. Cushman", delete "Delvelopment" and substitute therefor -- Development --.
In "Baker et al." delete "anitmalarial" and substitute therefor -- antimalarial --.

Column 3,
Line 1, delete "N (HTHt;" and substitute therefor -- -N (H) -Ht; --.
Line 24, delete "-D-Ht," and substitute therefor -- -O-Ht, --.

Column 5,
Line 50, delete "i592U89" and substitute therefor -- 1592U89 --.

Column 6,
Line 28, delete "S-carbolinyl," and substitute therefor -- β -carbolinyl, --.

Column 10,
Line 1, delete "-$NR^2$-S (O)$^2$-," and substitute therefor -- -$NR^2$-S (O)$_2$-, --.

Column 11,
Line 56, delete "Het." and substitute therefor -- Ht. --.

Column 15,
Line 39, delete "is".

Columns 23-24,
Table 1, compound 1011, under column entitled "$R^7$" delete "4-OCH$_2$" and substitute therefor -- 4-OCH$_3$ --.

Columns 35-49,
Table 2, delete each occurrence of 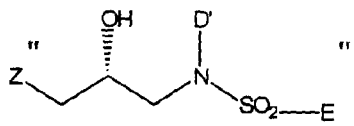

and substitute therefor 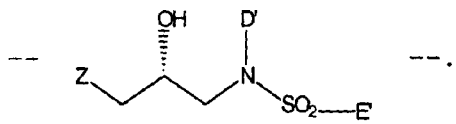

UNITED STATES PATENT AND TRADEMARK OFFICE
CERTIFICATE OF CORRECTION

PATENT NO. : 6,127,372
DATED : October 3, 2000
INVENTOR(S) : Tung et al.

It is certified that error appears in the above-identified patent and that said Letters Patent is hereby corrected as shown below:

Column 57,
Table 5, compound 1038, under column entitled "X", delete "OH" and substitute therefor -- H --.
Table 5, compound 1038, under column entitled "X' ", delete "H" and substitute therefor -- OH --.

Column 59,
Table 5, compound 1040, under column entitled "X", delete "OH" and substitute therefor -- H --.
Table 5, comound 1040, under column entitled "X' ", delete "H" and substitute therefor -- OH --.

Column 65,
Compound 1103, delete " 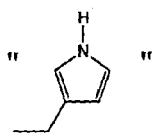 "

and substitute therefor -- 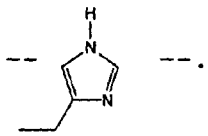 --.

Column 73,
Table 8, delete " 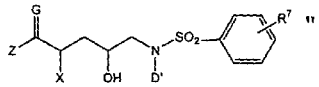 "

and substitute therefor -- 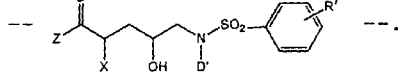 --.

Column 75,
Line 27, delete "Het;" and substitute therefor -- Ht; --.
Line 30, immediately after "which", insert -- may --.

Column 76,
Line 20, immediately after "which", insert -- may --.
Line 23, delete "Het;" and substitute therefor -- Ht; --.
Line 54, delete "S (O)" and substitute therefor -- $S(O)_n$ --.

UNITED STATES PATENT AND TRADEMARK OFFICE
CERTIFICATE OF CORRECTION

PATENT NO.  : 6,127,372
DATED       : October 3, 2000
INVENTOR(S) : Tung et al.

It is certified that error appears in the above-identified patent and that said Letters Patent is hereby corrected as shown below:

Column 78,
Line 20, delete "S (O)," and substitute therefor -- S (O) $_n$, --.
Line 26, delete "Het;" and substitute therefor -- Ht; --.
Line 39, immediately after "may" insert -- be --.
Line 45, delete "-S (O) $_n$-R$^2$-R$^2$," and substitute therefor -- -S (O) $_n$-R$^2$, --.
Line 57, imediately after "which", insert -- may --.
Line 59, delete "Het;" and substitute therefor -- Ht; --.

Column 79,
Line 9, delete "-N (D) SO$_2$Ht;" and "-N (H) A;" and substitute therefor
-- N (D) SO$_2$Ht; -- and -- N (H) A; --, respectively.

Column 82,
Line 31, delete "Het;" and substitute therefor -- Ht; --.
Line 39, delete "Het" and substitute therefor -- Ht --.

Column 83,
Line 1, delete the second occurrence of "is".
Line 29, delete "(LXIII')" substitute therefor -- (LXII') --.
Line 36, delete "Het," and substitute therefor -- Ht, --.

Column 84,
Line 47, delete "Ht;" and substitute therefor -- Ht, --.

Column 89,
Line 17, Table 10, delete "XXXII' " and substitute therefor -- XXXIII' --.

Column 100,
Line 20, delete "LXXXV' " and substitute therefor -- LXXXIV' --.
Line 25, after structure, insert -- LXXXV' --.

Column 103,
Line 53, delete "VIIf," and substitute therefor -- VIIIf, --.

UNITED STATES PATENT AND TRADEMARK OFFICE
CERTIFICATE OF CORRECTION

PATENT NO. : 6,127,372
DATED : October 3, 2000
INVENTOR(S) : Tung et al.

It is certified that error appears in the above-identified patent and that said Letters Patent is hereby corrected as shown below:

Column 104,
Line 23, delete " $\xrightarrow{\text{1. Pd/C-H}}_{\text{2. A-LG}}$ "

and substitute therefor -- $\xrightarrow{\text{1. Pd/C-H}_2}_{\text{2. A-LG}}$ --.

Line 38, delete "VIIi" and substitute therefor -- VIIIi --.

Column 105,
Line 20, delete " $\xrightarrow{\text{1. Hal-SO}_2\text{E}}_{\text{2. eptbromotryann}}$ "

and substitute therefor -- $\xrightarrow{\text{1. Hal-SO}_2\text{E}}_{\text{2. epibromohydrin}}$ --.

Column 106,
Line 1, delete "a" and substitute therefor -- an --.
Line 26, delete "Het" and substitute therefor -- Ht --.

Column 107,
Line 55, delete "VIic." and substitute therefor -- VIIc. --.

Column 108,
Line 41, delete "Het" and substitute therefor -- Ht --.
Line 42, delete "-Het' " and substitute therefor -- Ht' --.

Line 65, delete " $\xrightarrow{\text{1. HZ', EDC}}_{\text{2. p-TSOH}}$ "

and substitute therefor -- $\xrightarrow{\text{1. HZ', EDC}}_{\text{2. p-TsOH}}$ --.

Column 109,
Line 20, delete "Het" and substitute therefor -- Ht --.
Line 22, delete "Het" after formula and substitute therefor -- Ht --

Column 110,
Line 26, delete the second occurrence of "used in".

Column 116,
Line 13, delete the second occurrence of "to give".

UNITED STATES PATENT AND TRADEMARK OFFICE
CERTIFICATE OF CORRECTION

PATENT NO.    : 6,127,372
DATED         : October 3, 2000
INVENTOR(S)   : Tung et al.

It is certified that error appears in the above-identified patent and that said Letters Patent is hereby corrected as shown below:

Column 119,
Line 48, delete "10E." and substitute therefor -- 10B. --.

Column 120,
Line 46, delete "hexanel-" and substitute therefor -- hexane/ --.

Column 123-124,
Compound XXXIVd, delete

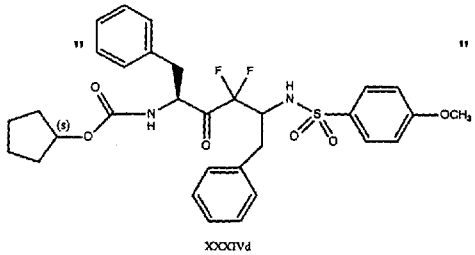

and substitute therefor

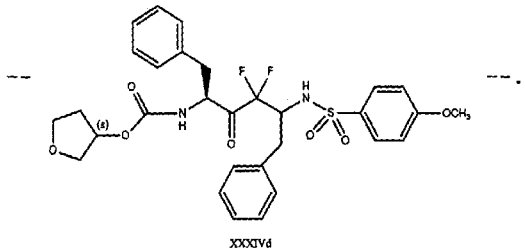

Column 125,
Line 13, delete "is".

Column 126,
Line 31, delete "it" and substitute therefor -- 1% --.

Column 128,
Line 59, delete "is".

Column 129,
Line 10, delete "materal" and substitute therefor -- material --.

Column 133,
Line 8, delete "strried" and substitute therefor -- stirred --.
Line 34, delete "DIBA" and substitute therefor -- DIEA --.

UNITED STATES PATENT AND TRADEMARK OFFICE
CERTIFICATE OF CORRECTION

PATENT NO.   : 6,127,372
DATED        : October 3, 2000
INVENTOR(S)  : Tung et al.

It is certified that error appears in the above-identified patent and that said Letters Patent is hereby corrected as shown below:

Column 139,
Line 10, delete 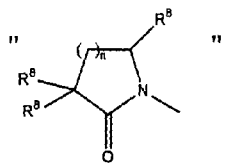

and substitute therefor 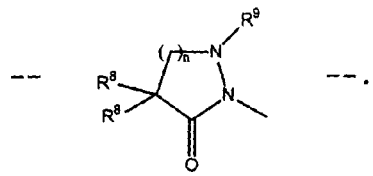

Column 141,
Line 18, immediately after "or" insert:

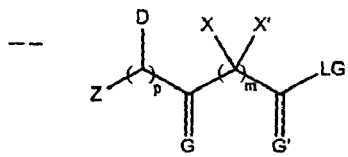

wherein:
each Hal is any halogen;
each LG is any conventional leaving group; and each D, D', Z, G, G',
X, X', p, m and E are as defined in claim 1 --.

Signed and Sealed this

Thirtieth Day of July, 2002

*Attest:*

*Attesting Officer*

JAMES E. ROGAN
*Director of the United States Patent and Trademark Office*